(12) United States Patent
Rogers et al.

(10) Patent No.: US 8,666,471 B2
(45) Date of Patent: Mar. 4, 2014

(54) IMPLANTABLE BIOMEDICAL DEVICES ON BIORESORBABLE SUBSTRATES

(75) Inventors: John A. Rogers, Champaign, IL (US); Dae-Hyeong Kim, Urbana, IL (US); Fiorenzo Omenetto, Wakefield, MA (US); David L. Kaplan, Concord, MA (US); Brian Litt, Bala Cynwyd, PA (US); Jonathan Viventi, Philadelphia, PA (US); Yonggang Huang, Glencoe, IL (US); Jason Amsden, Eddington, ME (US)

(73) Assignees: The Board of Trustees of the University of Illinois, Urbana, IL (US); Northwestern University, Evanston, IL (US); Trustees of Tufts College, Medford, MA (US); The Trustees of the University of Pennsylvania, Philadelphia, PA (US)

( * ) Notice: Subject to any disclaimer, the term of this patent is extended or adjusted under 35 U.S.C. 154(b) by 263 days.

(21) Appl. No.: 12/892,001

(22) Filed: Sep. 28, 2010

(65) Prior Publication Data

US 2011/0230747 A1      Sep. 22, 2011

Related U.S. Application Data

(60) Provisional application No. 61/314,739, filed on Mar. 17, 2010.

(51) Int. Cl.
*A61B 5/04* (2006.01)
*A61N 1/05* (2006.01)

(52) U.S. Cl.
USPC ........... 600/377; 600/393; 600/373; 600/395; 607/116

(58) Field of Classification Search
USPC ......... 600/372, 373, 377, 393, 395, 301, 116; 29/825; 128/898; 607/116
See application file for complete search history.

(56) References Cited

U.S. PATENT DOCUMENTS

| | | | |
|---|---|---|---|
| 3,949,410 | A | 4/1976 | Bassous |
| 4,058,418 | A | 11/1977 | Lindmayer |

(Continued)

FOREIGN PATENT DOCUMENTS

| | | |
|---|---|---|
| CN | 1222758 | 7/1999 |
| CN | 1454045 | 11/2003 |

(Continued)

OTHER PUBLICATIONS

Notice of Reasons for Rejection corresponding to Japanese Patent Application No. P2008-514820, Dispatched May 8, 2012—includes English translation.

(Continued)

*Primary Examiner* — Linda Dvorak
*Assistant Examiner* — Erin M Cardinal
(74) *Attorney, Agent, or Firm* — Lathrop & Gage LLP

(57) ABSTRACT

Provided herein are implantable biomedical devices, methods of administering implantable biomedical devices, methods of making implantable biomedical devices, and methods of using implantable biomedical devices to actuate a target tissue or sense a parameter associated with the target tissue in a biological environment. Each implantable biomedical device comprises a bioresorbable substrate, an electronic device having a plurality of inorganic semiconductor components supported by the bioresorbable substrate, and a barrier layer encapsulating at least a portion of the inorganic semiconductor components. Upon contact with a biological environment the bioresorbable substrate is at least partially resorbed, thereby establishing conformal contact between the implantable biomedical device and the target tissue in the biological environment.

52 Claims, 25 Drawing Sheets

(56) References Cited

U.S. PATENT DOCUMENTS

| | | |
|---|---|---|
| 4,392,451 A | 7/1983 | Mickelsen et al. |
| 4,471,003 A | 9/1984 | Cann |
| 4,487,162 A | 12/1984 | Cann |
| 4,663,828 A | 5/1987 | Hanak |
| 4,761,335 A | 8/1988 | Aurichio et al. |
| 4,766,670 A | 8/1988 | Gazdik et al. |
| 4,784,720 A | 11/1988 | Douglas |
| 4,855,017 A | 8/1989 | Douglas |
| 5,041,973 A | 8/1991 | Lebron et al. |
| 5,118,400 A | 6/1992 | Wollam |
| 5,178,957 A | 1/1993 | Kolpe et al. |
| 5,204,144 A | 4/1993 | Cann et al. |
| 5,313,094 A | 5/1994 | Beyer et al. |
| 5,339,180 A | 8/1994 | Katoh |
| 5,376,820 A | 12/1994 | Crafts et al. |
| 5,403,700 A | 4/1995 | Heller et al. |
| 5,427,096 A | 6/1995 | Bogusiewicz et al. |
| 5,434,751 A | 7/1995 | Cole, Jr. et al. |
| 5,455,178 A | 10/1995 | Fattinger |
| 5,469,845 A | 11/1995 | DeLonzor et al. |
| 5,501,893 A | 3/1996 | Laermer et al. |
| 5,512,218 A | 4/1996 | Gresser et al. |
| 5,525,815 A | 6/1996 | Einset |
| 5,545,291 A | 8/1996 | Smith et al. |
| 5,625,471 A | 4/1997 | Smith |
| 5,648,148 A | 7/1997 | Simpson |
| 5,653,742 A * | 8/1997 | Parker et al. .................. 607/137 |
| 5,687,737 A | 11/1997 | Branham et al. |
| 5,691,245 A | 11/1997 | Bakhit |
| 5,753,529 A | 5/1998 | Chang et al. |
| 5,757,081 A | 5/1998 | Chang et al. |
| 5,767,578 A | 6/1998 | Chang et al. |
| 5,772,905 A | 6/1998 | Chou |
| 5,783,856 A | 7/1998 | Smith et al. |
| 5,790,151 A | 8/1998 | Mills |
| 5,817,242 A | 10/1998 | Biebuyck et al. |
| 5,824,186 A | 10/1998 | Smith et al. |
| 5,904,545 A | 5/1999 | Smith et al. |
| 5,907,189 A | 5/1999 | Mertol |
| 5,915,180 A | 6/1999 | Hara et al. |
| 5,917,534 A | 6/1999 | Rajeswaran |
| 5,928,001 A | 7/1999 | Gillette et al. |
| 5,954,715 A * | 9/1999 | Harrington et al. ............ 606/28 |
| 5,955,781 A | 9/1999 | Joshi et al. |
| 5,976,683 A | 11/1999 | Liehrr et al. |
| 5,998,291 A | 12/1999 | Bakhit et al. |
| 6,024,702 A | 2/2000 | Iversen |
| 6,057,212 A | 5/2000 | Chan et al. |
| 6,080,608 A | 6/2000 | Nowak |
| 6,091,979 A * | 7/2000 | Madsen ........................ 600/377 |
| 6,097,984 A | 8/2000 | Douglas |
| 6,134,045 A | 10/2000 | Jiang et al. |
| 6,165,391 A | 12/2000 | Vedamuttu |
| 6,171,730 B1 | 1/2001 | Kuroda et al. |
| 6,225,149 B1 | 5/2001 | Gan et al. |
| 6,236,883 B1 | 5/2001 | Ciaccio et al. |
| 6,265,326 B1 | 7/2001 | Ueno |
| 6,274,508 B1 | 8/2001 | Jacobsen et al. |
| 6,276,775 B1 | 8/2001 | Schulte |
| 6,277,712 B1 | 8/2001 | Kang et al. |
| 6,281,038 B1 | 8/2001 | Jacobsen et al. |
| 6,284,418 B1 | 9/2001 | Trantolo |
| 6,291,896 B1 | 9/2001 | Smith |
| 6,316,278 B1 | 11/2001 | Jacobsen et al. |
| 6,316,283 B1 | 11/2001 | Saurer |
| 6,317,175 B1 | 11/2001 | Salerno et al. |
| 6,322,895 B1 | 11/2001 | Canham |
| 6,330,481 B1 * | 12/2001 | Van Wijk et al. ............. 607/129 |
| 6,334,960 B1 | 1/2002 | Willson et al. |
| 6,380,729 B1 | 4/2002 | Smith |
| 6,403,397 B1 | 6/2002 | Katz |
| 6,413,790 B1 | 7/2002 | Duthaler et al. |
| 6,417,025 B1 | 7/2002 | Gengel |
| 6,420,266 B1 | 7/2002 | Smith et al. |
| 6,433,401 B1 | 8/2002 | Clark et al. |
| 6,451,191 B1 | 9/2002 | Bentsen et al. |
| 6,459,418 B1 | 10/2002 | Comiskey et al. |
| 6,468,638 B2 | 10/2002 | Jacobsen et al. |
| 6,479,395 B1 | 11/2002 | Smith et al. |
| 6,517,995 B1 | 2/2003 | Jacobson et al. |
| 6,527,964 B1 | 3/2003 | Smith et al. |
| 6,555,408 B1 | 4/2003 | Jacobsen et al. |
| 6,559,905 B1 | 5/2003 | Akiyama |
| 6,566,744 B2 | 5/2003 | Gengel |
| 6,580,151 B2 | 6/2003 | Vandeputte et al. |
| 6,586,338 B2 | 7/2003 | Smith et al. |
| 6,590,346 B1 | 7/2003 | Hadley et al. |
| 6,606,079 B1 | 8/2003 | Smith |
| 6,606,247 B2 | 8/2003 | Credelle et al. |
| 6,608,370 B1 | 8/2003 | Chen et al. |
| 6,623,579 B1 | 9/2003 | Smith et al. |
| 6,639,578 B1 | 10/2003 | Comiskey et al. |
| 6,655,286 B2 | 12/2003 | Rogers |
| 6,657,289 B1 | 12/2003 | Craig et al. |
| 6,661,037 B2 | 12/2003 | Pan et al. |
| 6,665,044 B1 | 12/2003 | Jacobsen et al. |
| 6,666,821 B2 | 12/2003 | Keimel |
| 6,683,663 B1 | 1/2004 | Hadley et al. |
| 6,693,384 B1 | 2/2004 | Vicentini et al. |
| 6,706,402 B2 | 3/2004 | Rueckes et al. |
| 6,720,469 B1 | 4/2004 | Curtis et al. |
| 6,723,576 B2 | 4/2004 | Nozawa et al. |
| 6,730,990 B2 | 5/2004 | Kondo et al. |
| 6,731,353 B1 | 5/2004 | Credelle et al. |
| 6,743,982 B2 | 6/2004 | Biegelsen et al. |
| 6,780,696 B1 | 8/2004 | Schatz |
| 6,784,450 B2 | 8/2004 | Pan et al. |
| 6,787,052 B1 | 9/2004 | Vaganov |
| 6,814,898 B1 | 11/2004 | Deeman et al. |
| 6,816,380 B2 | 11/2004 | Credelle et al. |
| 6,844,673 B1 | 1/2005 | Bernkopf |
| 6,848,162 B2 | 2/2005 | Arneson et al. |
| 6,850,312 B2 | 2/2005 | Jacobsen et al. |
| 6,856,830 B2 | 2/2005 | He |
| 6,863,219 B1 | 3/2005 | Jacobsen et al. |
| 6,864,435 B2 | 3/2005 | Hermanns et al. |
| 6,864,570 B2 | 3/2005 | Smith |
| 6,872,645 B2 | 3/2005 | Duan et al. |
| 6,878,871 B2 | 4/2005 | Scher et al. |
| 6,881,979 B2 | 4/2005 | Starikov et al. |
| 6,887,450 B2 | 5/2005 | Chen et al. |
| 6,900,094 B2 | 5/2005 | Hammond et al. |
| 6,917,061 B2 | 7/2005 | Pan et al. |
| 6,936,181 B2 | 8/2005 | Bulthaup et al. |
| 6,949,199 B1 | 9/2005 | Gauzner et al. |
| 6,949,206 B2 | 9/2005 | Whiteford et al. |
| 6,950,220 B2 | 9/2005 | Abramson et al. |
| 6,984,934 B2 | 1/2006 | Moller et al. |
| 6,989,285 B2 | 1/2006 | Ball |
| 7,029,951 B2 | 4/2006 | Chen et al. |
| 7,033,961 B1 | 4/2006 | Smart et al. |
| 7,067,903 B2 | 6/2006 | Tachibana et al. |
| 7,116,318 B2 | 10/2006 | Amundson et al. |
| 7,132,313 B2 | 11/2006 | O'Connor et al. |
| 7,148,512 B2 | 12/2006 | Leu et al. |
| 7,158,277 B2 | 1/2007 | Berggren et al. |
| 7,169,546 B2 | 1/2007 | Suzuki et al. |
| 7,169,669 B2 | 1/2007 | Blakers et al. |
| 7,170,164 B2 | 1/2007 | Chen et al. |
| 7,186,624 B2 | 3/2007 | Welser et al. |
| 7,190,051 B2 | 3/2007 | Mech et al. |
| 7,195,733 B2 | 3/2007 | Rogers et al. |
| 7,223,609 B2 | 5/2007 | Anvar et al. |
| 7,253,442 B2 | 8/2007 | Huang et al. |
| 7,255,919 B2 | 8/2007 | Sakata et al. |
| 7,291,540 B2 | 11/2007 | Mech et al. |
| 7,374,968 B2 | 5/2008 | Kornilivich et al. |
| 7,425,523 B2 | 9/2008 | Ikemizu et al. |
| 7,521,292 B2 | 4/2009 | Rogers et al. |
| 7,557,367 B2 | 7/2009 | Rogers et al. |
| 7,622,367 B1 | 11/2009 | Nuzzo et al. |
| 7,629,691 B2 | 12/2009 | Roush et al. |
| 7,635,755 B2 | 12/2009 | Kaplan et al. |
| 7,674,882 B2 | 3/2010 | Kaplan et al. |

(56) References Cited

U.S. PATENT DOCUMENTS

| | | |
|---|---|---|
| 7,700,402 B2 | 4/2010 | Wild et al. |
| 7,704,684 B2 | 4/2010 | Rogers et al. |
| 7,705,280 B2 | 4/2010 | Nuzzo et al. |
| 7,709,961 B2 | 5/2010 | Greenberg et al. |
| 7,727,575 B2 | 6/2010 | Kaplan et al. |
| 7,799,699 B2 | 9/2010 | Nuzzo et al. |
| 7,842,780 B2 | 11/2010 | Kaplan et al. |
| 7,844,345 B2 * | 11/2010 | Boling et al. ................ 607/116 |
| 7,932,123 B2 | 4/2011 | Rogers et al. |
| 7,943,491 B2 | 5/2011 | Nuzzo et al. |
| 7,972,875 B2 | 7/2011 | Rogers et al. |
| 7,982,296 B2 | 7/2011 | Nuzzo et al. |
| 8,039,847 B2 | 10/2011 | Nuzzo et al. |
| 8,198,621 B2 | 6/2012 | Rogers et al. |
| 8,217,381 B2 | 7/2012 | Rogers et al. |
| 8,386,006 B2 * | 2/2013 | Schouenborg ................ 600/373 |
| 8,440,546 B2 | 5/2013 | Rogers et al. |
| 8,478,422 B2 * | 7/2013 | Epstein et al. ................ 607/66 |
| 8,552,299 B2 | 10/2013 | Rogers et al. |
| 2001/0003043 A1 | 6/2001 | Metspalu et al. |
| 2002/0021445 A1 | 2/2002 | Bozhevolnyi et al. |
| 2002/0110766 A1 | 8/2002 | Tsai et al. |
| 2003/0003759 A1 | 1/2003 | Kudelka |
| 2003/0006527 A1 | 1/2003 | Rabolt et al. |
| 2003/0032892 A1 | 2/2003 | Erlach et al. |
| 2003/0082889 A1 | 5/2003 | Maruyama et al. |
| 2003/0087476 A1 | 5/2003 | Oohata et al. |
| 2003/0138704 A1 | 7/2003 | Mei et al. |
| 2003/0149456 A1 | 8/2003 | Rottenberg et al. |
| 2003/0178316 A1 | 9/2003 | Jacobs et al. |
| 2003/0227116 A1 | 12/2003 | Halik et al. |
| 2004/0005723 A1 | 1/2004 | Empedocles et al. |
| 2004/0026684 A1 | 2/2004 | Empedocles et al. |
| 2004/0079464 A1 | 4/2004 | Kumakura |
| 2004/0081384 A1 | 4/2004 | Datesman et al. |
| 2004/0095658 A1 | 5/2004 | Buretea et al. |
| 2004/0112964 A1 | 6/2004 | Empedocles et al. |
| 2004/0136866 A1 | 7/2004 | Pontis et al. |
| 2004/0146560 A1 | 7/2004 | Whiteford et al. |
| 2004/0155290 A1 | 8/2004 | Mech et al. |
| 2004/0176312 A1 * | 9/2004 | Gillis ................ 514/36 |
| 2004/0178390 A1 | 9/2004 | Whiteford |
| 2004/0192082 A1 | 9/2004 | Wagner et al. |
| 2004/0200734 A1 | 10/2004 | Co et al. |
| 2004/0206448 A1 | 10/2004 | Dubrow |
| 2004/0211458 A1 | 10/2004 | Gui et al. |
| 2004/0211459 A1 | 10/2004 | Suenaga et al. |
| 2004/0250950 A1 | 12/2004 | Dubrow |
| 2004/0252559 A1 | 12/2004 | Gupta |
| 2005/0020094 A1 | 1/2005 | Forbes et al. |
| 2005/0038498 A1 | 2/2005 | Dubrow et al. |
| 2005/0082526 A1 | 4/2005 | Bedell et al. |
| 2005/0124712 A1 | 6/2005 | Anderson et al. |
| 2005/0133954 A1 | 6/2005 | Homola |
| 2005/0149158 A1 * | 7/2005 | Hunter et al. ................ 607/119 |
| 2005/0192636 A1 * | 9/2005 | Skiba et al. ................ 607/2 |
| 2005/0214962 A1 | 9/2005 | Daniels et al. |
| 2005/0227389 A1 | 10/2005 | Bhattacharya et al. |
| 2005/0233546 A1 | 10/2005 | Oohata et al. |
| 2005/0238967 A1 | 10/2005 | Rogers et al. |
| 2005/0255686 A1 | 11/2005 | Yamano et al. |
| 2005/0260706 A1 | 11/2005 | Kaplan et al. |
| 2005/0261561 A1 | 11/2005 | Jones et al. |
| 2006/0038182 A1 | 2/2006 | Rogers et al. |
| 2006/0049485 A1 | 3/2006 | Pan et al. |
| 2006/0076561 A1 | 4/2006 | Hioki et al. |
| 2006/0084012 A1 | 4/2006 | Nuzzo et al. |
| 2006/0085976 A1 | 4/2006 | Eldridge et al. |
| 2006/0102525 A1 | 5/2006 | Volkel et al. |
| 2006/0119853 A1 | 6/2006 | Baumberg et al. |
| 2006/0127817 A1 | 6/2006 | Ramanujan et al. |
| 2006/0129056 A1 | 6/2006 | Leuthardt et al. |
| 2006/0132025 A1 | 6/2006 | Gao et al. |
| 2006/0134893 A1 | 6/2006 | Savage et al. |
| 2006/0141617 A1 | 6/2006 | Desai et al. |
| 2006/0159837 A1 | 7/2006 | Kaplan et al. |
| 2006/0169989 A1 | 8/2006 | Bhattacharya et al. |
| 2006/0173364 A1 | 8/2006 | Clancy et al. |
| 2006/0177479 A1 | 8/2006 | Giachelli et al. |
| 2006/0178655 A1 | 8/2006 | Santini et al. |
| 2006/0244105 A1 | 11/2006 | Forbes et al. |
| 2006/0255341 A1 | 11/2006 | Pinnington et al. |
| 2006/0273279 A1 | 12/2006 | Kaplan et al. |
| 2006/0279191 A1 | 12/2006 | Geohegan et al. |
| 2006/0286488 A1 | 12/2006 | Rogers et al. |
| 2006/0286785 A1 | 12/2006 | Rogers et al. |
| 2007/0009968 A1 | 1/2007 | Cunningham et al. |
| 2007/0031607 A1 | 2/2007 | Dubson et al. |
| 2007/0032089 A1 | 2/2007 | Nuzzo et al. |
| 2007/0043416 A1 | 2/2007 | Callas et al. |
| 2007/0058254 A1 | 3/2007 | Kim |
| 2007/0073130 A1 | 3/2007 | Finch et al. |
| 2007/0187862 A1 | 8/2007 | Kaplan et al. |
| 2007/0212730 A1 | 9/2007 | Vepari et al. |
| 2007/0227586 A1 | 10/2007 | Zapalac |
| 2007/0233208 A1 | 10/2007 | Kurtz et al. |
| 2008/0000871 A1 | 1/2008 | Suh et al. |
| 2008/0038236 A1 | 2/2008 | Gimble et al. |
| 2008/0041617 A1 | 2/2008 | Chen et al. |
| 2008/0055581 A1 | 3/2008 | Rogers et al. |
| 2008/0085272 A1 | 4/2008 | Kaplan et al. |
| 2008/0090322 A1 | 4/2008 | Mech et al. |
| 2008/0102096 A1 | 5/2008 | Molin et al. |
| 2008/0108171 A1 | 5/2008 | Rogers et al. |
| 2008/0152281 A1 | 6/2008 | Lundquist et al. |
| 2008/0157235 A1 | 7/2008 | Rogers et al. |
| 2008/0183076 A1 | 7/2008 | Witte et al. |
| 2008/0203431 A1 | 8/2008 | Garcia et al. |
| 2008/0212102 A1 | 9/2008 | Nuzzo et al. |
| 2008/0239755 A1 | 10/2008 | Parker et al. |
| 2008/0243217 A1 * | 10/2008 | Wildon ................ 607/116 |
| 2008/0280360 A1 | 11/2008 | Kaplan et al. |
| 2008/0288037 A1 | 11/2008 | Neysmith et al. |
| 2008/0293919 A1 | 11/2008 | Kaplan et al. |
| 2008/0306359 A1 | 12/2008 | Zdeblick et al. |
| 2009/0004737 A1 | 1/2009 | Borenstein et al. |
| 2009/0028910 A1 | 1/2009 | DeSimone et al. |
| 2009/0149930 A1 | 6/2009 | Schenck |
| 2009/0198293 A1 | 8/2009 | Cauller et al. |
| 2009/0199960 A1 | 8/2009 | Nuzzo et al. |
| 2009/0202614 A1 | 8/2009 | Kaplan et al. |
| 2009/0208555 A1 | 8/2009 | Kuttler et al. |
| 2009/0221896 A1 | 9/2009 | Rickert et al. |
| 2009/0232963 A1 | 9/2009 | Kaplan et al. |
| 2009/0234026 A1 | 9/2009 | Kaplan et al. |
| 2009/0289246 A1 | 11/2009 | Schneider et al. |
| 2009/0294803 A1 | 12/2009 | Nuzzo et al. |
| 2010/0002402 A1 | 1/2010 | Rogers et al. |
| 2010/0028451 A1 | 2/2010 | Kaplan et al. |
| 2010/0046902 A1 | 2/2010 | Kaplan et al. |
| 2010/0052112 A1 | 3/2010 | Rogers et al. |
| 2010/0055438 A1 | 3/2010 | Kaplan et al. |
| 2010/0059863 A1 | 3/2010 | Rogers et al. |
| 2010/0063404 A1 | 3/2010 | Kaplan et al. |
| 2010/0065784 A1 | 3/2010 | Kaplan et al. |
| 2010/0068740 A1 | 3/2010 | Kaplan et al. |
| 2010/0070068 A1 | 3/2010 | Kaplan et al. |
| 2010/0072577 A1 | 3/2010 | Nuzzo et al. |
| 2010/0096763 A1 | 4/2010 | Kaplan et al. |
| 2010/0120116 A1 | 5/2010 | Kaplan et al. |
| 2010/0121420 A1 | 5/2010 | Fiset et al. |
| 2010/0152651 A1 * | 6/2010 | Boyden et al. ................ 604/66 |
| 2010/0160999 A1 * | 6/2010 | Epstein et al. ................ 607/50 |
| 2010/0176705 A1 | 7/2010 | Van Herpen et al. |
| 2010/0178304 A1 | 7/2010 | Wang et al. |
| 2010/0191328 A1 | 7/2010 | Kaplan et al. |
| 2010/0196447 A1 | 8/2010 | Kaplan et al. |
| 2010/0200752 A1 | 8/2010 | Lee et al. |
| 2010/0203226 A1 | 8/2010 | Kaplan et al. |
| 2010/0252840 A1 | 10/2010 | Ibbetson et al. |
| 2010/0279112 A1 | 11/2010 | Kaplan et al. |
| 2010/0283069 A1 | 11/2010 | Rogers et al. |
| 2010/0289124 A1 | 11/2010 | Nuzzo et al. |
| 2010/0317132 A1 | 12/2010 | Rogers et al. |

(56) References Cited

U.S. PATENT DOCUMENTS

| | | |
|---|---|---|
| 2011/0068672 A1 | 3/2011 | Hasnain |
| 2011/0147715 A1 | 6/2011 | Rogers et al. |
| 2011/0170225 A1 | 7/2011 | Rogers et al. |
| 2011/0171813 A1 | 7/2011 | Rogers et al. |
| 2011/0187798 A1 | 8/2011 | Rogers et al. |
| 2011/0220890 A1 | 9/2011 | Nuzzo et al. |
| 2011/0230747 A1 | 9/2011 | Rogers et al. |
| 2011/0245914 A1 | 10/2011 | Santini, Jr. et al. |
| 2011/0266561 A1 | 11/2011 | Rogers et al. |
| 2011/0276124 A1 | 11/2011 | Doerr et al. |
| 2011/0277813 A1 | 11/2011 | Rogers et al. |
| 2011/0316120 A1 | 12/2011 | Rogers et al. |
| 2012/0105528 A1 | 5/2012 | Rogers et al. |
| 2012/0157804 A1 | 6/2012 | Rogers et al. |
| 2012/0165759 A1* | 6/2012 | Rogers et al. ............... 604/264 |
| 2012/0223293 A1* | 9/2012 | Borenstein et al. .......... 257/40 |
| 2013/0100618 A1 | 4/2013 | Rogers et al. |
| 2013/0140649 A1 | 6/2013 | Rogers et al. |

FOREIGN PATENT DOCUMENTS

| | | |
|---|---|---|
| CN | 101772348 A | 7/2010 |
| DE | 424104501 C1 | 5/1994 |
| DE | 19748173 | 5/1999 |
| EP | 0929097 | 7/1999 |
| EP | 1 025 988 | 8/2000 |
| EP | 1357773 | 10/2003 |
| EP | 1 467 224 | 10/2004 |
| EP | 1 477 230 | 11/2004 |
| EP | 1 498 456 | 1/2005 |
| EP | 1 511 096 | 3/2005 |
| EP | 1 558 444 | 8/2005 |
| EP | 1 613 796 | 1/2006 |
| EP | 1 773 240 | 4/2007 |
| EP | 1 915 436 | 4/2008 |
| EP | 1 726 329 | 8/2009 |
| EP | 2 086 749 | 8/2009 |
| EP | 2 101 975 | 9/2009 |
| EP | 2 107 964 | 10/2009 |
| EP | 2 109 634 | 10/2009 |
| EP | 2 129 772 | 12/2009 |
| EP | 2 206 017 | 7/2010 |
| EP | 2 211 876 | 8/2010 |
| EP | 2 249 886 | 11/2010 |
| JP | 06-118441 | 4/1994 |
| JP | 6-163365 | 6/1994 |
| JP | 11-026344 | 1/1999 |
| JP | 1-135853 | 2/1999 |
| JP | 11-123791 | 5/1999 |
| JP | 11-142878 | 5/1999 |
| JP | 11-183854 | 7/1999 |
| JP | 2000-180969 | 6/2000 |
| JP | 2001-007340 | 1/2001 |
| JP | 2001147301 | 5/2001 |
| JP | 2002092984 | 3/2002 |
| JP | 2004307661 | 11/2004 |
| JP | 2006-504450 | 2/2006 |
| JP | 2006119424 | 5/2006 |
| JP | 2006-186294 | 7/2006 |
| JP | 2007-515391 | 6/2007 |
| JP | 2008-502739 | 1/2008 |
| JP | 2009536422 | 10/2009 |
| JP | 2010-508852 | 3/2010 |
| JP | 2010-509593 | 3/2010 |
| JP | 2010-509644 | 3/2010 |
| JP | 2010-509645 | 3/2010 |
| JP | 2010509645 | 3/2010 |
| JP | 2010-522583 | 7/2010 |
| JP | 2010-529230 | 8/2010 |
| KR | 10-2008-0069553 | 7/2008 |
| TW | 367570 | 8/1999 |
| TW | 494257 | 7/2002 |
| TW | 200836353 | 9/2008 |
| WO | WO 96/21245 | 7/1996 |
| WO | WO 98/49936 | 11/1998 |
| WO | WO 99/45860 | 9/1999 |
| WO | WO 00/46854 | 8/2000 |
| WO | WO 00/49421 | 8/2000 |
| WO | WO 00/49658 | 8/2000 |
| WO | WO 00/55915 | 9/2000 |
| WO | WO 00/55916 | 9/2000 |
| WO | WO 01/31082 | 5/2001 |
| WO | WO 01/33621 | 5/2001 |
| WO | WO 01/66833 | 9/2001 |
| WO | WO 01/98838 | 12/2001 |
| WO | WO 02/27701 | 4/2002 |
| WO | WO 02/43032 | 5/2002 |
| WO | WO 02/45160 | 6/2002 |
| WO | WO 02/071137 | 9/2002 |
| WO | WO 02/073699 | 9/2002 |
| WO | WO 02/092778 | 11/2002 |
| WO | WO 02/097724 | 12/2002 |
| WO | WO 2004/099068 | 12/2002 |
| WO | WO 03/030194 | 4/2003 |
| WO | WO 03/032240 | 4/2003 |
| WO | WO 03/049201 | 6/2003 |
| WO | WO 03/063211 | 7/2003 |
| WO | WO 03/085700 | 10/2003 |
| WO | WO 03/085701 | 10/2003 |
| WO | WO 03/092073 | 11/2003 |
| WO | WO 04/000915 | 12/2003 |
| WO | WO 04/001103 | 12/2003 |
| WO | WO 2004/003535 | 1/2004 |
| WO | WO 2004/022637 | 3/2004 |
| WO | WO 2004/022714 | 3/2004 |
| WO | WO 2004/023527 | 3/2004 |
| WO | WO 2004/024407 | 3/2004 |
| WO | WO 2004/027822 | 4/2004 |
| WO | WO 2004/032190 | 4/2004 |
| WO | WO 2004/032191 | 4/2004 |
| WO | WO 2004/032193 | 4/2004 |
| WO | WO 2004/034025 | 4/2004 |
| WO | WO 2004/062697 | 7/2004 |
| WO | WO 2004/086289 | 10/2004 |
| WO | WO 2004/094303 | 11/2004 |
| WO | WO 2004/100252 | 11/2004 |
| WO | WO 2004/105456 | 12/2004 |
| WO | WO 2004/107973 | 12/2004 |
| WO | WO 2005/000483 | 1/2005 |
| WO | WO 2005/005679 | 1/2005 |
| WO | WO 2005/012606 | 2/2005 |
| WO | WO 2005/015480 | 2/2005 |
| WO | WO 2005/017962 | 2/2005 |
| WO | WO 2005/022120 | 3/2005 |
| WO | WO 2005/029578 | 3/2005 |
| WO | WO 2005/031724 | 4/2005 |
| WO | WO 2005/033786 | 4/2005 |
| WO | WO 2005/033787 | 4/2005 |
| WO | WO 2005/054119 | 6/2005 |
| WO | WO 2005/099310 | 10/2005 |
| WO | WO 2005/104756 | 11/2005 |
| WO | WO 2005/106934 | 11/2005 |
| WO | WO 02/097708 | 12/2005 |
| WO | WO 2005/122285 | 12/2005 |
| WO | WO 2005/123114 | 12/2005 |
| WO | WO 2006/028996 | 3/2006 |
| WO | WO 2006/042287 | 4/2006 |
| WO | WO 2006/076711 | 7/2006 |
| WO | WO 2006/104069 | 10/2006 |
| WO | WO 2006/130558 | 12/2006 |
| WO | WO 2006/130721 | 12/2006 |
| WO | WO 2007/000037 | 1/2007 |
| WO | WO 2007/016524 | 2/2007 |
| WO | WO 2007/028003 | 3/2007 |
| WO | WO 2007/056183 | 5/2007 |
| WO | WO 2007/126412 | 11/2007 |
| WO | WO 2008/030666 | 3/2008 |
| WO | WO 2008/030960 | 3/2008 |
| WO | WO 2008/036837 | 3/2008 |
| WO | WO 2008/055054 | 5/2008 |
| WO | WO 2008/085904 | 7/2008 |
| WO | WO 2008/103464 | 8/2008 |
| WO | WO 2008/106485 | 9/2008 |

(56) References Cited

FOREIGN PATENT DOCUMENTS

| WO | WO 2008/108838 | 9/2008 |
|---|---|---|
| WO | WO 2007/132390 | 10/2008 |
| WO | WO 2008/118133 | 10/2008 |
| WO | WO 2008/118211 | 10/2008 |
| WO | WO 2008/127401 | 10/2008 |
| WO | WO 2008/127402 | 10/2008 |
| WO | WO 2008/127403 | 10/2008 |
| WO | WO 2008/127404 | 10/2008 |
| WO | WO 2008/127405 | 10/2008 |
| WO | WO 2008/140562 | 11/2008 |
| WO | WO 2008/143635 | 11/2008 |
| WO | WO 2008/150861 | 12/2008 |
| WO | WO 2009/011709 | 1/2009 |
| WO | WO 2009/023615 | 2/2009 |
| WO | WO 2009/061823 | 5/2009 |
| WO | WO 2009/075625 | 6/2009 |
| WO | WO 2009/076088 | 6/2009 |
| WO | WO 2009/090398 | 7/2009 |
| WO | WO 2009/100280 | 8/2009 |
| WO | WO 2009/111641 | 9/2009 |
| WO | WO 2009/114115 | 9/2009 |
| WO | WO 2009/114689 | 9/2009 |
| WO | WO 2009/118678 | 10/2009 |
| WO | WO 2009/126689 | 10/2009 |
| WO | WO 2009/140588 | 11/2009 |
| WO | WO 2009/155397 | 12/2009 |
| WO | WO 2010/005707 | 1/2010 |
| WO | WO 2010/036807 | 4/2010 |
| WO | WO 2010/036992 | 4/2010 |
| WO | WO 2010/040528 | 4/2010 |
| WO | WO 2010/042798 | 4/2010 |
| WO | WO 2010/049881 | 5/2010 |
| WO | WO 2010/057142 | 5/2010 |
| WO | WO 2010/065957 | 6/2010 |
| WO | WO 2010/126640 | 11/2010 |
| WO | WO 2010/132552 | 11/2010 |
| WO | WO 2010/141133 | 12/2010 |
| WO | WO 2011/005381 | 1/2011 |
| WO | WO 2011/006133 | 1/2011 |
| WO | WO 2011/008842 | 1/2011 |
| WO | WO 2011/011347 | 1/2011 |
| WO | WO 2011/026101 | 3/2011 |
| WO | WO 2011/038401 | 3/2011 |
| WO | WO 2011/041395 | 4/2011 |
| WO | WO 2011/046652 | 4/2011 |
| WO | WO 2011/084450 | 7/2011 |
| WO | WO 2011/112931 | 9/2011 |
| WO | WO 2011/115643 | 9/2011 |
| WO | WO 2011/130335 | 10/2011 |
| WO | WO 2013/089867 | 6/2013 |

OTHER PUBLICATIONS

Notice of Reasons for Rejection corresponding to Japanese Patent Application No. P2006-165159, Dispatched Apr. 24, 2012—includes English translation.
Notice of Reasons for Rejection corresponding to Japanese Patent Application No. P2009-546361, Dispatched Jul. 3, 2012—includes English translation.
Hölke et al. (1999), "Ultra-deep anisotropic etching of (110) silicon", Journal of Micromechanics & Microengineering, vol. 9, No. 1, pp. 51-57.
Alavi et al. (1992), "Fabrication of Microchannels by Laser Machining and Anisotropic Etching of Silicon", Sensors and Actuators A, vol. A32, No. 1/3, pp. 299-302.
Extended European Search Report dated Apr. 4, 2012 for corresponding European Patent Application No. 06771761.1.
Supplementary European Search Report dated Jun. 15, 2012, corresponding to European Patent Application No. 09 71 6695.
International Search Report and Written Opinion dated Jul. 30, 2012, corresponding to International Patent Application No. PCT/US12/37973.

Abbaschian et al. (Dec. 2005) "High Pressure-High Temperature Growth of Diamond Crystals Using Split Sphere Apparatus," *Diamond Relat. Mater.* 14(11-12):1916-1919.
Adachi et al (1982) "Chemical Etching of InGaAsP/InP DH Wafer," *J. Electrochem. Soc.* 129:1053-1062.
Adachi et al. (1983) "Chemical Etching Characteristics of (001)GaAs," *J. Electrochem. Soc.* 130:2427-2435.
Adrega et al. (2010) "Stretchable Gold Conductors Embedded in PDMS and Patterned by Photolithography: Fabrication and Electromechanical Characterization," *J. Micromech. Microeng.* 20:055025.
Ago et al. (2005) "Aligned Growth of Isolated Single-Walled Carbon Nanotubes Programmed by Atomic Arrangement of Substrate Surface," *Chem. Phys. Lett.* 408:433-438.
Ago et al. (2006) "Synthesis of Horizontally-Aligned Single-Walled Carbon Nanotubes with Controllable Density on Sapphire Surface and Polarized Raman Spectroscopy," *Chem. Phys. Lett.* 421:399-403.
Ahmed et al. (Web Release Oct. 11, 2005) "Extending the $3\omega$-Method to the MHz Range for Thermal Conductivity Measurements of Diamond Thin Films," *Diamond Relat. Mater.* 15(2-3):389-393.
Ahn et al. (2007) "Bendable Integrated Circuits on Plastic Substrates by Use of Printed Ribbons of Single-Crystalline Silicon," *Appl. Phys. Lett.* 90:213501.
Ahn et al. (Dec. 15, 2006) "Heterogeneous Three-Dimensional Electronics by Use of Printed Semiconductor Nanomaterials," *Science* 314:1754-1757.
Ahn et al. (Jun. 2006) "High-Speed Mechanically Flexible Single-Crystal Silicon Thin-Film Transistors on Plastic Substrates," *IEEE Electron Dev. Lett.* 27(6):460-462.
Al-Halhouli et al. (2008) "Nanoindentation Testing of SU-8 Photoresist Mechanical Properties," *Microelectronic Eng.* 85:942-944.
Aliot, E. M. et al. (2009) "EHRA/HRS Expert Consensus on Catheter Ablation of Ventricular Arrhythmias: Developed in a partnership with the European Heart Rhythm Association (EHRA), a Registered Branch of the European Society of Cardiology (ESC), and the Heart Rhythm Society (HRS); in collaboration with the American College of Cardiology (ACC) and the American Heart Association (AHA)," *Europace* 11:771-817.
Alivisatos et al. (1996) "Semiconductor Clusters, Nanocrystals, and Quantum Dots," *Science* 271:933-937.
Alivisatos et al. (1998) "From Molecules to Materials: Current Trends and Future Directions," *Adv. Mater.* 10:1297-1336.
Allen et al. (Feb. 20, 2006) "Nanomaterial Transfer Using Hot Embossing for Flexible Electronic Devices," *Appl. Phys. Lett.* 88:083112.
Al-Sarawi et al. (Feb. 1998) "A Review of 3-D Packaging Technology," *IEEE Trans. Comp. Packag. Manufac. Technol. B* 21(1):2-14.
Altman et al. (2003) "Silk-Based Biomaterials," *Biomaterials* 24:401-416.
Amano et al. (Feb. 3, 1986) "Metalorganic Vapor Phase Epitaxial Growth of a High Quality GaN Film Using an AlN Buffer Layer," *Appl. Phys. Lett.* 48(5):353-355.
Ambrosy et al. (1996) "Silicon Motherboards for Multichannel Optical Modules," *IEEE Trans. Compon. Pack. A* 19:34-40.
Amir et al. (2000) "The Influence of Helium-Neon Irradiation on the Viability of Skin Flaps in the Rat," *Br. J. Plast. Surg.* 53:58-62.
Amsden et al. (Nov. 9, 2009) "Spectral Analysis of Induced Color Change on Periodically Nanopatterned Silk Films," *Opt. Express* 17(23):21271-21279.
Andersen et al. (2004) "Selecting the Signals for a Brain—Machine Interface," *Curr. Opin. Neurobiol.* 14:720-726.
Andersson et al. (Oct. 16, 2002) "Active Matrix Displays Based on All-Organic Electrochemical Smart Pixels Printed on Paper," *Adv. Mater.* 14:1460-1464.
Ando et al. (2004) "Self-Aligned Self-Assembly Process for Fabricating Organic Thin-Film Transistors," *Appl. Phys. Lett.* 85:1849-1851.
Angadi et al. (Web Release Jun. 1, 2006) "Thermal Transport and Grain Boundary Conductance in Ultrananocrystalline Diamond Thin Films," *J. Appl. Phys.* 99:114301.
Aoki et al. (2003) "Microassembly of Semiconductor Three Dimensional Photonic Crystals," *Nat. Mater.* 2:117-121.

(56) References Cited

OTHER PUBLICATIONS

Arnold et al. (2003) "Field-Effect Transistors Based on Single Semiconducting Oxide Nanobelts," *J. Phys. Chem. B* 107(3):659-663.
Ayón et al. (Jan. 1999) "Characterization of a Time Multiplexed Inductively Coupled Plasma Etcher," *J. Electrochem. Soc.* 146(1):339-349.
Baca et al. (2008) "Semiconductor Wires and Ribbons for High-Performance Flexible Electronics," *Angew. Chem. Int. Ed.* 47:5524-5542.
Bechtold et al. (Nov. 9, 2001) "Logic Circuits with Carbon Nanotube Transistors," *Science* 294:1317-1320.
Bae et al. (Jul. 1, 2002) "Single-Crystalline Gallium Nitride Nanobelts," *Appl. Phys. Lett.* 81(1):126-128.
Ball et al. (2004) "Towards an Implantable Brain-Machine Interface Based on Epicortical Field Potentials," *Biomed. Tech.* 49:756-759.
Balmer et al. (2005) "Diffusion of Alkanethiols in PDMS and Its Implications on Microcontact Printing (µCP)," *Langmuir* 21(2):622-632.
Banerjee et al. (May 2001) "3-D ICs: A Novel Chip Design for Improving Deep-Submicrometerinterconnect Performance and Systems-on-Chip Integration," *Proc. IEEE* 89(5):602-633.
Bao et al. (1997) "High-Performance Plastic Transistors Fabricated by Printing Techniques," *Chem. Mater.* 9:1299-1301.
Bao et al. (1999) "Printable Organic and Polymeric Semiconducting Materials and Devices," *J. Mater. Chem.* 9:1895-1904.
Barquins, M. (1992) "Adherence, Friction and Wear of Rubber-Like Materials," *Wear* 158:87-117.
Bates, F.S. (1991) "Polymer-Polymer Phase Behavior," *Science* 251:898-905.
Battaglia et al. (2003) "Colloidal Two-Dimensional Systems: CdSe Quantum Shells and Wells," Angew. Chem. Int. Ed. 442:5035-5039.
Bauer et al. (2004) "Biological Applications of High Aspect Ratio Nanoparticles," *J. Mater. Chem.* 14:517-526.
Berg et al. (2003) "Tailored Micropatterns Through Weak Polyelectrolyte Stamping," Langmuir 19:2231-2237.
Bernard et al. (1998) "Printing Patterns of Proteins," *Langmuir* 14(9):2225-2229.
Bett et al. (Aug. 1999) "III-V Compounds for Solar Cell Applications," *Appl. Phys. A. Mater. Sci.* 69(2):119-129.
Bhunia et al. (2004) "Free-Standing and Vertically Aligned InP Nanowires Grown by Metalorganic Vapor Phase Epitaxy," *Physica E* 21:583-587.
Bhushan et al. (Nov. 2004) "Multiwalled Carbon Nanotube AFM Probes for Surface Characterization of Micro/Nanostructures," *Microsyst. Technol.* 10(8-9):633-639.
Bietsch et al. (Oct. 1, 2000) "Conformal Contact and Pattern Stability of Stamps Used for Soft Lithography," *J. Appl. Phys.* 88(7):4310-4318.
Bishay et al. (2000) "Temperature Coefficient of the Surface Resistivity of Two-Dimensional Island Gold Films," *J. Phys. D. Appl. Phys.* 33(18):2218-2222.
Blanchet et al. (2003) "Large Area, High Resolution, Dry Printing of Conducting Polymers for Organic Electronics," *Appl. Phys. Lett.* 82:463-465.
Blanchet et al. (2003) "Printing Techniques for Plastic Electronics," *J. Imag. Sci. Tech.* 47(4):296-303.
Blazdell et al. (Nov. 1999) "Preparation of Ceramic Inks for Solid Freeforming Using a Continuous Jet Printer," *J. Mat. Syn. Process.* 7(6):349-356.
Boltau et al. (1998) "Surface-Induced Structure Formation of Polymer Blends on Patterned Substrates," *Nature* 391:877-879.
Boncheva et al. (Mar. 15, 2005) "Magnetic Self-Assembly of Three-Dimensional Surfaces from Planar Sheets," *Proc. Natl. Acad. Sci. USA* 102(11):3924-3929.
Boncheva et al. (Mar. 8, 2005) "Templated Self-Assembly: Formation of Folded Structures by Relaxation of Pre-Stressed, Planar Tapes," *Adv. Mater.* 17(5):553-557.
Bourzac, K. (May/Jun. 2010) "TR10: Implantable Electronics," *Technology Review*, Published by MIT, http://www.technologyreview.com/biomedicine/25086/?a=f.

Bowden et al. (1997) "Self Assembly of Mesoscale Objects into Ordered Two-Dimensional Arrays," *Science* 276:233-235.
Bowden et al. (1998) "Spontaneous Formation of Ordered Structures in Thin Films of Metals Supported on an Elastomeric Polymer," *Nature* 393:146-149.
Bowden et al. (2001) "Molecule-Mimetic Chemistry and Mesoscale Self-Assembly," *Acc. Chem. Res.* 34:231-238.
Bracher et al. (2009) "Shaped Films of Ionotropic Hydrogels Fabricated Using Templates of Patterns Paper," *Adv. Mater.* 21:445-450.
Bradley et al. (2003) "Flexible Nanotube Electronics," *Nano Lett.*, vol. 3, No. 10, pp. 1353-1355.
Braun et al. (1999) "Electrochemically Grown Photonic Crystals," *Nature* 402:603-604.
Britton et al. (Web Release Oct. 25, 2005) "Microstructural Defect Characterization of a Si:H Deposited by Low Temperature HW-CVD on Paper Substrates," *Thin Solid Films* 501(1-2):79-83.
Brown et al. (2005) "Evaluation of Polydimethylsiloxane Scaffolds with Physiologically-Relevant Elastic Moduli: Interplay of Substrate Mechanics and Surface Chemistry Effects on Vascular Smooth Muscle Cell Response," *Biomaterials* 26:3123-3129.
Brown et al. (Dec. 19, 2001) "Heterogeneous Materials Integration: Compliant Substrates to Active Device and Materials Packaging," *Mater. Sci. Eng. B* 87(3):317-322.
Brown, H.R. (1991) "The Adhesion Between Polymers," *Ann. Rev. Mater. Sci.* 21:463-489.
Bruschi et al. (2001) "Micromachined Silicon Suspended Wires With Submicrometric Dimensions," *Microelectron. Eng.* 57-58:959-965.
Buma et al. (2001) "High-Frequency Ultrasound Array Element Using Thermoelastic Expansion in an Elastomeric Film," *Appl. Phys. Lett.* 79:548-550.
Burdinski et al. (2005) "Single Etch Patterning of Stacked Silver and Molybdenum Alloy Layers on Glass Using Microcontact Wave Printing," *J. Am. Chem. Soc.* 127(31):10786-10787.
Burdinski, D. (non-dated) "Soft Lithography and Microcontact Wave Printing," http://www.research.philips.com/technologies/light_dev_microsys/softlitho/index.html, Downloaded May 23, 2007.
Burge et al. (Jun. 25, 1997) "X-Ray Holography for VLSI Using Synthetic Bilevel Holograms," *Proc. Int. Soc. Opt. Eng.* 3183:2-13.
Burgin et al. (2000) "Large Area Submicrometer Contact Printing Using a Contact Aligner," *Langmuir* 16:5371-5375.
Burns et al. (2003) "Printing of Polymer Thin-Film Transistors for Active-Matrix-Display Applications," *J. Soc. Inf. Display* 11:599-604.
Campbell et al. (2000) "Fabrication of Photonic Crystals for the Visible Spectrum by Holographic Lithography," *Nature* 404:53-56.
Cao et al. (2006) "Bilayer Organic-Inorganic Gate Dielectrics for High-Performance, Low-Voltage, Single-Walled Carbon Nanotube Thin-Film Transistors, Complementary Logic Gates, and p-n Diodes on Plastic Substrates," *Adv. Funct. Mater.* 16:2355-2362.
Cao et al. (2006) "Highly Bendable, Transparent Thin-Film Transistors That Use Carbon-Nanotube-Based Conductors and Semiconductors with Elastomeric Dielectrics," *Adv. Mater.* 18(3):304-309.
Cao et al. (2006) "Transparent flexible organic thin-film transistors that use printed single-walled carbon nanotube electrodes," *Applied Physics Letters* 88:113511.
Cao et al. (Jan. 5, 2009) "Ultrathin Films of Single-Walled Carbon Nanotubes for Electronics and Sensors: a Review of Fundamental and Applied Aspects," *Adv. Mater.* 21(1):29-53.
Cao et al. (Jul. 24, 2008) "Medium-Scale Carbon Nanotube Thin-Film Integrated Circuits on Flexible Plastic Substrates," *Nature* 454:495-500.
Carr et al. (1998) "Measurement of Nanomechanical Resonant Structures in Single-Crystal Silicon," *J. Vac. Sci. Technol. B* 16:3821-3824.
Chaudhury et al. (1991) "Direct Measurement of Interfacial Interactions Between Semispherical Lenses and Flat Sheets of Poly(dimethylsiloxane) and their Chemical Derivatives," *Langmuir* 7:1013-1025.
Chang et al. (1994) "Process Techniques," "Lithography," and "Device-Related Physics and Principles," In; *GaAs High-Speed Devices: Physics, Technology and Circuit Application*, John Wiley and Sons, New York, pp. 115-278.

(56) References Cited

OTHER PUBLICATIONS

Chen et al. (2003) "Characterization of Pd-GaAs Schottly Diodes Prepared by the Electrodes Plating Technique," *Semiconductor. Sci. Technol.* 18:620-626.

Chen et al. (2003) "Electronic Paper: Flexible Active-Matrix Electronics Ink Display," *Nature* 423:136.

Chen et al. (2005) "InGaN Nanorings and Nanodots by Selective Area Epitaxy," *Appl. Phys. Lett.* 87:143111.

Chen et al. (2005) "The Role of Metal-Nanotube Contact in the Performance of Carbon Nanotube Field-Effect Transistors," *Nano Lett.* 5(7):1497-1502.

Chen et al. (Feb. 27, 2006) "Complementary Carbon Nanotube-Gated Carbon Nanotube Thin-Fim Transistor," *Appl. Phys. Lett.* 88:093502.

Chen et al. (Jun. 2002) Effect of Process Parameters on the Surface Morphology and Mechanical Performance of Silicon Structures After Deep Reactive Ion Etching (DRIE) *J. Microelectromech. Syst.* 11(3):264-275.

Chen et al. (Mar. 2004) "A Family of Herringbone Patterns in Thin Films," *Scripta Materialia* 50(6):797-801.

Chen et al. (Mar. 24, 2006) "An Integrated Logic Circuit Assembled on a Single Carbon Nanotube," *Science* 311:1735.

Chen et al. (Sep. 2004) "Herringbone Buckling Patterns of Compressed Thin Films on Compliant Substrates," *J. Appl. Mech.* 71:597-603.

Cheng et al. (2005) "Ink-Jet Printing, Self-Assembled Polyelectrolytes, and Electroless Plating: Low Cost Fabrication of Circuits on a Flexible Substrate at Room Temperature," *Macromol. Rapid Commun.* 26:247-264.

Childs et al. (2002) "Decal Transfer Microlithography: A New Soft-Lithographic Patterning Method," *J. Am. Chem. Soc.* 124:13583-13596.

Childs et al. (2005) "Masterless Soft-Lithography: Patterning UV/Ozone-Induced Adhesion on Poly(dimethylsiloxane) Surfaces," *Langmuir* 21:10096-10105.

Childs et al. (Aug. 14, 2004) "Patterning of Thin-Film Microstructures on Non-Planar Substrate Surfaces Using Decal Transfer Lithography," *Adv. Mater.* 16(15):1323-1327.

Choi et al. (2007) "Biaxially Stretchable 'Wavy' Silicon Nanomembranes," *Nano Lett.* 7(6):1655-1663.

Choi et al. (Web Release Jan. 25, 2005) "Simple Detachment Patterning of Organic Layers and Its Applications to Organic Light-Emitting Diodes," *Adv. Mater.* 17(2):166-171.

Chou et al. (2004) "An Orientation-Controlled Pentacene Film Aligned by Photoaligned Polyimide for Organic Thin-Film Transistor Applications," *Adv. Func. Mater.* 14:811-815.

Chou et al. (Jun. 8, 1999) "Micromachining on (111)-Oriented Silicon," *Sens. Actuators A* 75(3):271-277.

Chu et al. (2005) "High-Performance Organic Thin-Film Transistors with Metal Oxide/Metal Bilayer Electrode," *Appl. Phys. Lett.* 87:193508.

Chung et al. (2000) Silicon Nanowire Devices *Appl. Phys. Lett.* 76(15):2068-2070.

Chung et al. (Jul. 1, 2003) "A Study on Formation of Al and $Al_2O_3$ on the Porous Paper by DC Magnetron Sputtering," *Surf. Coat. Technol.* 171(1-3):65-70.

Clerc, L. (1976) "Directional Differences of Impulse Spread in Trabecular Muscle from Mammalian Heart," *J. Physiol.* 255:335-346.

Cohen-Karni et al. (2009) "Flexible Electrical Recording from Cells Using Nanowire Transistor Arrays," *Proc. Natl. Acad. Sci. USA* 106:7309-7313.

Cole et al. (2008) "Patterned Growth and Transfer of ZnO Micro- and Nanocrystals with Size and Location Control," *Adv. Mater.* 20:1474-1478.

Collins et al. (Apr. 27, 2001) "Engineering Carbon Nanotubes and Nanotube Circuits Using Electrical Breakdown," *Science* 292:706-709.

Corazza et al. (2007) "Photobiomodulation on the Angiogenesis of Skin Wounds in Rats Using Different Light Sources," *Photomedicine Laser Surg.* 25:102-106.

Cox, H. L. (1952) "The Elasticity and Strength of Paper and Other Fibrous Materials," *Br. J. Appl. Phys.* 3:72-79.

Creagh et al. (2003) "Design and Performance of Inkjet Print Heads for Non-Graphic Arts Applications," *MRS Bull.* 28:807-811.

Crone et al. (Feb. 3, 2000) "Large-Scale Complementary Integrated Circuits Based on Organic Transistors," *Nature* 403:521-523.

Crowder et al. (1998) "Low-Temperature Single-Crystal Si TFTs Fabricated on Si Films Processed via Sequential Lateral Solidification," *IEEE Electron. Dev. Lett.* 19:306-308.

Cui et al. (2001) "Nanowire Nanosensors for Highly Sensitive and Selective Detection of Biological and Chemical Species," *Science* 293:1289-1292.

Dai et al. (2002) "Gallium Oxide Nanoribbons and Nanosheets," *J. Phys. Chem. B* 106(5):902-904.

Dai et al. (2003) "Novel Nanostructures of Functional Oxides Synthesized by Thermal Evaporation," *Adv. Funct. Mater.* 13:9-24.

Davidson et al. (2004) "Supercritical Fluid-Liquid-Solid Synthesis of Gallium Arsenide Nanowires Seeded by Alkanethiol-Stabilized Gold Nanocrystals," *Adv. Mater.* 16:646-649.

de Gans (2004) "Inkjet Printing of Polymers: State of the Art and Future Developments," *Adv. Mater.* 16(3):203-213.

De Sio et al. (Web Release May 18, 2005) "Electro-Optical Response of a Single-Crystal Diamond Ultraviolet Photoconductor in Transverse Configuration," *Appl. Phys. Lett.* 86:213504.

DeBoer et al. (2004) "Organic Single-Crystal Field-Effect Transistors," *Phys. Stat. Sol.* 201:1302-1331.

Deen et al. (2004) "Electrical Characterization of Polymer-Based FETs Fabricated by Spin-Coating Poly(3-alkylthiophene)s," *IEEE Trans. Electron Devices* 51:1892-1901.

Delmerche et al. (1997) "Stability of Molded Polydimethylsiloxane Microstructures," *Adv. Mat.* 9:741-746.

Deruelle et al. (1995) "Adhesion at the Solid-Elastomer Interface: Influence of Interfacial Chains," *Macromol.* 28:7419-7428.

Derycke et al. (Sep. 2001) "Carbon Nanotube Inter- and Intramolecular Logic Gates," *Nano Lett.* 1(9):453-456.

Desai et al. (Feb. 1999) "Nanopore Technology for Biomedical Applications," *Biomed. Microdevices* 2(1):11-40.

Dick et al. (Jun. 2004) "Synthesis of Branched 'Nanotrees' by Controlled Seeding of Multiple Branching Events," *Nat. Mater.* 3:380-384.

Dimroth et al. (Mar. 2007) "High Efficiency Multijunction Solar Cells," *MRS Bull.* 32:230-235.

Ding et al. (Oct. 4, 2004) "Self Catalysis and Phase Transformation in the Formation of CdSe Nanosaws," *Adv. Mater.* 16(19):1740-1743.

Dinsmore et al. (2002) "Colloidosomes: Selectively Permeable Capsules Composed of Colloidal Particles," *Science* 298:1006-1009.

Divliansky et al. (2003) "Fabrication of Three-Dimensional Polymer Photonic Crystal Structures Using Single Diffraction Element Interference Lithography," *Appl. Phys. Lett.* 82(11):1667-1669.

Dodabalapur A. (Apr. 2006) "Organic and Polymer Transistors for Electronics," *Mater Today* 9(4):24-30.

Dodabalapur et al. (1995) "Organic Transistors: Two-Dimensional Transport and Improved Electrical Characteristics," *Science* 268:270-271.

Duan et al. (2000) "General Synthesis of Compound Semiconductor Nanowires," *Adv. Mater.* 12(4):298-302.

Duan et al. (2003) "High-performance Thin-Film Transistors Using Semiconductor Nanowires and Nanoribbons," *Nature* 425:274-278.

Duan X, (2003) "Semiconductor Nanowires: From Nanoelectronics to Macroelectronics," Abstract from a presentation given at the 11th Foresight Conference on Molecular Nanotechnology, Oct. 10-20, Burlingame, CA.

Duboz et al. (1998) "Transistors and Detectors Based on GaN-Related Materials," In; *Group III Nitride Semiconductor Compounds*, Gill, B. ed., Clarendon, Oxford, pp. 343-387.

Duesberg et al. (2000) "Polarized Raman Spectroscopy on Isolated Single-Wall Carbon Nanotubes," *Phys. Rev. Lett.*, vol. 85, No. 25, pp. 5436-5439.

Duffy et al. (1998) "Rapid Prototyping of Microfluidic Systems in Poly(dimethylsiloxane)," *Anal. Chem.* 70:4974-4984.

(56) References Cited

OTHER PUBLICATIONS

Dupuis et al. (2008) "History, Development, and Applications of High-Brightness Visible Light-Emitting Diodes," *IEEE J. Lightwave Tech.* 26:1154-1171.

Durkop et al. (2004) "Extraordinary Mobility in Semiconducting Carbon Nanotube," *Nano Lett.* 4(1):35-39.

Eder et al. (Apr. 5, 2004) "Organic Electronics on Paper," *Appl. Phys. Lett.* 84(14):2673-2675.

Edrington et al. (2001) "Polymer-Based Photonic Crystals," *Adv. Mater.* 13:421-425.

Efimenko et al. (Oct. 15, 2002) "Surface Modification of Sylgard-184 Poly(dimethyl Siloxane) Networks by Ultraviolet and Ultraviolet/Ozone Treatment," *J. Colloid Interface Sci.* 254(2):306-315.

Eftekhari, G. (1993) "Variation in the Effective Richardson Constant of Metal—GaAs and Metal—InP Contacts Due to the Effect of Processing Parameters," *Phys. Status Solid A—Appl. Res.* 140:189-194.

Ensell, G. (1995) "Free Standing Single-Crystal Silicon Microstructures," *J. Micromech. Microeng.* 5:1-4.

Exam Report, Written Opinion and Response to Written Opinion, Corresponding to Singapore Patent Application No. 2007/18082-1, Mailed Beginning Jan. 15, 2009.

Examination Report and Response, Corresponding to Malaysian Patent Application No. PI 20062672, Mailed Aug. 28, 2009.

Examination Report, Corresponding to European Application No. EP 05 756 327.2, Dated Jan. 20, 2010.

Examination Report, Corresponding to Malaysian Patent Application No. PI 20092343, Mailed Jun. 15, 2010.

Examination Report, Corresponding to Malaysian Patent Publication No. PI 20052553, Mailed Mar. 13, 2009.

Examination Report, Corresponding to Singapore Patent Application No. 200608359-6, Completed on Aug. 27, 2008.

Examination Report, Response and Search Report, Corresponding to Malaysian Patent Application No. PI 20062537, Nov. 20, 2009.

Faez et al. (1999) "An Elastomeric Conductor Based on Polyaniline Prepared by Mechanical Mixing," *Polymer* 40:5497-5503.

Feigner et al. (1996) "Flexural Rigidity of Microtubules Measured with the Use of Optical Tweezers," *J. Cell Sci.* 109:509-516.

Fink et al. (1999) "Block Copolymers as Photonic Bandgap Materials," *J. Lightwave Tech.* 17:1963-1969.

Flewitt et al. (2005) "Low-Temperature Deposition of Hydrogenated Amorphous Silicon in an Electron Cyclotron Resonance Reactor for Flexible Displays," *Proc. IEEE* 93:1364-1373.

Folch et al. (1999) "Wafer-Level In-Registry Microstamping," *J. Microelectromech. Syst.* 8:85-89.

Forment et al. (2004) "Influence of Hydrogen Treatment and Annealing Processes Upon the Schottky Barrier Height of Au/n-GaAs and Ti/n-GaAs Diodes," *Semicond. Sci. Technol.* 19:1391-1396.

Forrest et al. (2004) "The Path to Ubiquitous and Low-Cost Organic Electronic Appliances on Plastic," *Nature* 428:911-918.

Fortunato et al. (2005) "Flexible a-Si: H Position-Sensitive Detectors," *Proc. IEEE* 93:1281-1286.

Fortunato et al. (Sep. 2008) "High-Performance Flexible Hybrid Field-Effect Transistors Based on Cellulose Fiber Paper," *IEEE Electron. Dev. Lett.* 29(9):988-990.

Freeman et al. (2000) "Spatial Spectral Analysis of Human Electrocardiograms Including the Alpha and Gamma Bands," *J. Neurosci. Methods* 95:111-121.

Freire et al. (1999) "Thermal Stability of Polyethylene Terephthalate (PET): Oligomer Distribution and Formation of Volatiles," *Packag. Technol. Sci.* 12:29-36.

Freund, L.B. (2000) "The Mechanics of Electronic Materials," *Int. J. Solids Struct.* 37:185-196.

Friedman et al. (2005) "High-Speed Integrated Nanowire Circuits," *Nature* 434:1085.

Fu et al. (Jan. 10, 2003) "Patterning of Diamond Microstructures on Si Substrate by Bulk and Surface Micromachining," *J. Mater. Process. Technol.* 132(1-3):73-81.

Furneaux et al. (1989) "The Formation of Controlled-Porosity Membranes from Anodically Oxidized Aluminum," *Nature* 337:147-149.

Gan et al. (2002) "Preparation of Thin-Film Transistors With Chemical Bath Deposited CdSe and CdS Thin Films," *IEEE Trans. Electron. Dev.* 49:15-18.

Gao et al. (Sep. 9, 2005) "Conversion of Zinc Oxide Nanobelts into Superlattice-Structures Nanohelices," *Science* 309:1700-1704.

Garcia et al. (2004) "Etchant Anisotropy Controls the Step Bunching Instability in KOH Etching of Silicon," *Phys. Rev. Lett.* 93(16):166102.

Gardner et al. (1965) "Physical Aspects of the Internal Water Relations of Plant Leaves," *Plant Physiol.* 40:705-710.

Garnier et al. (1994) "All-Polymer Field-Effect Transistor Realized by Printing Techniques," *Science* 265:1684-1686.

Geim et al. (Mar. 2007) "The Rise of Graphene," *Nature Mater.* 6:183-191.

Geissler et al. (2003) "Fabrication of Metal Nanowires Using Microcontact Printing," *Langmuir* 19(15):6301-6311.

Geissler et al. (Jun. 2003) "Selective Wet-Etching of Microcontact-Printed Cu Substrates with Control Over the Etch Profile," *Microelec. Eng.* 67-68:326-332.

Gelinck et al. (2000) "High-Performance All-Polymer Integrated Circuits," *Appl. Phys. Lett.* 77:1487-1489.

Gelinck et al. (2004) "Flexible Active-Matrix Displays and Shift Registers Based on Solution-Processed Organic Transistors," *Nat. Mater.* 3:106-110.

Georgakilas et al. (2002) "Wafer-Scale Integration of GaAs Optoelectronic Devices with Standard Si Integrated Circuits Using a Low-Temperature Bonding Procedure," *Appl. Phys. Lett.* 81:5099-5101.

Givargizov, E.I. (1991) "Applications," In; *Oriented Crystallization on Amorphous Substrates*, Plenum Press, New York, pp. 341-363.

Goetting et al. (1999) "Microcontact Printing of Alkanephosphonic Acids on Aluminum: Pattern Transfer by Wet Chemical Etching," *Langmuir* 15:1182-1191.

Goldman et al. (1996) "Correlation of Buffer Strain Relaxation Modes with Transport Properties of Two-Dimensional Electron Gases," *J. Appl. Phys.* 80:6849-6854.

Goldmann et al. (2004) "Hole Mobility in Organic Single Crystals Measured by a "Flip-Crystal" Field-Effect Technique," *J. Appl. Phys.* 96:2080-2086.

Goldsmith, T.H. (Sep. 1990) "Optimization, Constraint, and History in the Evolution of Eyes," *Quart. Rev. Biol.* 65(3):281-322.

Gratz et al. (1991) "Atomic Force Microscopy of Atomic-Scale Ledges and Etch Pits Formed During Dissolution of Quartz," *Science*, 251:1343-1346.

Gray et al. (Dec. 2001) "Screen Printed Organic Thin Film Transistors (OTFTs) on a Flexible Substrate," *Proc. SPIE* 4466:89-94.

Gray et al. (Mar. 5, 2004) "High-Conductivity Elastomeric Electronics," *Adv. Mater.* 16(5):393-397.

Grayson, T. (2002) "Curved Focal Plane Wide Field of View Telescope Design," *Proc. SPIE* 4849:269-274.

Gruen et al. (Mar. 21, 1994) "Fullerenes as Precursors for Diamond Film Growth Without Hydrogen or Oxygen Additions," *Appl. Phys. Lett.* 65(12):1502-1504.

Gudiksen et al. (Web Release Apr. 18, 2001) "Synthetic Control of the Diameter and Length of Single Crystal Semiconductor Nanowires," *J. Phys. Chem. B* 105:4062-4064.

Guo et al. (Aug. 19, 2002) "Metal-Insulator-Semiconductor Electrostatics of Carbon Nanotubes," *Appl. Phys. Lett.* 81(8):1486-1488.

Gur et al. (2005) "Air-Stable All-Inorganic Nanocrystal Solar Cells Processed from Solution," *Science* 310:462-465.

Gurbuz et al. (Jul. 2005) "Diamond Semiconductor Technology for RF Device Applications." *Solid State Electron.* 49(7):1055-1070.

Haisma et al. (2002) "Contact Bonding, Including Direct-Bonding in a Historical and Recent Context of Materials Science and Technology, Physics and Chemistry," *Mater. Sci Eng.* 37:1-60.

Halik et al. (2004) "Low-Voltage Organic Transistors with an Amorphous Molecular Gate Dielectric," *Nature* 431:963-966.

Hamedi et al. (May 2007) "Towards Woven Logic from Organic Electronic Fibres," *Nat. Mater.* 6:357-362.

Hamilton et al. (2004) "Field-Effect Mobility of Organic Polymer Thin-Film Transistors," *Chem. Mater.* 16:4699-4704.

(56) References Cited

OTHER PUBLICATIONS

Han et al. (2005) "Template-Free Directional Growth of Single-Walled Carbon Nanotues on a- and r-Plane Sapphire," *J. Am. Chem. Soc.* 127:5294-5295.

Harada et al. (2001) "Catalytic Amplification of the Soft Lithographic Patterning of Si. Nonelectrochemical Orthogonal Fabrication of Photoluminescent Porous Si Pixel Arrays," *J. Am. Chem. Soc.* 123:8709-8717.

Harkonen et al. (Jun. 8, 2006) "4 W Single-Transverse Mode VECSEL Utilizing Intra-Cavity Diamond Heat Spreader," *Electron Lett.* 42(12):693-694.

Hayase et al. (2001) "Photoangioplasty with Local Motexafin Lutetium Delivery Reduces Macrophages in a Rabbit Post-Balloon Injury Model," *Cardiovascular Res.* 49:449-455.

He et al. (2005) "Si Nanowire Bridges in Microtrenches: Integration of Growth into Device Fabrication," *Adv. Mater.* 17:2098-2102.

Heffelfinger et al. (1997) "Steps and the structure of the (0001) α-alumina surface," *Surf. Sci.*, 370:L168-L172.

Hillbrog et al. (Web Release Dec. 30, 2003) "Nanoscale Hydrophobic Recovery: A Chemical Force Microscopy Study of UV/Ozone-Treated Cross-Linker Poly(dimethylsiloxane)," *Langmuir* 20(3):785-794.

Hines et al. (2005) "Nanotransfer Printing of Organic and Carbon Nanotube Thin-Film Transistors on Plastic Substrates," *Appl. Phys. Lett.* 86:163101.

Hollenberg et al. (2006) "A MEMS Fabricated Flexible Electrode Array for Recording Surface Field Potentials," *J. Neurosci. Methods* 153:147-153.

Holmes et al. (Feb. 25, 2000) "Control of Thickness and Orientation of Solution-Grown Silicon Nanowires," *Science* 287:1471-1473.

Horan et al. (Jun. 2005) "In Vitro Degradation of Silk Fibroin," *Biomaterials* 26(17):3385-3393.

Horn et al. (1992) "Contact Electrification and Adhesion Between Dissimilar Materials," *Science* 256:362-364.

Hoyer, P. (1996) "Semiconductor Nanotube Formation by a Two-Step Template Process," *Adv. Mater.* 8:857-859.

Hsia et al. (2005) "Collapse of Stamps for Soft Lithography Due to Interfacial Adhesion," *Appl. Phys. Lett.* 86:154106.

Hsu et al. (2002) "Amorphous Si TFTs on Plastically Deformed Spherical Domes," *J. Non-Crystalline Solids* 299-302:1355-1359.

Hsu et al. (2003) "Nature of Electrical Contacts in a Metal—Molecule—Semiconductor System," *J. Vac. Sci. Technol. B* 21(4):1928-1935.

Hsu et al. (Jan. 15, 2004) "Spherical Deformation of Compliant Substrates with Semiconductor Device Islands," *J. Appl. Phys.* 95(2):705-712.

Hsu et al. (Mar. 2004) "Effects of Mechanical Strain on TFT's on Spherical Domes," *IEEE Trans. Electron Dev.* 51(3):371-377.

Hu et al. (1997) "Using Soft Lithography to Fabricate GaAs/AlGaAs Heterostructure Field Effect Transistors," *Appl. Phys. Lett.* 71:2020-2022.

Hu et al. (1999) Chemistry and Physics in One Dimension: Synthesis and Properties of Nanowires and Nanotubes, *Acc. Chem. Res.* 32:435-445.

Hu et al. (2004) "Percolation in Transparent and Conducting Carbon Nanotube Networks," *Nano Lett.*, vol. 4, No. 12, pp. 2513-2517.

Hu et al. (2009) "Highly Conductive Paper for Energy-Storage Devices," *Proc. Natl. Acad. Sci. USA* 106:21490-21494.

Hu et al. (2010) "Stretchable, Porous, and Conductive Energy Textiles," *Nano Lett.* 10:708-714.

Huang et al. (2001) "Directed Assembly of One-Dimensional Nanostructures into Functional Networks," *Science* 291:630-633.

Huang et al. (2001) "Room-Temperature Ultraviolet Nanowire Nanolasers," *Science* 292:1897-1899.

Huang et al. (2003) "Growth of Millimeter-Long and Horizontally Aligned Single-Walled Carbon Nanotubes on Flat Substrates," *J. Am. Chem. Soc.*, 125:5636-5637.

Huang et al. (2004) "Long and Oriented Single-Walled Carbon Nanotubes Grown by Ethanol Chemical Vapor Deposition," *J. Phys. Chem. B.* 108:16451-16456.

Huang et al. (2004) "Self-Organizing High-Density Single-Walled Carbon Nanotube Arrays from Surfactant Suspensions," *Nanotechnol.* 15:1450-1454.

Huang et al. (2005) "Nanomechanical Architecture of Strained Bilayer Thin Films: From Design Principles to Experimental Fabrication," *Adv. Mater.* 17(23):2860-2864.

Huang et al. (2005) "Nanowires for Integrated Multicolor Nanophotonics," *Small* 1(1):142-147.

Huang et al. (2005) "Nonlinear Analyses of Wrinkles in a Film Bonded to a Compliant Substrate," *J. Mech. Phys. Solids* 53:2101-2118.

Huang et al. (2005) "Stamp Collapse in Soft Lithography," *Langmuir* 21:8058-8068.

Huang et al. (Jan. 16, 2001) "Catalytic Growth of Zinc Oxide Nanowires by Vapor Transport," *Adv. Mater.* 13(2):113-116.

Huck et al. (2000) "Ordering of Spontaneously Formed Buckles on Planar Surfaces," *Langmuir* 16:3497-3501.

Huie, J.C. (2003) "Guided Molecular Self Assembly: A review of Recent Efforts," *Smart Mater. Struct.* 12:264-271.

Huitema et al. (2001) "Plastic Transistors in Active-Matrix Displays," *Nature* 414:599.

Hur et al. (2005) "Printed thin-film transistors and complementary logic gates that use polymer-coated single-walled carbon nanotube networks," *J. Appl. Phys.*, 98, 114302.

Hur et al. (2005) "Organic Nanodielectrics for Low Voltage Carbon Nanotube Thin Film Transistors and Complementary Logic Gates," *J. Am. Chem. Soc.* 127:13808-13809.

Hur et al. (Dec. 2004) "Nanotransfer Printing by Use of Noncovalent Surface Forces: Applications to Thin-Film Transistors that Use Single-Walled Carbon Nanotube Networks and Semiconducting Polymers," *Appl. Phys. Lett.* 85(23):5730-5732.

Hur et al. (Jun. 13, 2005) "Extreme Bendability of Single Walled Carbon Nanotube Networks Transferred From High-Temperature Growth Substrates to Plastic and Their Use in Thin-Film Transistors," *Appl. Phys. Lett.* 243502.

Hutchinson et al. (1992) "Mixed Mode Cracking in Layered Materials," *Adv. Appl. Mech.* 29:63-191.

Imparato et al. (2005) "Excimer Laser Induced Crystallization of Amorphous Silicon on Flexible Polymer Substrates," *Thin Solid Films* 487:58-62.

International Search Report and Written Opinion, Corresponding to International Application No. PCT/US2006/032125, Mailed Mar. 21, 2008.

International Search Report and Written Opinion, Corresponding to International Application No. PCT/US2009/058231, Mailed Nov. 17, 2009.

International Search Report and Written Opinion, Corresponding to International Application No. PCT/2005/014449, Mailed Jul. 3, 2008.

International Search Report and Written Opinion, Corresponding to International PCT Application No. PCT/US05/19354, Dated Apr. 18, 2007.

International Search Report and Written Opinion, Corresponding to International PCT Application No. PCT/US2007/079070, Mailed Apr. 23, 2008.

International Search Report and Written Opinion, Corresponding to International PCT Application No. PCT/US2007/077759, Mailed Apr. 11, 2008.

International Search Report and Written Opinion, Corresponding to International PCT Application No. PCT/US2007/022959, Mailed Oct. 14, 2008.

International Search Report and Written Opinion, Corresponding to International PCT Application No. PCT/US2006/021161, Mailed Feb. 28, 2008.

International Search Report and Written Opinion, Corresponding to International Application No. PCT/US2009/036192, Mailed Jul. 6, 2009.

International Search Report and Written Opinion, Corresponding to International Application No. PCT/US2010/034520, Mailed Sep. 24, 2010.

International Search Report and Written Opinion, Corresponding to International Application No. PCT/US07/74293, Mailed Jul. 24, 2008.

(56) References Cited

OTHER PUBLICATIONS

International Search Report and Written Opinion, Corresponding to International Application No. PCT/US07/82633, Mailed May 16, 2008.
International Search Report and Written Opinion, Corresponding to International Application No. PCT/US07/77217, Mailed Jun. 3, 2008.
International Search Report and Written Opinion, Corresponding to International Application No. PCT/US09/47442, Mailed Sep. 21, 2009.
International Search Report and Written Opinion, Corresponding to International Application No. PCT/US04/40192, Mailed Jul. 6, 2005.
International Search Report and Written Opinion, Corresponding to International Application no. PCT/US10/50468, Mailed Jan. 6, 2011.
International Search Report and Written Opinion, Corresponding to International Application no. PCT/US10/60425, Mailed May 25, 2011.
International Search Report and Written Opinion, Corresponding to International Application No. PCT/US2011/028094, Mailed Jul., 14, 2011.
International Search Report and Written Opinion, Corresponding to International Application No. PCT/US2010/042585, Mailed May 25, 2011.
International Search Report and Written Opinion, Corresponding to International Application No. PCT/US2010/024004, Mailed Nov. 26, 2010.
International Preliminary Report on Patentability, Corresponding to International Application No. PCT/2010/024004, Mailed Aug. 25, 2011.
Isberg et al. (Sep. 6, 2002) "High Carrier Mobility in Single-Crystal Plasma-Deposited Diamond," *Science* 297:1670-1672.
Islam et al. (Jan. 16, 2003) "High Weight Fraction Surfactant Solubilization of Single-Wall Carbon Nanotubes in Water," *Nano Lett.* 3(2):269-273.
Ismach et al. (2004) "Atomic-Step-Tem plated Formation of Single Wall Carbon Nanotube Patterns," *Angew. Chem. Int. Ed.* 43:6140-6143.
Itoh et al. (1991) "Cathodoluminescence Properties of Undoped and Zn-Doped $Al_xGa_{1-x}N$ Grown by Metalorganic Vapor Phase Epitaxy," *Jap. J. Appl. Phys.* 30:1604-1608.
Jabbour et al. (2001) "Screen Printing for the Fabrication of Organic Light-Emitting Devices," *IEEE J. Select. Top. Quantum. Electron.* 7:769-773.
Jackman et al. (Aug. 4, 1995) "Fabrication of Submicrometer Features on Curved Substrates by Microcontact Printing," *Science* 269:664-666.
Jacobs et al. (2001) "Submicrometer Patterning of Charge in Thin-Film Electrets," *Science* 291:1763-1766.
Jacobs et al. (2002) "Fabrication of a Cylindrical Display by Patterned Assembly," *Science* 296:323-325.
Jain et al. (2000) "III-Nitrides: Growth, Characterization, and Properties," *J. Appl. Phys.* 87:965-1006.
Jain et al. (2005) "Flexible Electronics and Displays: High-Resolution, Roll-to-Roll, Projection Lithography and Photoablation Processing Technologies for High-Throughput Production," *Proc. IEEE* 93:1500-1510.
James et al. (1998) "Patterned Protein Layers on Solid Substrates by This Stamp Microcontact Printing," *Langmuir* 14:742-744.
Jang et al. (2003) "Lateral Growth of Aligned Multiwalled Carbon Nanotubes Under Electric Fields," *Solid State Commun.* 126:305-308.
Jang et al. (2006) "Low-Voltage and High-Field-Effect Mobility Organic Transistors with a Polymer Insulator," *Appl. Phys. Lett.* 88:072101.
Javey et al. (2002) "High-κ Dielectrics for Advanced Carbon-Nanotube Transistors and Logic Gates," *Nature Mater.* 1:241-246.
Javey et al. (2005) "High Performance n-Type Carbon Nanotube Field-Effect Transistors with Chemically Doped Contacts," *Nano Lett.*, vol. 5, No. 2, pp. 345-348.
Javey et al. (Aug. 7, 2003) "Ballistic Carbon Nanotube Field-Effect Transistors," *Nature* 424:654-657.
Jenkins et al. (1994) "Gallium Arsenide Transistors: Realization Through a Molecularly Designed Insulator," *Science* 263:1751-1753.
Jeon et al. (1995) "Patterning of Dielectric Oxide Thin Layers by Microcontact Printing of Self-Assembled Monolayers," *J. Mater. Res.* 10:2996-2999.
Jeon et al. (2003) "Structural and Mechanical Properties of Woven Fabrics Employing Peirce's Model," *Textile Res. J.* 73:929-933.
Jeon et al. (2004) "Fabricating Complex Three-Dimensional Nanostructures with High Resolution Conformable Phase Masks," *Proc. Natl. Acad. Sci. USA* 101:12428-12433.
Jeon et al. (2004) "Three Dimensional Nanofabrication with Rubber Stamps and Conformable Photomasks," *Adv. Mater.* 16:593-600.
Jeon et al. (Aug. 4, 2004) "Three Dimensional Nanofabrication with Rubber Stamps and Conformable Photomasks," *Adv. Mater.* 16(15):1369-1375.
Jiang et al. (Oct. 2, 2007) "Finite Deformation Mechanics in Buckled Thin Films on Compliant Supports," *Proc. Natl. Acad. Sci. USA* 104(40):15607-15612.
Jiang et al. (1999) "Preparation of Macroporous Metal Films from Colloidal Crystals," *J. Am. Chem. Soc.* 121:7957-7958.
Jiang et al. (2002) "Polymer-on-Polymer Stamping: Universal Approaches to Chemically Patterned Surfaces," *Langmuir* 18:2607-2615.
Jiang et al. (2007) "Mechanical Properties of Robust Ultrathin Silk Fibroin Films," *Adv. Funct. Mater.* 17:2229-2237.
Jin et al. (2004) "Scalable Interconnection and Integration of Nanowire Devices Without Registration," *Nano Lett.* 4:915-919.
Jin et al. (2004) "Soft Lithographic Fabrication of an Image Sensor Array on a Curved Substrate," *J. Vac. Sci. Technol. B* 22(5):2548-2551.
Jin et al. (Aug. 2005) "Water-Stable Silk Films with Reduced β-Sheet Content," *Adv. Funct. Mater.* 15(8):1241-1247.
Jin et al. (Web Release Jan. 23, 2004) "Biomaterial Films of *Bombyx mori* Silk Fibroin with Poly(ethylene oxide)," *Biomacromolecules* 5(3):711-717.
Jiyun, C.H. (2003) "Guided Molecular Self-Assembly: A Review of Recent Efforts," *Smart Mater. Struct.* 12:264-271.
Joachim et al. (Nov. 30, 2000) "Electronics Using Hybrid-Molecular and Mono-Molecular Devices," *Nature* 408:541-548.
Johnson et al. (1999) "Ordered Mesoporous Polymers of Tunable Pore Size from Colloidal Silica Templates," *Science* 283:963-965.
Jones et al. (Jul./Aug. 2004) "Stretchable Wavy Metal Interconnects," *J. Vac. Sci. Technol. A* 22(4):1723-1725.
Joo et al. (2006) "Low-Temperature Solution-Phase Synthesis of Quantum Well Structures CdSe Nanoribbons," *J. Am. Chem. Soc.* 128(17):5632-5633.
Jortner et al. (2002) "Nanostructured Advanced Materials Perspectives and Directions," *Pure Appl. Chem.* 74(9):1491-1506.
Joselevich (2002) "Vectorial Growth of Metallic and Semiconducting Single-Wall Carbon Nanotubes," *Nano Lett.*, vol. 2, No. 10, pp. 1137-1141.
Kadish et al. (1988) "Interaction of Fiber Orientation and Direction of Impulse Propagation with Anatomic Barriers in Anisotropic Canine Myocardium," *Circulation.* 78:1478-1494.
Kagan (1999) "Organic-Inorganic Hybrid Materials as Semiconducting Channels in Thin-Film Field-Effect Transistors," *Science* 286:945-947.
Kagan et al. (2001) "Patterning Organic—Inorganic Thin-Film Transistors Using Microcontact Printed Templates," *Appl. Phys Lett.* 79(21):3536-3538.
Kagan et al. (2003) *Thin Film Transistors*, Dekker, New York, pp. 1-34.
Kane et al. (2000) "Analog and Digital Circuits Using Organic Thin-Film Transistors on Polyester Substrates," *IEEE Electron. Dev. Lett.* 21:534-536.
Kang et al. (2007) "Printed Multilayer Superstructures of Aligned Single-Walled Carbon Nanotubes for Electronic Applications," *Nano Lett.* 7(11):3343-3348.

(56) References Cited

OTHER PUBLICATIONS

Kang et al. (Apr. 2007) "High-Performance Electronics Using Dense, Perfectly Aligned Arrays of Single-Walled Carbon Nanotubes," *Nat. Nanotechnol.* 2(4):230-236.

Kar et al. (2005) "Controlled Synthesis and Photoluminescence Properties of ZnS Nanowires and Nanoribbons," *J. Phys. Chem. B* 109(8):3298-3302.

Kar et al. (2005) "Synthesis and Optical Properties of CdS Nanoribbons," *J. Phys. Chem B*. 109(41):19134-19138.

Kar et al. (2006) "Shape Selective Growth of CdS One-Dimensional Nanostructures by a Thermal Evaporation Process," *J. Phys. Chem. B*. 110(10):4542-4547.

Karnik et al. (2003) "Lateral Polysilicon $p^+$-p-$n^+$ and $p^+$-n-$n^+$ Diodes," *Solid-State Electronics* 47:653-659.

Karnik et al. (2003) "Multiple Lateral Polysilicon Diodes as Temperature Sensors for Chemical Microreaction Systems," *Jpn. J. Appl. Phys.* 42:1200-1205.

Kato et al. (2004) the Characteristic Improvement of Si(111) Metal-Oxide-Semiconductor Field-Effect Transistor by Long-Time Hydrogen Annealing, *Jpn. J. Appl. Phys*. 43(10):6848-6853.

Katz et al. (2001) "Synthetic Chemistry for Ultrapure, Processable, and High-Mobility Organic Transistor Semiconductors," *Acc. Chem. Res*. 34:359-369.

Katz, H.E. (2004) "Recent Advances in Semiconductor Performance and Printing Processes for Organic Transistor-Based Electronics," *Chem. Mater*. 16:4748-4756.

Kawata et al. (2001) "Finer Features for Functional Microdevices," *Nature* 412:697-698.

Kellis et al. (2009) "Human Neocortical Electrical Activity Recorded on Nonpenetrating Microwire Arrays: Applicability for Neuroprostheses," *Neurosurg. Focus* 27(1):E9.

Kendall, D.L. (1979) "Vertical Etching of Silicon at Very High Apect Ratios," *Ann. Rev. Mater. Sci*. 9:373-403.

Khakani et al. (2006) "Lateral Growth of Single Wall Carbon Nanotubes on Various Substrates by Means of an 'All-Laser' Synthesis Approach," *Diamond Relat. Mater*. 15:1064-1069.

Khan et al. (1993) "High Electron Mobility Transistor Based on a GaN-$Al_xGa_{1-x}N$ Heterojunction," *Appl. Phys. Lett*. 63:1214-1215.

Khang et al. (2006) "A Stretchable Form of Single-Crystal Silicon for High-Performance Electronics on Rubber Substrates," *Science* 311:208-212.

Kilby, J.S. (1976) "Invention of the Integrated Circuit," *IEEE Trans. Electron. Dev*. 23:648-654.

Kim et al. (2000) "Field Emission from Carbon Nanotubes for Displays," *Diamond and Related Mater*. 9(3-6):1184-1189.

Kim et al. (2002) "Nanolithography Based on Patterned Metal Transfer and Its Application to Organic Electronic Devices," *Appl. Phys. Lett*. 80:4051-4053.

Kim et al. (2003) "Epitaxial Self-Assembly of Block Copolymers on Lithographically Defined Nanopatterned Substrates," *Nature* 424:411-414.

Kim et al. (2008) "Stretchable Electronics: Materials Strategies and Devices," *Adv. Mater*. 20:4887-4892.

Kim et al. (2009) "Integrated Wireless Neural Interface Based on the Utah Electrode array," *Biomed. Microdevices* 11:453-466.

Kim et al. (2009) "Optimized Structural Designs for Stretchable Silicon Integrated Circuits," *Small* 5(24):2841-2847.

Kim et al. (Apr. 25, 2008) "Stretchable and Foldable Silicon Integrated Circuits," *Science* 320:507-511.

Kim et al. (Dec. 2, 2008) "Materials and Noncoplanar Mesh Designs for Integrated Circuits with Linear Elastic Responses to Extreme Mechanical Deformations," *Proc. Natl. Acad. Sci. USA* 105(48):18675-18680.

Kim et al. (Jan. 2008) "Complementary Logic Gates and Ring Oscillators Plastic Substrates by Use of Printed Ribbons Single-Crystalline Silicon," *IEEE Electron. Dev. Lett*. 29(1):73-76.

Kim et al. (Nov. 15, 1999) "Direct Observation of Electron Emission Site on Boron-Doped Polycrystalline Diamond Thin Films Using an Ultra-High-Vacuum Scanning Tunneling Microscope," *Appl. Phys. Lett*. 75(20):3219-3221.

Kim et al. (Oct. 17, 2010) "Waterproof AlIGaP optoelectronics on stretchable substrates with applications in biomedicine and robotics," *Nature Materials* 9:929-937.

Kim et al. (Oct. 2004) "Organic TFT Array on a Paper Substrate," *IEEE Electron. Dev. Lett*. 25(10):702-704.

Kim et al. (Web Release Apr. 18, 2010) "Dissolvable Films of Silk Fibroin for Ultrathin Conformal Bio-Integrated Electronics," *Nature Materials* 9:511-517.

Kim et al. (Web Release Feb. 29, 2008) "Highly Emissive Self-Assembled Organic Nanoparticles Having Dual Color Capacity for Targeted Immunofluorescence Labeling," *Adv. Mater*. 20(6):1117-1121.

Kim et al. (Web Release Jul. 31, 2008) "Complementary Metal Oxide Silicon Integrated Circuits Incorporating Monolithically Integrated Stretchable Wavy Interconnects," *Appl. Phys. Lett*. 93(4):044102.

Kim et al. (Web Release Jul. 6, 2009) "Ultrathin Silicon Circuits with Strain-Isolation Layers and Mesh Layouts for High-Performance Electronics on Fabric, Vinyl, Leather and Paper," *Adv. Mater*. 21(36):3703-3707.

Kim et al. (Web Release Sep. 29, 2009) "Silicon Electronics on Silk as a Path to Bioresorbable, Implantable Devices," *Appl. Phys. Lett*. 95:133701-133703.

Kim, Y.S. (Web Release Aug, 9, 2005) "Microheater-Integrated Single Gas Sensor Array Chip Fabricated on Flexible Polyimide Substrate," *Sens. Actuators B* 114(1):410-417.

Klauk et al. (2002) "High-Mobility Polymer Gate Dielectric Pentacene Thin Film Transistors," *J. Appl. Phys*. 92:5259-5263.

Klein-Wiele et al. (2003) "Fabrication of Periodic Nanostructures by Phase-Controlled Multiple-Beam Interference," *Appl. Phys. Lett*. 83(23):4707-4709.

Knipp et al. (2003) "Pentacine Thin Film Transistors on Inorganic Dielectrics: Morphology, Structural Properties, and Electronic Transport," *Appl. Phys. Lett*. 93:347-355.

Ko et al. (2006) "Bulk Quantities of Single-Crystal Silicon Micro-/Nanoribbons Generated from Bulk Wafers," *Nano Lett*. 6(10):2318-2324.

Ko et al. (2010) "Flexible Carbon Nanofiber Connectors with Anisotropic Adhesion Properties," *Small* 6:22-26.

Ko et al. (Aug. 7, 2008) "A Hemispherical Electronic Eye Camera Based on Compressible Silicon Optoelectronics," *Nature* 454:748-753.

Ko et al. (Web Release Oct. 28, 2009) "Curvilinear Electronics Formed Using Silicon Membrane Circuits and Elastomeric Transfer Elements," *Small* 5(23):2703-2709.

Kocabas et al. (2004) "Aligned Arrays of Single-Walled Carbon Nanotubes Generated from Random Networks by Orientationally Selective Laser Ablation," *Nano Lett*., vol. 4, No. 12, pp. 2421-2426.

Kocabas et al. (2005) "Guided Growth of Large-Scale, Horizontally Aligned Arrays of Single-Walled Carbon Nanotubes and Their Use in Thin-Film Transistors," *Small* 1(11):1110-1116.

Kocabas et al. (2006) "Large Area Aligned Arrays of SWNTs for High Performance Thin Film Transistors," American Physical Society, APS March Meeting, Mar. 13-17, Abstract # W31.004.

Kocabas et al. (2006) "Spatially Selective Guided Growth of High-Coverage Arrays and Random Networks of Single-Walled Carbon Nanotubes and Their Integration into Electronic Devices," *J. Am. Chem. Soc*. 128:4540-4541.

Kocabas et al. (2007) "Experimental and Theoretical Studies of Transport Through Large Scale, Partially Aligned Arrays of Single-Walled Carbon Nanotubes in Thin Film Type Transistors," *Nano Lett*. 7(5):1195-1202.

Kocabas et al. (Feb. 5, 2008) "Radio Frequency Analog Electronics Based on Carbon Nanotube Transistors," *Proc. Natl. Acad. Sci. USA* 105(5):1405-1409.

Kodambaka et al. (2006) "Control of Si Nanowire Growth by Oxygen," *Nano Lett*. 6(6):1292-1296.

Koide et al. (2000) "Patterned Luminescence of Organic Light-Emitting Diodes by Hot Microcontact Printing (HµCP) of Self-Assembled Monolayers," *J. Am. Chem. Soc*. 122:11266-11267.

Konagai et al. (1978) "High Efficiency GaAs Thin Film Solar Cells by Peeled Film Technology," *J. Cryst. Growth* 45:277-280.

Kong et al. (2004) "Single-Crystal Nanorings Formed by Epitaxial Self-Coating of Polar Nanobelts," *Science* 303:1348-1351.

(56) References Cited

OTHER PUBLICATIONS

Kong et al. (Jan. 28, 2000) "Nanotube Molecular Wires as Chemical Sensors," *Science* 287:622-625.
Kong et al. (Oct. 2003) "Structure of Indium Oxide Nanobelts," *Solid State Commun.* 128(1):1-4.
Kong et al. (Oct. 29, 1998) "Synthesis of Individual Single-Walled Carbon Nonotubes on Patterned Silicon Wafers," *Nature* 395:878-881.
Kudo et al. (Web Release Jun. 13, 2006) "A Flexible and Wearable Glucose Sensor Based on Functional Polymers with Soft-MEMS Techniques," *Biosens. Bioelectron.* 22:558-562.
Kulkarni et al. (2002) "Mesoscale Organization of Metal Nanocrystals," *Pure Appl. Chem* 74(9):1581-1591.
Kumar et al. (1993) "Features of Gold Having Micrometer to Centimeter Dimensions can be Formed Through a Combination of Stamping with an Elastomeric Stamp and an Alkanethiol "Ink" Followed by Chemical Etching," *Appl. Phys. Lett.* 63(4):2002-2004.
Kumar et al. (1994) "Patterning Self-Assembled Monolayers: Applications in Materials Science," *Langmuir* 10:1498-1511.
Kumar et al. (2002) "Thermally-Stable Low-Resistance Ti/Al/Mo/Au Multilayer Ohmic Contacts on n-GaN," *J. Appl. Phys.* 92:1712-1714.
Kumar et al. (2005) "Percolating in Finite Nanotube Networks," *Phys. Rev. Lett.*, 95, 066802.
Kuo et al. (1985) "Effect of Mismatch Strain on Band Gap in III-V Semiconductors," *J. Appl. Phys.* 57:5428-5432.
Kuykendall et al. (Aug. 2004) "Crystallographic Alignment of High Density Gallium Nitride Nanowire Arrays," *Nat. Mater.* 3:524-528.
Lacour et al. (2005) "Stretchable Interconnects for Elastic Electronic Surfaces," *Proc. IEEE* 93:1459-1467.
Lacour et al. (2010) "Flexible and Stretchable Micro-Electrodes for in Vitro and n Vivo Neural Interfaces," *Med. Biol. Eng. Comput.* 48:945-954.
Lacour et al. (Apr. 14, 2003) "Stretchable Gold Conductors on Elastomeric Substrates," *Appl. Phys. Lett.* 82(15):2404.
Lacour et al. (Apr. 2004) "Design and Performance of Thin Metal Film Interconnects for Skin-Like Electronic Circuits," *IEEE Electron. Dev. Lett.* 25(4):179-181.
Lacour et al. (Dec. 2004) "An Elastically Stretchable TFT Circuit," *IEEE Electron Dev. Lett.* 25(12):792-794.
Lacour et al. (Web Release Jul. 14, 2006) "Stiff Subcircuit Islands of Diamondlike Carbon for Stretchable Electronics," *J. Appl. Phys.* 100:014913.
Lacour et al. (Web Release May 16, 2006) "Mechanisms of Reversible Stretchability of Thin Metal Films on Elastomeric Substrates," *Appl. Phys. Lett.* 88:204103.
Laimer et al. (Mar. 1997) "Diamond Growth in a Direct-Current Low-Pressure Supersonic Plasmajet," *Diamond Relat. Mater.* 6:406-410.
Lambacher et al. (2004) "Electrical Imaging of Neuronal Activity by Multi-TransistorArray (MTA) Recording at 7.8 pm Resolution," *Appl. Phys. A* 79:1607-1611.
Landes et al. (2002) "Some Properties of Spherical and Rod-Shaped Semiconductor and Metal Nanocrystals," *Pure Appl. Chem.* 74(9):1675-1692.
Law et al. (2004) "Semiconductor Nanowires and Nanotubes," *Ann. Rev. Mater. Res.* 34:83-122.
Law et al. (Aug. 27, 2004) "Nanoribbon Waveguides for Subwavelength Photonics Integration," *Science* 305:1269-1273.
Lawrence et al. (2008) "Bioactive Silk Protein Biomaterial Systems for Optical Devices," *Biomacromolecules* 9:1214-1220.
Lay et al. (2004) "Simple Route to Large-Scale Ordered Arrays of Liquid-Deposited Carbon Nanotubes," *Nano Lett.*, vol. 4, No. 4, pp. 603-606.
Leclercq et al. (1998) "III-V Micromachined Devices for Microsystems," *Microelectronics J.* 29:613-619.
Lecomte et al. (Apr. 2006) "Degradation Mechanism of Diethylene Glycol Units in a Terephthalate Polymer," *Polym. Degrade. Stab.* 91(4):681-689.
Lee et al. (2000) "Thin Film Transistors for Displays on Plastic Substrates," *Solid State Electron.* 44:1431-1434.
Lee et al. (2003) "High-Performance Poly-Si TFTs on Plastic Substrates Using a Nano-Structured Separation Layer Approach," *IEEE Elec. Dev. Lett.* 24:19-21.
Lee et al. (2004) "Organic Light-Emitting Diodes Formed by Soft Contact Lamination," *Proc. Natl. Acad. Sci. USA* 101(2):429-433.
Lee et al. (2005) "A Printable Form of Single-Crystalline Gallium Nitride for Flexible Optoelectronic Systems," *Small* 1:1164-1168.
Lee et al. (2005) "Large-Area, Selective Transfer of Microstructured Silicon (µs-Si): A Printing-Based Approach to High-Performance Thin-Film Transistors Supported on Flexible Substrates," *Adv. Mater.* 17:2332-2336.
Lee et al. (2006) "Micron and Submicron Patterning of Polydimethylsiloxane Resists on Electronic Materials by Decal Transfer Lithography and Reactive Ion-Beam Etching: Application to the Fabrication of High-Mobility, Thin-Film Transistors," *Appl. Phys. Lett.* 100:084907/1-7.
Lee et al. (Apr. 2005) "Fabrication of Stable Metallic Patterns Embedded in Poly(dimethylsiloxane) and Model Applications in Non-Planar Electronic and Lab-ona-Chip Device Patterning," *Adv. Funct. Mater.* 15(4):557-566.
Lee et al. (Dec. 1999) "The Surface/Bulk Micromachining (SBM) Process: A New Method for Fabricating Released MEMS in Single Crystal Silicon," *J. Microelectromech. Syst.* 8(4):409-416.
Lee et al. (Feb. 2001) "Application of Carbon Nanotubes to Field Emission Displays," *Diamond and Related Mater.* 10(2):265-270.
Lee et al. (Feb. 2005) "Weave Patterned Organic Transistors on Fiber for E-Textiles," *IEEE Trans. Electron. Dev.* 52(2):269-275.
Leong et al. (2009) "Tetherless Thermobiochemicall Actuated Microgrippers," *Proc. Natl. Acad. Sci. USA* 106:703-709.
Létant et al. (Jun. 2003) "Functionalized Silicon Membranes for Selective Bio-Organisms Capture," *Nat. Mater.* 2:391-395.
Li et al. (2002) "High-Resolution Contact Printing with Dendrimers," *Nano Lett* 2(4):347-349.
Li et al. (2003) "Ultrathin Single-Crystalline-Silicon Cantilever Resonators: Fabrication Technology and Significant Specimen Size effect on Young's Modulus," *Appl. Phys. Lett.* 83:3081-3083.
Li et al. (2004) "Electrospinning of Nanofibers: Reinventing the Wheel," *Adv. Mater.* 16(14):1151-1170.
Li et al. (2006) "Catalyst-Assisted Formation of Nanocantilever Arrays on ZnS Nanoribbons by Post-Annealing Treatment," *J. Phys. Chem. B* 110(13):6759-6762.
Li et al. (Dec. 2005) "Compliant Thin Film Patterns of Stiff Materials as Platforms for Stretchable Electronics," *J. Mater. Res.* 20(12):3274-3277.
Li et al. (Jul. 1, 2002) "ZnO Nanobelts Grown on Si Substrate," *Appl. Phys. Lett.* 81:144-146.
Lieber, C. (2001) "The Incredible Shrinking Circuit," *Sci. Am.* 285(3):58-64.
Lieber, C.M. (2003) "Nanoscale Science and Technology: Building a Big Future from Small Things," *MRS Bull.* 28:486-491.
Lim et al. (2005) "Flexible Membrane Pressure Sensor," *Sens. Act. A* 119:332-335.
Lima et al. (2007) "Creating Micro- and Nanostructures on Tubular and Spherical Surfaces," *J. Vac. Sci. Technol. B* 25(6):2412-2418.
Lin et al. (Sep. 2005) "High-Performance Carbon Nanotube Field-Effect Transistor With Tunable Polarities," *IEEE Trans. Nano* 4(5):481-489.
Linder et al. (1994) "Fabrication Technology for Wafer Through-Hole Interconnections and Three-Dimensional Stacks of Chips and Wafers," *Proc. IEEE Micro. Electro Mech. Syst.* 349-354.
Ling et al. (2004) "Thin Film Deposition, Patterning, and Printing in Organic Thin Film Transistors," *Chem. Mater.* 16:4824-4840.
Liu et al. (1999) "Controlled deposition of individual single-walled carbon nanotubes on chemically functionalized templates," *Chem. Phys. Lett.*, 303:125-129.
Long et al. (1990) "Heterostructure FETs and Bipolar Transistors," In; *Gallium Arsenide Digital Integrated Circuit Design*, McGraw-Hill, New York, pp. 58-69.
Loo et al. (2002) "Additive, Nanoscale Patterning of Metal Films with a Stamp and A Surface Chemistry Mediated Transfer Process: Applications in Plastic Electronics," *Appl. Phys. Lett.* 81:562-564.

(56) References Cited

OTHER PUBLICATIONS

Loo et al. (2002) "High-Resolution Transfer Printing on GaAs Surfaces Using Alkane Dithiol Monolayers," *J. Vac. Sci. Technol. B* 20(6):2853-2856.
Loo et al. (2002) "Interfacial Chemistries for Nanoscale Transfer Printing," *J. Am. Chem. Soc.* 124:7654-7655.
Loo et al. (2002) "Soft, Conformable Electrical Contacts for Organic Semiconductors: High-Resolution Plastic Circuits by Lamination," *Proc. Natl. Acad. Sci. USA* 99(16):10252-10256.
Loo et al. (2003) "Electrical Contacts to Molecular Layers by Nanotransfer Printing," *Nano Lett.* 3(7):913-917.
Lopes et al. (Sep. 2004) "Thermal Conductivity of PET/(LDPE/Al) Composites Determined by MDSC," *Polym. Test.* 23(6):637-643.
Lu et al. (Apr. 2010) "Water-Insoluble Silk Films with Silk I Structure," *Acta Biomater.* 6(4):1380-1387.
Lu et al. (Dec. 2006) "Electronic Materials-Buckling Down for Flexible Electronics," *Nat. Nanotechnol.* 1:163-164.
Lu et al. (Jul. 19, 2005) "One Dimensional Hole Gas in Germanium/Silicon Nanowire Heterostructures," *Proc. Nat. Acad. Sci. USA* 102(29):10046-10051.
Lu et al. (Nov. 2008) "Nanowire Transistor Performance Limits and Applications," *IEEE Trans Electron Dev.* 55(11):2859-2876.
Luan et al. (1992) "An Experimental Study of the Source/Drain Parasitic Resistance Effects in Amorphous Silicon Thin Film Transistors," *J. Appl. Phys.* 72:766-772.
Ma et al. (2004) "Single-Crystal CdSe Nanosaws," *J. Am. Chem. Soc.* 126(3):708-709.
Mack et al. (2006) "Mechanically Flexible Thin-Film Transistors that Use Ultrathin Ribbons of Silicon Derived from Bulk Wafers," *Appl. Phys. Lett.* 88:213101.
Madou, M. (1997) "Etch-Stop Techniques," In; *Fundamentals of Microfabrication*, CRC Press, New York, pp. 193-199.
Maikap et al. (2004) "Mechanically Strained-Si NMOSFETs," *IEEE Electron. Dev. Lett.* 25:40-42.
Maldovan et al. (2004) "Diamond-Structured Photonic Crystals," *Nature Materials* 3:593-600.
Mandlik et al. (Aug. 2006) "Fully Elastic Interconnects on Nanopatterned Elastomeric Substrates," *IEEE Electron Dev. Lett.* 27(8):650-652.
Manna et al. (Web Release May 25, 2003) "Controlled Growth of Tetrapod-Branched Inorganic Nanocrystals," *Nat. Mater.* 2:382-385.
Markovich et al. (1999) "Architectonic Quantum Dot Solids," *Acc. Chem. Res.* 32:415-423.
Marquette et al. (2004) "Conducting Elastomer Surface Texturing: A Path to Electrode Spotting Application to the Biochip Production," *Biosens. Bioelectron.* 20:197-203.
Martensson et al. (2004) "Nanowire Arrays Defined by Nanoimprint Lithography," *Nano Lett.* 4:699-702.
Martin, C.R. (1995) "Template Synthesis of Electronically Conductive Polymer Nanostructures," *Acc. Chem. Res.* 28:61-68.
Mas-Torrent et al. (2006) "Large Photoresponsivity in High-Mobility Single-Crystal Organic Field-Effect Phototransistors," *ChemPhysChem* 7:86-88.
Masuda et al. (2000) "Fabrication of Ordered Diamonds/Metal Nanocomposite Structures," *Chem. Lett.* 10:1112-1113.
Matsunaga et al. (2003) "An Improved GaAs Device Model for the Simulation of Analog Integrated Circuit," *IEEE Trans. Elect. Dev.* 50:1194-1199.
McAlpine et al. (2003) "High-Performance Nanowire Electronics and Photonics on Glass and Plastic Substrates," *Nano Lett.* 3:1531-1535.
McAlpine et al. (2005) "High-Performance Nanowire Electronics and Photonics and Nanoscale Patterning on Flexible Plastic Substrates," *Proc. IEEE* 93:1357-1363.
McCaldin et al. (1971) "Diffusivity and Solubility of Si in the Al Metallization of Integrated Circuits," *Appl. Phys. Lett.* 19:524-517.
Mehring C. et al. (2003) Inference of hand movements from local field potentials in monkey motor cortex. *Nature Neurosci.* 6, 1253-1254.

Meisel et al. (2004) "Three-Dimensional Photonic Crystals by Holographic Lithography Using the Umbrella Configuration: Symmetries and Complete Photonic Band Gaps," *Phys. Rev. B.* 70:165101:1-10.
Meitl et al. (2004) "Solution Casting and Transfer Printing Single-Walled Carbon Nanotube Films," *Nano Lett.* 4:1643-1647.
Meitl et al. (2006) "Transfer Printing by Kinetic Control of Adhesion to an Elastomeric Stamp," *Nat. Mater.* 5:33-38.
Meitl et al. (Web Release Feb. 22, 2007) "Stress Focusing for Controlled Fracture in Microelectromechanical Systems," *Appl. Phys. Lett.* 90:083110.
Melosh et al. (2003) "Ultrahigh-Density Nanowire Lattices and Circuits," *Science* 300:112-115.
Menard et al. (2004) "A Printable Form of Silicon for High Performance Thin Film Transistors on Plastic Substrates," *Appl. Phys. Lett.* 84:5398-5400.
Menard et al. (2004) "Improved Surface Chemistries, Thin Film Deposition Techniques, and Stamp Designs for Nanotransfer Printing," *Langmuir* 20:6871-6878.
Menard et al. (2004) "High-Performance n- and p-Type Single-Crystal Organic Transistors with Free-Space Gate Dielectrics," *Adv. Mat.* 16:2097-2101.
Menard et al. (2005) "Bendable Single Crystal Silicon Thin Film Transistors Formed by Printing on Plastic Substrates," *Appl. Phys. Lett.* 86(093507):1-3.
Menard et al. (2007) Micro- and Nanopatterning Techniques for Organic Electronic and Optoelectronic Systems, *Chem. Rev.* 107:1117-1160.
Miao et al. (2003) "Micromachining of Three-Dimensional GaAs Membrane Structures Using High-Energy Nitrogen Implantation," *J. Micromech. Microeng.* 13:35-39.
Michalske et al. (1985) "Closure and Repropagation of Healed Cracks in Silicate Glass," *J. Am. Ceram. Soc.* 68:586-590.
Michel et al. (2001) Printing Meets Lithography: Soft Approaches to High-Resolution Printing, *IBM J. Res. Dev.* 45:697-719.
Miller et al. (2002) "Direct Printing of Polymer Microstructures on Flat and Spherical Surfaces Using a Letterpress Technique," *J. Vac. Sci. Technol. B* 20(6):2320-2327.
Milliron et al. (2004) "Colloidal Nanocrystal Heterostructures with Linear and Branched Topology," *Nature* 430:190-195.
Min, G. (Apr. 4, 2003) "Plastic Electronics and Their Packaging Technologies," *Syn. Metals.* 135:141-143.
Minev et al. (2010) "Impedance Spectroscopy on Stretchable Microelectrode Arrays," *Appl. Phys. Lett.* 97:043707.
Mirkin et al. (2001) "Emerging Methods for Micro- and Nanofabrication," *MRS Bulletin* 26(7):506-507.
Misewich et al. (May 2, 2003) "Electronically Induced Optical Emission from a Carbon Nanotube FET," *Science* 300:783-786.
Mishra et al. (2002) "AlGaN/GaN HEMTs—an Overview of Device Operation and Applications," *Proc. IEEE* 90:1022-1031.
Mitzi et al. (2004) "High-Mobility Ultrathin Semiconducting Films Prepared by Spin Coating," *Nature* 428:299-303.
Moon et al. (2002) "Ink-Jet Printing of Binders for Ceramic Components," *J. Am. Ceram. Soc.* 85:755-762.
Moore et al. (Sep. 9, 2003) "Individually Suspended Single-Walled Carbon Nanotubes in Various Surfactants," *Nano Lett.* 3(10):1379-1382.
Morales et al. (Jan. 9, 1998) "A Laser Ablation Method for the Synthesis of Crystalline Semiconductor Nanowires," *Science* 279:208-211.
Morent et al. (2007) "Adhesion Enhancement by a Dielectric Barrier Discharge of PDMS used for Flexible and Stretchable Electronics," *J. Phys. D. Appl. Phys.* 40:7392-7401.
Mori et al. (1978) "A New Etching Solution System, $H_3PO_4$-$H_2O_2$-$H_2O$, for GaAs and Its Kinetics," *J. Electrochem. Soc.* 125:1510-1514.
Morkoc et al. (1995) "High-Luminosity Blue and Blue-Green Gallium Nitride Light-Emitting Diodes," *Science* 267:51-55.
Morkved et al. (1994) "Mesoscopic Self-Assembly of Gold Islands on Diblock-Copolymer Films," *Appl. Phys. Lett.* 64:422-424.
Morra et al. (1990) "On the Aging of Oxygen Plasma-Treated Polydimthylsiloxane Surfaces," *J. Colloid Interface Sci.* 137:11-24.

(56) References Cited

OTHER PUBLICATIONS

Murakami et al. (2005) "Polarization Dependence of the Optical Absorption of Single-Walled Carbon Nanotubes," *Phys. Rev. Lett.*, 94, 087402.
Murphy et al. (2008) "Modification of Silk Fibroin Using Diazonium Coupling Chemistry and the Effects on hMSC Proliferation and Differentiation," *Biomaterials* 29:2829-2838.
Namazu et al. (2000) "Evaluation of Size Effect on Mechanical Properties of Single Crystal Silicon by Nanoscale Bending Test Using AFM," *J. MEMS* 9:450-459.
Nath et al. (2002) "Nanotubes of the Disulfides of Groups 4 and 5 Metals," *Pure Appl. Chem.* 74(9):1545-1552.
Nathan et al. (2000) "Amorphous Silicon Detector and Thin Film Transistor Technology for Large-Area Imaging of X-Rays," *Microelectron J.* 31:883-891.
Nathan et al. (2002) "Amorphous Silicon Technology for Large Area Digital X-Ray and Optical Imaging," *Microelectronics Reliability* 42:735-746.
Newman et al. (2004) "Introduction to Organic Thin Film Transistors and Design of n-Channel Organic Semiconductors," *Chem. Mater.* 16:4436-4451.
Nirmal et al. (1999) "Luminescence Photophysics in Semiconductor Nanocrystals," *Acc. Chem. Res.* 32:407-414.
Noda et al. (1996) "New Realization Method for Three-Dimensional Photonic Crystal in Optical Wavelength Region," *Jpn. J. Appl. Phys.* 35:L909-L912.
Nomura et al. (2004) "Room-Temperature Fabrication of Transparent Flexible Thin-Film Transistors Using Oxide Semiconductors," *Nature* 432:488-492.
Novoselov et al. (Oct. 22, 2004) "Electric Field Effect in Atomically Thin Carbon Films," *Science* 306:666-669.
O'Connell et al. (Jul. 26, 2002) "Bang Gap Fluorescence from Individual Single-Walled Carbon Nanotubes," *Science* 297:593-596.
O'Riordan et al. (2004) "Field Configured Assembly: Programmed Manipulation and Self-Assembly at the Mesoscale," *Nano Lett.* 4:761-765.
Odom et al. (2002) "Improved Pattern Transfer in Soft Lithography Using Composite Stamps," *Langmuir* 18(13):5314-5320.
Office Action and Response, Corresponding to Malaysian Patent Publication No. PI 20052553, Mailed Mar. 13, 2009 and Dec. 8, 2009.
Office Action and Response, Corresponding to U.S. Appl. No. 11/423,287, Mailed Feb. 13, 2008.
Office Action and Response, Corresponding to U.S. Appl. No. 11/421,654, Mailed Sep. 29, 2009.
Office Action and Response, Corresponding to U.S. Appl. No. 11/858,788, Mailed Beginning Jan. 28, 2011.
Office Action Corresponding to Chinese Patent Application No. 200780049982.1, Issued May 12, 2010.
Office action Corresponding to Korean Patent Application No. 10-2006-7010632, Completed Nov. 22, 2007.
Office Action Corresponding to U.S. Appl. No. 11/851,182, Mailed Apr. 1, 2010.
Office Action, Corresponding to Chinese Patent Application No. 200780048002.6, Issued Apr. 13, 2010.
Office Action, Corresponding to Chinese Patent Application No. 200580013574.1, Issued May 11, 2010.
Office Action, Corresponding to Taiwan Patent Application No. 095121212, Issued May 7, 2010.
Office Action, Corresponding to U.S. Appl. No. 11/981,380, Mailed Sep. 23, 2010.
Office Actions and Responses, Corresponding to U.S. Appl. No. 11/145,542, Mailed between Apr. 5, 2007 and Dec. 23, 2008.
Office Actions and Responses, Corresponding to U.S. Appl. No. 11/981,380, Mailed Beginning Sep. 23, 2010.
Office Actions Corresponding to Chinese Patent Application No. 200480035731.4, Issued Mar. 27, 2009 and Dec. 3, 2010.
Office Actions, Corresponding to Chinese Patent Application No. 200580018159.5, Issued Jan. 23, 2009 and Feb. 12, 2010.
Office Action, Corresponding to U.S. Appl. No. 12/513,387, Mailed May 10, 2011.
Ohzono et al. (2004) "Ordering of Microwrinkle Patterns by Compressive Strain," *Phys. Rev. B* 69(13):132202.
Ohzono et al. (Web Release Jul. 7, 2005) "Geometry-Dependent Stripe Rearrangement Processes Induced by Strain on Preordered Microwrinkle Patterns," *Langmuir* 21(16):7230-7237.
Omenetto et al. (2008) "A New Route for Silk," *Nature Photon.* 2:641-643.
Ong et al. (2004) "High-Performance Semiconducting Polythiophenes for Organic Thin-Film Transistors," *J. Am. Chem. Soc.* 126:3378-3379.
Ong et al. (2005) "Design of High-Performance Regioregular Polythiophenes for Organic Thin-Film Transistors," *Proc. IEEE* 93:1412-1419.
Origin Energy (May 2004) "Fact Sheet—Sliver Cells," www.orginenergy.com.au/sliver.
Ouyang et al. (2002) "High-Performance, Flexible Polymer Light-Emitting Diodes Fabricated by a Continuous Polymer Coating Process," *Adv. Mat.* 14:915-918.
Ouyang et al. (2008) "High Frequency Properties of Electro-Textiles for Wearable Antenna Applications," *IEEE Trans. Antennas Propag.* 56(2):381-389.
Ouyang et al. (Web Release Mar. 20, 2000) "Conversion of Some Siloxane Polymers to Silicon Oxide by UV/Ozone Photochemical Processes," *Chem. Mater.* 12(6):1591-1596.
Overholt et al. (2005) "Photodynamic Therapy for Esophageal Cancer using a 180° Windowed Esophageal Balloon," *Lasers in Surg. Med.* 14:27-33.
Pan et al. (2001) "Nanobelts of Semiconducting Oxides," *Science* 291:1947-1949.
Panev et al. (2003) "Sharp Excitation from Single InAs Quantum Dots in GaAs Nanowires," *Appl. Phys. Lett.* 83:2238-2240.
Pardo et al. (2000) "Application of Screen Printing in the Fabrication of Organic Light-Emitting Devices," *Adv. Mater.* 12(17):1249-1252.
Park et al. (1997) "Block Copolymer Lithography: Periodic Arrays of $\sim 10^{11}$ Holes in 1 Square Centimeter," *Science* 276:1401-1404.
Park et al. (1998) "Fabrication of Three-Dimensional Macroporous Membranes with Assemblies of Microspheres as Templates," *Chem. Mater.* 10:1745-1747.
Park et al. (Aug. 2009) "Printed Assemblies of Inorganic Light-Emitting Diodes for Deformable and Semitransparent Displays," *Science* 325:977-981.
Park et al. (Web Release Feb. 22, 2009) "Biodegradable Luminescent Porous Silicon Nanoparticles for in Vivo Applications," *Nature Mater.* 8:331-336.
Parker et al. (2009) "Biocompatible Silk Printed Optical Waveguides," *Adv. Mater.* 21:2411-2415.
Patolsky et al. (2006) "Stimulation, and Inhibition of Neuronal Signals with High-Density Nanowire Transistor Arrays," *Science* 313:1100-1104.
Patton et al. (Mar. 1998) "Effect of Diamondlike Carbon Coating and Surface Topography on the Performance of Metal Evaporated Magnetic Tapes," *IEEE Trans Magn.* 34(2):575-587.
Paul et al. (Apr. 2003) "Patterning Spherical Surfaces at the Two Hundred Nanometer Scale Using Soft Lithography," *Adv. Func. Mater.* 13(4):259-263.
Pearton et al. (1999) "GaN: Processing, Defects, and Devices," *J. Appl. Phys.* 86:1-78.
Peng et al. (Mar. 2, 2000) "Shape Control of CdSe Nanocrystals," *Nature* 404:59-61.
Piazza et al. (2005) "Protective Diamond-Like Carbon Coatings for Future Optical Storage Disks," *Diamond Relat. Mater.* 14:994-999.
Pimparkar et al. (Feb. 2007) "Current-Voltage Characteristics of Long-Channel Nanobundle Thin-Film Transistors: A 'Bottom-Up' Perspective," *IEEE Electron Dev. Lett.* 28(2):157-160.
Podzorov et al. (2005) "Hall Effect in the Accumulation Layers on the Surface of Organic Semiconductors," *Phys. Rev. lett.* 95:226601.
Pushpa et al. (2002) "Stars and Stripes. Nanoscale Misfit Dislocation Patterns on Surfaces," *Pure Appl. Chem.* 74(9):1663-1671.
Qian et al. (2006) "Scaling Effects of Wet Adhesion in Biological Attachment Systems," *Acta Biomaterialia* 2:51-58.

(56) References Cited

OTHER PUBLICATIONS

Quake et al (2000) "From Micro- to Nanofabrication with Soft Materials," *Science* 290:1536-1540.
Radtke et al. (Feb. 5, 2007) "Laser-Lithography on Non-Planar Surfaces," *Opt. Exp.* 15(3):1167-1174.
Raman et al. (1989) "Study of Mesa Undercuts Produced in GaAs with $H_3PO_4$-Based Etchants," *J. Electrochem. Soc.* 136:2405-2410.
Randall et al. (2005) "Permeation-driven flow in poly(dimethylsiloxane) microfluidic devices," *Proc. Nat. Acad. Sci. USA* 102(31):10813-10818.
Rao et al. (2003) "Large-scale assembly of carbon nanotubes," *Nature*, 425:36-37.
Razavi et al. (2009) "Three Dimensional Nanopillar Array Photovoltaics on Low Cost and Flexible Substrates," *Nature Materials* 8:648-653.
Razeghi et al. (1994) "High-Power Laser Diode Based on InGaAsP Alloys," *Nature* 369:631-633.
Razouk et al. (Sep. 1979) "Dependence of Interface State Density on Silicon Thermal Oxidation Process Variables," *J. Electrochem. Soc.* 126(9):1573-1581.
Reuss et al. (Jul. 2005) "Macroelectronics: Perspectives on Technology and Applications," *Proc. IEEE* 93(7):1239-1256.
Reuss et al. (Jun. 2006) "Macroelectronics," *MRS Bull.* 31:447-454.
Ribas et al. (1998) "Bulk Micromachining Characterization of 1.2 μm HEMT MMIC Technology for GaAs MEMS Design," *Mater. Sci. Eng. B* 51:267-273.
Ridley et al. (1999) "All-Inorganic Field Effect Transistors Fabricated by Printing," *Science* 286:746-749.
Roberts et al. (1979) "Looking at Rubber Adhesion," *Rubber Chem. Technol.* 52:2342.
Roberts et al. (Mar. 2006) "Elastically Relaxed Free-Standing Strained-Silicon Nanomembranes," *Nat. Mater.* 5:388-393.
Robinson et al. (1983) "GaAs Readied for High-Speed Microcircuits," *Science* 219:275-277.
Roelkens et al. (Dec. 2005) "Integration of InP/InGaAsP Photodetectors onto Siliconon-Insulator Waveguide Circuits," *Optics Express* 13(25):10102-10108.
Rogers et al. (1997) "Using an Elastomeric Phase Mask for Sub-100 nm Photolithography in the Optical Near Field," *Appl. Phys. Lett.* 70:2658-2660.
Rogers et al. (1998) "Generating ~90 Nanometer Features Using Near Field Contact Mode Photolithography with an Elastomeric Phase Mask," *J. Vac. Sci. Technol.* 16(1):59-68.
Rogers et al. (1998) "Quantifying Distortions in Soft Lithography," *J. Vac. Sci. Technol.* 16:88-97.
Rogers et al. (1998) "Using Printing and Molding Techniques to Produce Distributed Feedback and Bragg Reflector Resonators for Plastic Lasers," *Appl. Phys. Lett.* 73:1766-1768.
Rogers et al. (1999) Printing Process Suitable for Reel-to-Reel Production of High-Performance Organic Transistors and Circuits, *Adv. Mater.* 11(9):741-745.
Rogers et al. (2002) "Paper-Like Electronic Displays: Large-Area Rubber-Stamped Plastic Sheets of Electronics and Microencapsulated Electrophoretic Inks," *Proc. Nat. Acad. Sci. USA* 98:4835-4840.
Rogers et al. (2002) "Printed Plastic Electronics and Paperlike Displays," *J. Polym. Sci. Part A. Polym. Chem.* 40:3327-3334.
Rogers et al. (Mar. 2000) "Organic Smart Pixels and Complementary Inverter Circuits Formed on Plastic Substrates by Casting and Rubber Stamping," *IEEE Electron Dev. Lett.* 21(3):100-103.
Rogers, J.A. (2001) "Rubber Stamping for Plastic Electronics and Fiber Optics," *MRS Bulletin* 26(7):530-534.
Rogers, J.A. (2001) "Toward Paperlike Displays," *Science* 291:1502-1503.
Rosenblatt et al. (2002) "High Performance Electrolyte Gated Carbon Nanotube Transistors," *Nano Lett.* 2(8):869-872.
Rotkin et al. (2003) "Universal Description of Channel Conductivity for Nanotube and Nanowire Transistors," *Appl. Phys. Lett.* 83:1623-1625.
Roundy et al. (2003) "Photonic Crystal Structure with Square Symmetry within Each Layer and a Three-Dimensional Band Gap," *Appl. Phys Lett*. 82:3835-3837.
Rubehn et al. (2009) "A MEMS based Flexible Multichannel ECoG-Electrode Array," *J. Neural Eng.* 6:036003.
Ruchehoeft et al. (2000) "Optimal Strategy for Controlling Linewidth on Spherical Focal Surface Arrays," *J. Vac. Sci. Technol. B* 18(6):3185-3189.
Ryu et al. (2009) "Human Cortical Prostheses: Lost in Translation?" *Neurosurg Focus* 27(1):E5.
Samuelson et al. (2004) "Semiconductor Nanowires for Novel One-Dimensional Devices," *Physica E* 21:560-567.
Sangwal et al. (1997) "Nature of multilayer steps on the {100} cleavage planes of MgO single crystals," *Surf. Sci.*, 383:78-87.
Santin et al. (1999) "In vitro Evaluation of the Inflammatory Potential of the Silk Fibroin," *J. Biomed. Mater. Res.* 46:382-389.
Sanyal et al. (2002) "Morphology of Nanostructured Materials," *Pure Appl. Chem.* 74(9):1553-1570.
Sazonov et al. (2005) "Low-Temperature Materials and Thin-Film Transistors for Flexible Electronics," *Proc. IEEE* 93:1420-1428.
Scherlag et al. (1969) "Catheter Technique for Recording His Bundle Activity in Man," *Circulation* 39:13-18.
Schermer et al. (Web Release Apr. 28, 2005) "Thin-Film GaAs Epitaxial Lift-Off Solar Cells for Space Applications," *Prog. Photovoltaics: Res. Applic.* 13:587-596.
Schermer et al. (Web Release Jan. 19, 2006) "Photon Confinement in High-Efficiency, Thin-Film III-V Solar Cells Obtained by Epitaxial Lift-Off," *Thin Solid Films*511-512:645-653.
Schindl et al. (2003) "Direct Stimulatory Effect of Low-Intensity 670-nm Laser Irradiation on Human Endothelial Cell Proliferation," *Br. J. Dermatol.* 148:334-336.
Schlegel et al. (2002) "Structures of quartz (1010)- and (1011)-water interfaces determined by X-ray reflectivity and atomic force microscopy of natural growth surfaces," *Geochim. Cosmochim. Acta*, vol. 66, No. 17, pp. 3037-3054.
Schmid et al. (2003) "Preparation of Metallic Films on Elastomeric Stamps and Their Application on Contact Processing and Contact Printing," *Adv. Funct. Mater*. 13:145-153.
Schmid et al. (Mar. 25, 2000) "Siloxane Polymers for High-Resolution, High-Accuracy Soft Lithography," *Macromolecules* 33(8):3042-3049.
Schmid et al. (May 11, 1998) "Light- Coupling Masks for Lensless, Sub-wavelength Optical Lithography," *Appl. Phys. Lett.* 72(19):2379-2381.
Schmidt et al. (Mar. 8, 2001) "Thin Solid Films Roll up into Nanotubes," *Nature* 410:168.
Schnable et al. (1969) "Aluminum Metallization; Advantages and Limitations for Integrated Circuit Applications," *IEEE* 57:1570-1580.
Schneider et al. (2008) "Mechanical Properties of Silicones for Mems," *J. Micromech. Microeng*. 18:065008.
Schon et al. (1995) "Ambipolar Pentacene Field-Effect Transistors and Inverters," *Science* 287:1022-1023.
Scorzoni et al. (Oct. 4, 2004) "On the Relationship Between the Temperature Coefficient of Resistance and the Thermal Conductance of Integrated Metal Resistors," *Sens Actuators A* 116(1):137-144.
Search and Examination Report, Corresponding to Singapore Application No. 200904208-6, Mailed Dec. 17, 2010.
Search Report and Examination Report Corresponding to Singapore Patent Application No. 200901178-4, Completed Mar. 13, 2010.
Search Report and First Written Opinion, Corresponding to Singapore Patent Application No. 200902530-5, Dated Sep. 23, 2010.
Search Report and Written Opinion, Corresponding to Singapore Application No. 200901451-5, Mailed Dec. 22, 2010.
Search Report Corresponding to Singapore Patent Application No. SG 200607372-0, Mailer Oct. 17, 2007.
Search Report Corresponding to Taiwanese Patent Application No. 095121212, Completed Oct. 8, 2010.
Search Report, Corresponding to Republic of China (Taiwan) Patent Application No. 094118507, Dated Feb. 24, 2007.
Seidel et al. (2004) "High-Current Nanotube Transistors," *Nano Lett.*, vol. 4, No. 5, pp. 831-834.

(56) References Cited

OTHER PUBLICATIONS

Sekitani et al. (2005) "Bending Experiment on Pentacene Field-Effect Transistors on Plastic Films," *Appl. Phys. Lett.* 86:073511.

Sekitani et al. (2009) "Stretchable Active-Matrix Organic Light-Emitting Diode Display Using Printable Elastic Conductors," *Nature Mater.* 8:494-499.

Sekitani et al. (Sep. 12, 2008) "A Rubberlike Stretchable Active Matrix Using Elastic Conductors," *Science* 321:1468-1472.

Sen et al. (2002) "Nonequilibrium Processes for Generating Silicon Nanostructures in Single-Crystalline Silicon," *Pure Appl. Chem.* 74(9):1631-1641.

Serikawa et al. (May 1, 2000) "High-Mobility Poly-Si Thin Film Transistors Fabricated on Stainless-Steel Foils by Low-Temperature Processes Using Sputter-Depositions," *Jpn. J. Appl. Phys.* 39:L393-L395.

Servanti et al. (2005) "Functional Pixel Circuits for Elastic AMOLED displays," *Proc. IEEE* 93:1257-1264.

Service, R.F. (Aug. 15, 2003) "Electronic Textiles Charge Ahead," *Science* 301:909-911.

Shan et al. (2004) "From Si Source Gas Directly to Positioned, Electrically Contained Si Nanowires: The Self-Assembling 'Grow-in-Place' Approach," *Nano Lett.* 4(11):2085-2089.

Sharp et al. (2003) "Holographic Photonic Crystals with Diamond Symmetry," *Phys. Rev. B* 68:205102/1-205102/6.

Sheraw et al. (2002) "Organic Thin-Film Transistor-Driven Polymer-Dispersed Liquid Crystal Displays on Flexible Polymeric Substrates," *Appl. Phys. Lett.* 80:1088-1090.

Shetty et al. (2005) "Formation and Characterization of Silicon Films on Flexible Polymer Substrates," *Mater. Lett.* 59:872-875.

Shi et al. (2001) "Free-Standing Single Crystal Silicon Nanoribbons," *J. Am. Chem. Soc.* 123(44):11095-11096.

Shi et al. (Sep. 2000) "Synthesis of Large Areas of Highly Oriented, Very Long Silicon Nanowires," *Adv. Mater.* 12(18):1343-1345.

Shin et al. (2003) "PDMS-Based Micro PCR Chip with Parylene Coating," *J. Micromech. Microeng.* 13:768-774.

Shtein et al. (Oct. 15, 2004) "Direct Mask-Free Patterning of Molecular Organic Semiconductors Using Organic Vapor Jet Printing," *J. Appl. Phys.* 96(8):4500-4507.

Shull et al. (1998) "Axisymmetric Adhesion Tests of Soft Materials," *Macromol. Chem. Phys.* 199:489-511.

Siegel et al. (2009) "lightweight, Foldable Thermochromic Displays on Paper," *Lab Chip* 9:2775-2781.

Siegel et al. (2010) "Foldable Printed Circuit Boards on Paper Substrates," *Adv. Funct. Mater.* 20:28-35.

Siegel et al. (Web Release Feb. 7, 2007) "Microsolidics: Fabrication of Three-Dimensional Metallic Microstructures in Poly(dimethylsiloxane)," *Adv. Mater.* 19(5):727-733.

Sim et al. (1993) "An Analytical Back-Gate Bias Effect Model for Ultrathin SOI CMOS Devices," *IEEE Trans. Elec. Dev.* 40:755-765.

Sirringhaus et al. (2003) "Inkjet Printing of Functional Materials," *MRS Bull.* 28:802-806.

Sirringhaus et al. (Dec. 15, 2000) "High-Resolution Inkjet Printing of All-Polymer Transistor Circuits," *Science* 290:2123-2126.

Sirringhaus, H. (2005) "Device Physics of Solution-Processed Organic Field-Effect Transistors," *Adv. Mater.* 17:2411-2425.

Smay et al. (2002) "Colloidal Inks for Directed Assembly of 3-D Periodic Structures," *Langmuir* 18:5429-5437.

Smith et al. (2000) "Electric-Field Assisted Assembly and Alignment of Metallic Nanowires," *Appl. Phys. Lett.* 77(9):1399-1401.

Snow et al. (2003) "Random networks of carbon nanotubes as an electronic material," *Appl. Phys. Lett.*, vol. 82, No. 13, pp. 2145-2147.

Snow et al. (2005) "High-mobility carbon-nanotube transistors on a polymeric substrate," *Appl. Phys. Lett.*, 86, 033105.

So et al. (2008) Organic Light-Emitting Devices for Solid-State Lighting, *MRS Bull.* 33:663-669.

Someya et al. (2005) "Conformable, Flexible, Large-Area Networks of Pressure and Thermal Sensors with Organic Transistor Active Matrixes," *Proc. Nat. Acad. Sci. USA* 102:12321-12325.

Someya et al. (2005) "Integration of Organic FETs with Organic Photodiodes for a Large Area, Flexible, and Lightweight Sheet Image Scanners," *IEEE Trans. Electron Devices* 52:2502-2511.

Someya et al. (Jul. 6, 2004) "A Large-Area, Flexible, Pressure Sensor Matrix with Organic Field-Effect Transistors for Artificial Skin Applications," *Proc. Nat. Acad. Sci. USA* 101(27):9966-9970.

Soole et al. (Mar. 1991) "InGaAs Metal-Semiconductor-Metal Photodetectors for Long Wavelength Optical Communications," *IEEE J. Quantum Electron.* 27(3):737-752.

Soong et al. (1984) "Adverse Reactions to Virgin Silk Sutures in Cataract Surgery," *Ophthalmology* 91:479-483.

Srinivasan et al. (Web Release Mar. 26, 2007) "Piezoelectric/Ultrananocrystalline Diamond Heterostructures for High-Performance Multifunctional Micro/Nanoelectromechanical Systems," *Appl. Phys. Lett.* 90:134101.

Stafford et al. (Aug. 2004) "A Buckling-Based Metrology for Measuring the Elastic Moduli of Polymeric Thin Films," *Nature Mater.* 3:545-550.

Star et al. (2004) "Nanotube Optoelectric Memory Devices," *Nano Lett.*, vol. 4, No. 9, pp. 1587-1591.

Storm et al. (Aug. 2003) "Fabrication of Solid-State Nanopores with Single-Nanometre Precision," *Nat. Mater.* 2:537-540.

Streetman et al. (2000) "Intrinsic Material," In; Solid State Electronic Devices, 5$^{th}$ Ed., Prentice Hall; Upper Saddle River, NJ; pp. 74-75.

Strukov et al. (2005) "CMOL FPGA: A Reconfigurable Architecture for Hybrid Digital Circuits with Two-Terminal Nanodevices," *Nanotechnology* 16:888-900.

Su et al. (2000) "Lattice-Oriented Growth of Single-Walled Carbon Nanotubes," *J. Phys. Chem. B* 104(28):6505-6508.

Sum et al. (2009) "Near-Infrared Spectroscopy for the Detection of Lipid Core Coronary Plaques," *Curr. Cardiovasc. Imag. Rep.* 2:307-315.

Sumant et al. (Apr. 2005) "Toward the Ultimate Tribological Interface: Surface Chemistry and Nanotribology of Ultrananocrystalline Diamond," *Adv. Mater.* 17(8):1039-1045.

Sun et al. (2004) "Fabricating Semiconductor Nano/Microwires and Transfer Printing Ordered Arrays of Them onto Plastic Substrates," *Nano Lett.* 4:1953-1959.

Sun et al. (2005) "Advances in Organic Field-Effect Transistors," *J. Mater. Chem.* 15:53-65.

Sun et al. (2005) "Bendable GaAs Metal-Semiconductor Field-Effect Transistors Formed with Printed GaAs Wire Arrays on Plastic Substrates," *Appl. Phys. Lett.* 87:083501.

Sun et al. (2005) "Photolithographic Route to the Fabrication of Micro/Nanowires of III-V Semiconductors," *Adv. Fuct. Mater.* 15:30-40.

Sun et al. (2007) "Controlled Buckling of Semiconductor Nanoribbons for Stretchable Electronics," *Nat. Nanotechnol.* 1:201-207.

Sun et al. (2007) "Structural Forms of Single Crystal Semiconductor Nanoribbons for High-Performance Stretchable Electronics," *J. Mater Chem.* 17:832-840.

Sun et al. (Aug. 2007) "Inorganic Semiconductors for Flexible Electronics," *Adv. Mater.* 19(15):1897-1916.

Sun et al. (Nov. 2006) "Buckled and Wavy Ribbons of GaAs for High-Performance Electronics on Elastomeric Substrates," *Adv. Mater.* 18(21):2857-2862.

Sundar et al. (2004) "Elastomeric Transistor Stamps: Reversible Probing of Charge Transport in Organic Crystals," *Science* 303:1644-1646.

Suo et al. (Feb. 22, 1999) "Mechanics of Rollable and Foldable Film-on-Foil Electronics," *Appl. Phys. Lett.* 74(8):1177-1179.

Supplementary European Search Report, Corresponding to European Application No. 05 75 6327, Completed Sep. 25, 2009.

Supplementary European Search Report, Corresponding to European Application No. 04 81 2651, Completed Oct. 19, 2010.

Swain et al. (2004) "Curved CCD Detector Devices and Arrays for Multi-Spectral Astrophysical Application and Terrestrial Stereo Panoramic Cameras," *Proc. SPIE* 5499:281-301.

Sze et al. (1985) *Semiconductor Devices, Physics and Technology*, 2$^{nd}$ ed., Wiley, New York, pp. 190-192.

Sze, S. (1985) *Semiconductor Devices: Physics and Technology*, New York: Wiley, pp. 428-467.

(56) References Cited

OTHER PUBLICATIONS

Sze, S. (1988) *VLSI Technology*, Mcgraw-Hill, 327-374, 566-611.
Sze, S. (1994) *Semiconductor Sensors*, John Wiley and Sons: New York, pp. 17-95.
Takamoto et al. (Jan. 20, 1997) "Over 30% Efficient InGaP/GaAs Tandem Solar Cells," *Appl. Phys. Lett.* 70(3):381-383.
Talapin et al. (Oct. 7, 2005) "PbSe Nanocrystal Solids for n- and p-Channel Thin Film Field-Effect Transistors," *Science* 310:86-89.
Tan et al. (Apr. 12, 2004) "Performance Enhancement of InGaN Light Emitting Diodes by Laser-Lift-off and Transfer from Sapphire to Copper Substrate," *Appl. Phys. Lett.* 84(15):2757-2759.
Tanase et al. (2002) "Magnetic Trapping and Self-Assembly of Multicomponent Nanowires," *J. Appl. Phys.* 91:8549-8551.
Tang et al. (2005) "One-Dimensional Assemblies of Nanoparticles: Preparation, Properties, and Promise," *Adv. Mater.* 17:951-962.
Tao et al. (2003) "Langmuir-Blodgett Silver Nanowire Monolayers for Molecular Sensing Using Surface-Enhanced Raman Spectroscopy," *Nano Lett.* 3:1229-1233.
Tate et al. (2000) "Anodization and Microcontact Printing on Electroless Silver: Solution-Based Fabrication Procedures for Low-Voltage Electronic Systems with Organic Active Components," *Langmuir* 16:6054-6060.
Teshima et al. (2001) "Room-Temperature Deposition of High-Purity Silicon Oxide Films by RF Plasma-Enhanced CVD," *Surf. Coat. Technol.* 146-147:451-456.
Theiss et al. (1998) "PolySilicon Thin Film Transistors Fabricated at 100° C. on a Flexible Plastic Substrate," *IEDM* 98:257-260.
Thornwood et al. (Oct. 1, 1990) "Utilizing Olptical Lithography in the Sub-Micron Dimensional Regime," *IBM Tech. Disc. Bull.* 33(5):187-188.
Timko et al. (2009) "Electrical Recording from Hearts with Flexible Nanowire Device Arrays," *Nano Lett.* 9:914-918.
Toader et al. (2004) "Photonic Band Gap Architectures for Holographic Lithography," *Phy. Rev. Lett.* 043905/1-043905/4.
Toader et al. (2004) "Photonic Band Gaps Based on Tetragonal Lattices of Slanted Pores," *Phys. Rev. Lett.* 90:233901/1-233901/4.
Tong (1999) *Semiconductor Wafer Bonding: Science and Technology*, John Wiley; New York, pp. 187-221.
Trau et al. (1997) "Microscopic Patterning of Orientated Mesoscopic Silica Through Guided Growth," *Nature* 390:674-676.
Trentler et al. (1995) "Solution-Liquid-Solid Growth of Crytalline III-V Semiconductors: An Analogy to Vapor-Liquid-Solid Growth," *Science* 270:1791-1794.
Tseng et al. (Web Release Dec. 19, 2003) "Monolithic Integration of Carbon Nanotube Devices with Silicon MOS Technology" *Nano Lett.* 4(1):123-127.
Ucjikoga, S. (2002) "Low-Temperature Polycrystalline Silicon Thin-Film Transistor Technologies for System-on-Glass Displays," *MRS Bull.* 27:881-.
Urruchi et al. (2000) "Etching of DLC Films Using a Low Intensity Oxygen Plasma Jet," *Diamond Relat. Mater.* 9:685-688.
Vanhollenbeke et al. (2000) "Compliant Substrate Technology: Integration of Mismatched Materials for Opto-Electronic Applications," *Prog. Cryst. Growth Charact. Mater.* 41(1-4):1-55.
Velev et al. (1997) "Porous silica via colloidal crystallization," *Nature* 389:447-448.
Vepari et al. (Aug. Sep. 2007) "Silk as a Biomaterial," *Prog. Polym. Sci.* 32(8-9):991-1007.
Vilan et al. (2000) "Molecular Control Over Au/GaAs Diodes," *Nature* 404:166-168.
Vinck et al. (2003) "Increased Fibroblast Proliferation Induced by Light Emitting Diode and Low Power Laser Irradiation," *Lasers Med. Sci.* 18:95-99.
Viventi et al. (Mar. 2010) "A Conformal, Bio-Interfaced Class of Silicon Electronics for Mapping Cardiac Electrophysiology," *Sci. Trans. Med.* 2(24):24ra22.
Vlasov et al. (2001) "On-Chip Natural Assembly of Silicon Photonic Bandgap Crystals," *Nature* 414:289-293.
Voss, D. (2000) "Cheap and Cheerful Circuits," *Nature* 407:442-444.
Wagner et al. (2003) "Silicon for Thin-Film Transistors," *Thin Solid Films* 430:15-19.
Wagner et al. (2005) "Electronic Skin: Architecture and Components," *Physica E* 25:326-334.
Wagner et al. (Mar. 1, 1964) "Vapor-Liquid-Solid Mechanism of Single Crystal Growth," *Appl. Phys. Lett.* 4(5):89-90.
Waksman et al.(2008) "Photopoint Photodynamic Therapy Promotes Stabilization of Atherosclerotic Plaques and Inhibits Plaque Progression," *J. Am. Coil. Cardiol.* 52:1024-1032.
Wang et al. (2003) "A Solution-Phase, Precursor Route to Polycrystalline $SnO_2$ Nanowires that can be Used for Gas Sensing under Ambient Conditions," *J. Am. Chem. Soc.* 125:16176-16177.
Wang et al. (2005) "Electronically Selective Chemical Functionalization of Carbon Nanotubes: Correlation between Raman Spectral and Electrical Responses," *J. Am. Chem. Soc.*, 127:11460-11468.
Wang et al. (2005) "Oxidation Resistant Germanium Nanowires: Bulk Synthesis, Long Chain Alkanethiol Functionalization, and Langmuir-Blodgett Assembly," *J. Am. Chem. Soc.* 127(33):11871-11875.
Wang et al. (2006) "Direct Synthesis and Characterization of CdS Nanobelts," *Appl. Phys. Lett.* 89:033102.
Wang et al. (Aug.-Sep. 2008) "In Vivo Degradation of Three-Dimensional Silk Fibroin Scaffolds," *Biomaterials* 29(24-25):3415-3428.
Waxman et al. (2009) "In vivo Validation of a Catheter-Based Near-Infrared Spectroscopy System for Detection of Lipid Core Coronary Plaques: Initial Results of the Spectacl Study," *J. Am. Coil. Cardiol. Img.* 2:858-868.
Waxman, S. (2008) "Near-Infrared Spectroscopy for Plaque Characterization," *J. Interv. Cardiol.* 21:452-458.
Weber et al. (Jan. 2004) "A Novel Low-Cost, High Efficiency Micromachined Silicon Solar Cell," *IEEE Electron Device Lett.* 25(1):37-39.
Wen et al. (Web Release Dec. 4, 2004) "Controlled Growth of Large-Area, Uniform, Vertically Aligned Arrays of $\alpha\text{-Fe}_2O_2$ Nanobelts and Nanowires," *J. Phys. Chem. B* 109(1):215-220.
Whang et al. (2003) "Large-Scale Hierarchical Organization of Nanowire Arrays for Integrated Nanosystems," *Nano Lett.* 3(9):1255-1259.
Williams et al. (Oct. 2006) "Growth and Properties of Nanocrystalline Diamond Films," *Phys. Stat. Sol. A* 203(13):3375-3386.
Williams et al. (Web Release Jan. 23, 2006) "Comparison of the Growth and Properties of Ultrananocrystalline Diamond and Nanocrystalline Diamond," *Diamond Relat. Mater.* 15:654-658.
Willner et al. (2002) "Functional Nanoparticle Architectures for Senoric, Optoelectronic, and Bioelectronic Applications," *Pure Appl. Chem.* 74(9):1773-1783.
Wilson et al. (2006) "ECoG Factors Underlying Multimodal Control of a Brain—Computer Interface," *IEEE Trans. Neural Syst. Rehabil. Eng.* 14:246-250.
Wind et al. (May 20, 2002) "Vertical Scaling of Carbon Nanotube-Field-Effect Transitors Using Top Gate Electrodes," *Appl. Phys. Lett.* 80(20):3871-3819.
Wise et al. (Jul. 2008) "Microelectrodes, Microelectronics, and Implantable Neural Microsystems," *Proc. IEEE* 96(7):1184-1202.
Won et al. (2004) "Effect of Mechanical and Electrical Stresses on the Performance of an a-Si:H TFT on Plastic Substrate," *J. Electrochem. Soc.* 151:G167-G170.
Wong-Riley et al. (2005) "Photobiomodulation Directly Benefits Primary Neurons Functionally Inactivated by Toxins," *J. Biol. Chem.* 280:4761-4771.
Woodburn et al. (1996) "Phototherapy of Cancer and Atheromatous Plaque with Texaphyrins," *J. Clin. Laser Med. Surg.* 14:343-348.
Wu et al. (2001) "Amorphous Silicon Crystallization and Polysilicon Thin Film Transistors on SiO2 Passivated Steel Foil Substrates," *Appl. Surf. Sci* 175-176:753-758.
Wu et al. (2001) "Direct Observation of Vapor-Liquid-Solid Nanowire Growth," *J. Am. Chem. Soc.* 123(13):3165-3166.
Wu et al. (2001) "Thermal Oxide of Polycrystalline Silicon on Steel Foil as a Thin-Film Transistor Gate Dielectric," *Appl. Phys. Lett.* 78:3729-2731.

(56) References Cited

OTHER PUBLICATIONS

Wu et al. (2002) "Block-by-Block Growth of Single-Crystalline Si/SiGe Superlattice Nanowires," *Nano Lett.* 2(2):83-86.
Wu et al. (2002) "Growth of Au-Catalyzed Ordered GaAs Nanowire Arrays by Molecular-Beam Epitaxy," *Appl. Phys. Lett.* 81:5177-5179.
Wu et al. (2002) "Inorganic Semiconductor Nanowires: Rational Growth, Assembly, and Novel Properties," *Chem. Eur. J.* 8(6):1261-1268.
Wu et al. (2003) "Growth, Branching, and Kinking of Molecular-Beam Epitaxial (110) GaAs Nanowires,"*Appl. Phys. Lett.* 83:3368-3370.
Wu et al. (Jul. 1, 2004) "Single-Crystal Metallic Nanowires and Metal/Semiconductor Nanowire Heterostructures," *Nature* 430:61-65.
Wu et al. (Nov. 2002) "Complementary Metal-Oxide-Semiconductor Thin-Film Transistor Circuits from a High-Temperature Polycrystalline Silicon Process on Steel Foil Substrates," *IEEE Trans. Electr. Dev.* 49(11):1993-2000.
Xia (1998) "Soft Lithography" *Angew. Chem. Int. Ed.* 37:551-575.
Xia et al. (1996) "Shadowed Sputtering of Gold on V-Shaped Microtrenches Etched in Silicon and Applications in Microfabrication," *Adv. Mater.* 8(9):765-768.
Xia et al. (1998) "Soft Lithography," *Annu. Rev. Mater. Sci.* 28:153-184.
Xia et al. (1999) "Unconventional Methods for Fabricating and Patterning Nanostructures," *Chem. Rev.* 99:1823-1848.
Xia et al. (2003) "One-Dimensional Nanostructures: Synthesis, Characterization and Applications," *Adv. Mater.* 15:353-389.
Xia et al. (Jul. 19, 1996) "Complex Optical Surfaces Formed by Replica Molding Against Elastomeric Masters," *Science* 273:347-349.
Xiang et al. (Mar. 25, 2006) "Ge/Si Nanowire Heterostructures as High-Performance Field-Effect Transistors," *Nature* 441:489-493.
Xiao et al. (2003) "High-mobility thin-film transistors based on aligned carbon nanotubes," *Appl. Phys. Lett.*, vol. 83, No. 1, pp. 150-152.
Xie et al. (May 2003) "Polymer-Controlled Growth of $Sb_2Se_3$ Nanoribbons Via a Hydrothermal Process," *J. Cryst. Growth* 252(4):570-574.
Xin et al. (Jun. 2005) "Evaluation of Polydimethylsiloxane Scaffolds with Physiologically-Relevant Elastic Moduli: Interplay of Substrate Mechanics and Surface Chemistry Effects on Vascular Smooth Muscle Cell Response," *Biomaterials* 26(16):3123-3129.
Yang et al. (1997) "Mesoporous Silica with Micrometer-Scale Designs," *Adv. Mater.* 9:811-814.
Yang et al. (2000) "Stability of Low-Temperature Amorphous Silicon Thin Film Transistors Formed on Glass and Transparent Plastic Substrates," *J. Vac. Sci. Technol. B* 18:683-689.
Yang et al. (2002) "Creating Periodic Three-Dimensional Structures by Multibeam Interface of Visible Laser," *Chem. Mater.* 14:2831-2833.
Yang et al. (Dec. 2007) "RFID Tag and Rf Structures on a Paper Substrate Using Inkjet-Printing Technology," *IEEE Trans. Microw. Theory Tech.* 55(12):2894-2901.
Yang, P. (2005) "The Chemistry and Physics of Semiconductor Nanowires," *MRS Bull.* 30:85-.
Yanina et al. (2002) "Terraces and ledges on (001) spinel surfaces," *Surf. Sci.*, 513:L402-L412.
Yao et al. (2008) "Seeing Molecules by Eye: Surface Plasmon Resonance Imaging at Visible Wavelengths with High Spatial Resolution and Submonolayer Sensitivity," *Angew. Chem.* 47:5013-5017.
Yao et al. (2010) "Functional Nanostructured Plasmonic Materials," *Adv. Mater.* 22:1102-1110.
Yao et al. (Mar. 2000) "High-Field Effect Electrical Transport in Single-Walled Carbon Nanotubes," *Phys. Rev. Lett.* 84(13):2941-2944.
Yeager et al. (Aug. 30, 2008) "Characterization of Flexible ECoG Electrode Arrays for Chronic Recording in Awake Rats," *J. Neurosci. Methods* 173(2):279-285.

Yeh et al. (1994) "Fluidic Self-Assembly for the Integration of GaAs Light Emitting Diodes on Si Substrates," *IEEE Photon. Techn. Lett.* 6:706-708.
Yin et al. (2000) "A Soft Lithography Approach to the Fabrication of Nanostructures of Single Crystalline Silicon with Well-Defined Dimensions and Shapes," *Adv. Mater.* 12:1426-1430.
Yin et al. (2005) "Colloidal Nanocrystal Synthesis and the Organic-Inorganic Interface," *Nature* 437:664-670.
Yoon et al. (2005) "Low-Voltage Organic Field-Effect Transistors and Inverters Enabled by Ultrathin Cross-Linked Polymers as Gate Dielectrics," *J. Am. Chem. Soc.* 127:10388-10395.
Yu et al. (2000) "Silicon Nanowires: Preparation, Device Fabrication, and Transport Properties," *J. Phys. Chem. B* 104(50):11864-11870.
Yu et al. (2003) "Solution-Liquid-Solid Growth of Soluble GaAs Nanowires," *Adv. Mater.* 15:416-419.
Yu et al. (2003) "Two-Versus Three-Dimensional Quantum Confinement in Indium Phosphide Wires and Dots," *Nat. Mater.* 2:517-520.
Yu et al. (2004) "The Yield Strength of Thin Copper Films on Kapton," *J. Appl. Phys.* 95:2991-2997.
Yuan et al. (2006) "High-Speed Strained-Single-Crystal-Silicon Thin-Film Transistors on Flexible Polymers," *J. Appl. Phys.* 100:013708.
Yurelki et al. (Jul. 24, 2004) "Small-Angle Neutron Scattering from Surfactant-Assisted Aqueous Dispersions of Carbon Nanotubes," *J. Am. Chem. Soc.* 126(32):9902-9903.
Zakhidov et al. (1998) "Carbon Structure with Three-Dimensional Periodicity at Optical Wavelengths," *Science* 282:897-901.
Zaumseil et al. (2003) "Nanoscale Organic Transistors that use Source/Drain Electrodes Supported by High Resolution Rubber Stamps," *Appl. Phys. Lett.* 82(5):793-795.
Zaumseil et al. (2003) "Three-Dimensional and Multilayer Nanostructures Formed by Nanotransfer Printing," *Nano Lett.* 3(9):1223-1227.
Zhang et al. (2001) "Electric-field-directed growth of aligned single-walled carbon nanotubes," *Appl. Phys. Lett.*, vol. 79, No. 19. pp. 3155-3157.
Zhang et al. (2005) "Low-Temperature Growth and Photoluminescence Property of ZnS Nanoribbons," *J. Phys. Chem. B* 109(39):18352-18355.
Zhang et al. (2006) "Anomalous Coiling of SiGe/Si and SiGe/Si/Cr Helical Nanobelts," *Nano Lett.* 6(7):1311-1317.
Zhang et al. (Apr. 2003) "Oxide-Assisted Growth of Semiconducting Nanowires," *Adv. Mater.* 15(7-8):635-640.
Zhang et al. (Apr. 5, 2004) "Structure and Photoiluminescence of ZnSe Nanoribbons Grown by Metal Organic Chemical Vapor Deposition," *Appl. Phys. Lett.* 84(14):2641-2643.
Zhang et al. (Feb. 9, 2006) "Electronic Transport in Nanometre-Scale Silicon-on-Insulator Membranes," *Nature* 439:703-706.
Zhao et al. (Mar. 2007) "Improved Field Emission Properties from Metal-Coated Diamond Films," *Diamond Re/at Mater.* 16(3):650-653.
Zheng et al. (1998) "Sudden Cardiac Death in the United States, 1989 to 1998," *Circulation* 104, 2158-2163 (1998).
Zheng et al. (2004) "Shape-and Solder-Directed Self-Assembly to Package Semiconductor Device Segments," *Appl. Phys. Lett.* 85:3635-3637.
Zheng et al. (Aug. 31, 2004) "Sequential Shape-and-Solder-Directed Self Assembly of Functional Microsystems," *Proc. Natl. Acad. Sci. USA* 101(35):12814-12817.
Zhou et al. (2002) "An Efficient Two-Photon-Generated Photoacid Applied to Positive-Tone 3D Microfabrication," *Science* 296:1106-1109.
Zhou et al. (2004) "p-Channel, n-Channel Thin Film Transistors and p-n Diodes Based on Single Wall Carbon Nanotube Networks," *Nano Lett.* 4:2031-2035.
Zhou et al. (2005) "Band Structure, Phonon Scattering, and the Performance Limit of Single-Walled Carbon Nanotube Transistors," *Phys. Rev. Lett.* 95:146805.
Zhou et al. (2005) "Mechanism for Stamp Collapse in Soft Lithography," *Appl. Phys. Lett.* 87:251925.
Zhu et al. (2005) "Spin on Dopants for High-Performance Single Crystal Silicon Transistors on Flexible Plastic Substrates," *Appl. Phys. Lett.* 86(133507)1-3.

(56) References Cited

OTHER PUBLICATIONS

Zipes et al. (2006) "ACC/AHA/ESC 2006 Guidelines for Management of Patients With Ventricular Arrhythmias and the Prevention of Sudden Cardiac Death: A Report of the American College of Cardiology/American Heart Association Task Force and the European Society of Cardiology Committee for Practice Guidelines (Writing Committee to Develop Guidelines for Management of Patients With Ventricular Arrhythmia and the Prevention of Sudden Cardiac Death," *Circulation* 114:385-484.

[Authors unknown] (1996) "National Nosocomial Infections Surveillance (NNIS) Report, Data Summary from Oct. 1986-Apr. 1996, Issued May 1996. A Report from the National Nosocomial Infections Surveillance (NNIS) System," *Am. J. Infect. Control.* 24:380-388.

Anderson et al. (2009) "Clinical and Financial Outcomes Due to Methicillin Resistant Staphylococcus Aureus Surgical Site Infection: A Multi-Center Matched Outcomes Study," *PLoS One.* 4(12):1-8.

Banerjee et al. (2006) "Low-Temperature Deposition of ZnO Thin Films on PET and Glass Substrates by DC-Sputtering Technique," *Thin Solid Films.* 496:112-116.

Becker et al. (2004) "Opinion of the Scientific Panel on Dietetic Products, Nutrition and Allergies on a Request from the Commission Related to the Tolerable Upper Intake Level of Silicon," *The EFSA Journal* 60:1-11.

Bettinger et al. (2010) "Biomaterial-Based Organic Electronic Devices," *Polym. Int.* 59:563-567.

Bettinger et al. (2010) "Organic Thin Film Transistors Fabricated on Resorbable Biomaterial Substrates," *Adv. Mater.* 22:651-655.

Block et al. (1998) "Association of Serum Phosphorus and Calcium X Phosphate Product with Mortality Risk in Chronic Hemodialysis Patients: A National Study," *Am. J. Kidney Dis.* 31(4):607-61.

Bramson et al. (2003) "Enabling Topical Immunization Via Microporation: A Novel Method for Pain-Free and Needle-Free Delivery of Adenovirus-Based Vaccines," *Gene Ther.* 10:251-260.

Brugger et al. (1999) "Self-Aligned 3D Shadow Mask Technique for Patterning Deeply Recessed Surfaces of Micro-Electro-Mechanical Systems Devices," *Sensors and Actuators.* 76 :329-334.

Butler et al. (2000) "In Vivo Degredation of Tungsten Embolisation Coils," *The British Journal of Radiology.* 73:601-603.

Bylander et al. (2005) "Current measurement by real-time counting of single electrons," *Nature.* 434(7031):361-364.

Campbell et al. (1999) "Dynamics of Oxidation of Aluminum Nanoclusters using Variable Charge Molecular-Dynamics Simulations on Parallel Computers," *Phys. Rev. Lett.* 82:4866-4869.

Capala et al. (2003) "Boron Neutron Capture Therapy for Glioblastoma Multiforme: Clinical Studies in Sweden," *J. Neuro-Oncol.* 62:135-144.

Capelli et al. (2011) "Integration of Silk Protein in Organic and Light Emitting Transistors," *Organic Electronics.* 12:1146-1151.

Cheng (2011) "Effects of Post-Deposition Rapid Thermal Annealing on Aluminum-Doped ZnO Thin Films Grown by Atomic Layer Deposition," *Appl. Surf. Sci.* 258:604607.

Chiappini et al. (2010) "Biodegradable Porous Silicon Barcode Nanowires with Defined Geometry," *Adv. Funct. Mater.* 20:2231-2239.

Cho et al. (2009) "Characterization of the Biaxial Textures of MgO Thin Films Grown by E-Beam Evaporation," *Journal of the European Ceramic Society.* 30:481-484.

Choi et al. (2009) "The Effects of Rapid Thermal Annealing on the Performance of ZnO Thin-Film Transistors," *J. Kor. Phys. Soc.* 55:1925-1930.

Chou et al. (1996) "Imprint Lithography with 25 Nanometer Resolution," *Science.* 272(5258):85-87.

Chung et al. (2003) "Nanoscale Gap Fabrication by Carbon Nanotube-Extracted Lithography (CEL)," *Nano Lett.* 3(8):1029-1031.

Cong et al. (2010) "CNT-Based Photopatternable Nanocomposites with High Electrical Conductivity and Optical Transparency," *J. Micromech. Microeng.* 20:025002.

Costner et al. (2009) "Nanoimprint Lithography Materials Development for Semiconductor Device Fabrication," *Annu. Rev. Mater. Res.* 39:155-180.

Danckwerts (1950) "Absorption by Simultaneous Diffusion and Chemical Reaction," *Tran. Faraday Soc.* 46:300-304.

Darhuber et al. (2003) "Microfluidic Actuation by Modulation of Surface Stresses," *Appl. Phys. Lett.* 82(4):657-659.

Diao et al. (2010) "Reduced Low Frequency Noise in Electron Beam Evaporated MgO Magnetic Tunnel Junctions," *Appl. Phys. Lett.* 96:202506.

Dickey et al. (2008) "Fabrication of Arrays of Metal and Metal Oxide Nanotubes by Shadow Evaporation," *ACS. Nano.* 2(4):800-808.

Dickey et al. (2010) "Transistors Formed from a Single Lithography Step Using Information Encoded in Topography," *Small.* 6(18):2050-2057.

Dolan (1977) "Offset Masks for Lift—Off Photoprocessing," *Appl. Phys. Lett.* 31(5):337-339.

Egger et al. (2005) "Dynamic Shadow Mask Technique: A Universal Tool for Nanoscience," *Nano Lett.* 5(1):15-20.

Flanders (1979) "X-ray Lithography at $\angle 100$ Å Linewidths Using X-Ray Masks Fabricated by Shadowing Techniques," *J. Vac. Sci. Technol.* 16(6):1615-1619.

Gu et al. (2009) "In Vitro Corrosion and Biocompatibility of Binary Magnesium Alloys," *Biomaterials.* 30:484-498.

Guo (2004) "Recent Progress in Nanoimprint Technology and its Applications," *J. Phys. D: Appl. Phys.* 37:R123-R141.

Hamer et al. (2009) "AMOLED Displays Using Transfer-Printed Integrated Circuits," In; *SID 2009 International Symposium Digest of Technical Papers.* 15:947-950.

Han et al. (2010) "Potential Dissolution and Photo-Dissolution of ZnO Thin Films," *Journal of Hazardous Materials.* 178:115-122.

Hao et al. (2002) "Comparison of the Properties for ZnO: Al Films Depositied on Polyimide and Glass Substrates," *Mater. Sci. Eng. B.* 90:50-54.

Haran et al. (Dec. 15-17, 2008) "22 nm Technology Compatible Fully Functional 0.1 μm$^2$ 6T-SRAM Cell," In; *Electron Devices Meeting, 2008. IEDM 2008. IEEE International.* San Francisco, California.

Hawkeye et al. (2007) "Glancing Angle Deposition: Fabrication, Properties, and Applications of Micro- and Nanostructured Thin Films," J. Vac. Sci. Technol. A. 25:1317-1335.

Hawtin et al. (1964) "The Role of In-Pore Mass Transport Resistance in The Reaction of Porous Solids with Gases," *Chemical Engineering Science.* 19:819-834.

Heo et al. (2007) "Effects of O$_2$ Ambient on the Properties of MgO Thin Films Deposited by E-Beam Evaporation," *J. Electrochem. Soc.* 154(11):J352-J356.

Hiramatsu et al. (2007) "Influence of Thermal Annealing on Microstructure of Zinc Oxide Films Deposited by Magnetron Sputtering," *Jpn. J. Appl. Phys.* 46:3319-3323.

Holdeman et al. (1985) "An Approach to Fabricating Sub-Half-Micrometer-Length Gates for GaAs Metal-Semiconductor Field-Effect Transistors," J. Vac. Sci. Technol. B. 3(4):956-958.

Hu et al. (2008) "Dynamic Protein Water Relationships During Beta Sheet Formation," *Macromolecules.* 41:3939-3948.

Hu et al. (2009) "Microphase Separation Controlled Beta Sheet Crystallization Kinetics in Fibrous Proteins," *Macromolecules.* 42:2079-2087.

Hu et al. (2011) "Regulation Of Silk Material Structure By Temperature-Controlled Water Vapor Annealing," *Biomacromolecules.* 12:1686-1696.

Hua et al. (2004) "Polymer Imprint Lithography with Molecular-Scale Resolution," *Nano. Lett.* 4(12):2467-2471.

Hwang et al. (2008) "The Effects of the Microstructure of ZnO Films on the Electrical Performance of Their Thin Film Transistors," *Appl. Phys. Lett.* 93:222104.

Hwang et al. (Apr. 11, 2013) "Materials and Fabrication Processes for Transient and Bioresorbable High-Performance Electronics," *Adv. Funct. Mater.* e-publication.

Hwang et al. (May 17, 2013) "Materials for Bioresorbable Radio Frequency Electronics," *Advanced Materials.* e-publication.

Hwang et al. (Sep. 28, 2012) "A Physically Transient Form of Silicon Electronics, With Integrated Sensors, Actuators and Power Supply," *Science* 337(6102):1640-1644.

(56) References Cited

OTHER PUBLICATIONS

Iler (1973) "Effect of Adsorbed Alumina on the Solubility of Amorphous Silica in Water," *J. of Colloid Interf. Sci.* 43:399-408.
International Search Report and Written Opinion corresponding to International Application No. PCT/US12/56538, mailed Jun. 17, 2013.
Irimia-Vladu et al. (2010) "Biocompatible and Biodegradable Materials for Organic-Field Transistors," *Adv. Mater.* 20:4069-4076.
Irimia-Vladu et al. (2010) "Environmentally Sustainable Organic Field Effect Transistors," *Org. Electron.* 11:1974-1990.
Javey et al. (2004) "From the Cover: Ten to 50-nm-Long Quasi-Ballistic Carbon Nanotube Devices Obtained Without Complex Lithography," *Proc. Nat. Acad. Sci. USA.* 101(37):13408-13410.
Jeon et al. (2007) "Low-Voltage Zinc-Oxide Thin-Film Transistors on a Conventional $SiO_2$ Gate Insulator Grown by Radio-Frequency Magnetron Sputtering at Room Temperature," *J. Kor. Phys. Soc.* 51:1999-2003.
Jones et al. (1987) "Preparation and Characterization of Molecule-Based Transistors with a 50-Nanometer Source-Drain Separation with Use of Shadow Deposition Techniques. Toward Faster, More Sensitive Molecule-Based Devices," *J. Am. Chem. Soc.* 109(18):5526-5528.
Kang et al. (2004) "Avoiding Cu Hillocks During the Plasma Process," *J. Electrochem. Soc.* 151(6):G391-G395.
Kim et al. (2009) "Roll-To-Roll Manufacturing of Electronics on Flexible Substrates Using Self-Aligned Imprint Lithography (SAIL)," *J. Soc. Inf. Disp.* 17(11):963-970.
Kim et al. (2010) "Dissolvable Films of Silk Fibroin for Ultrathin Conformal Bio Integrated Electronics," *Nature Materials.* 9(6):511-517.
Kim et al. (2010) "Microstructured Elastomeric Surfaces with Reversible Adhesion and Examples of Their Use in Deterministic Assembly by Transfer Printing," *Proc. Nat. Acad. Sci. USA* 107(40):17095-17100.
Kim et al. (Nov. 11, 2012) "Silk Inverse Opals," *Nature Photonics.* 6:818-823.
Köhler et al. (1999) "Direct Growth of Nanostructures by Deposition Through an Si 3N 4 Shadow Mask," *Physica E.* 4:196-200.
Kosiorek et al. (2004) "Shadow Nanosphere Lithography: Simulation and Experiment," *Nano Lett.* 4:1359-1363.
Kozicki et al. (Nov. 10, 2005) "Programmable Metallization Cell Memory Based on Ag-Ge-S and Cu-Ge-S Solid Electrolytes," In; *Non-Volatile Memory Technology Symposium 2005*, Dallas, Texas.
Kuoni et al. (2003) "Polyimide Membrane with ZnO Piezoelectric Thin Film Pressure Transducers as a Differential Pressure Liquid Flow Sensor," *J. Micromech. Microeng.* 13:S103-S107.
Kwadwo et al. (2010) "Layer-by-Layer Assembly of Charged Particles in Nonpolar Media," *Langmuir.* 26(12), 9974-9980.
Lee (2009) "Effects of Sputtering Pressure and Thickness on Properties of ZnO: Al Films Deposited on Polymer Substrates," *J. Electroceram.* 23:512-518.
Lee et al. (2001) "Thickness Effect on Secondary Electron Emission of MgO Layers," *Appl. Surf. Sci.* 174:62-69.
Legnani et al. (2008) "Bacterial Cellulose Membrane as Flexible Substrate for Organic Light Emitting Devices," *Thin Film Solids.* 517:1016-1020.
Levine (2005)*Molecular Reaction Dynamics.* Cambridge University Press. Cambridge, United Kingdom.
Li et al (2008) "Cellular Level Biocompatibility and Biosafety of ZnO Nanowires," *J. Phys. Chem. C.* 112:20114-20117.
Li et al. (2005) "Facile Synthesis of Silver Nanoparticles Useful for Fabrication of High-Conductivity Elements for Printed Electronics," *J. Am. Chem. Soc.* 127:3266-3267.
Li et al. (Jan. 21, 2013) "An Analytical Model of Reactive Diffusion for Transient Electronics," *Adv. Funct. Mater.* 23:3106-3114.
Lim et al. (2007) "Au Micro-Pattern Fabrication on Cellulose Paper: Comparison Of μ-Contact Printing And Liftoff Techniques," *J. Micromech. Microeng.* 17:1415-1419.
Low et al. (2009) "The Biocompatibility of Porous Silicon in Tissues of the Eye," *Biomaterials.* 30(15):2873-2880.

Magda Gioia et al. (2007) "Characterization of the Mechanisms by which Gelatinase A, Neutrophil Collagenase, and Membrane-Type Metalloproteinase MMP-14 Recognize Collagen I and Enzymatically Process the Two Alpha-Chains," *J. Mol. Biol.* 368(4):1101-13.
Martinez-Boubeta et al. (2010) "Self-Assembled Multifunctional Fe/Mgo Nanospheres for Magnetic Resonance Imaging and Hyperthermia," *Nanomedicine: Nanotechnology, Biology, and Medicine.* 6:362-370.
Medina-Montes et al. (2011) "Effects of Sputtered ZnO Layers on Behavoir of Thin-Film Transistors Deposited at Room Temperature in a Nonreactive Atmosphere," *J. Electr. Mater.* 40:1461-1469.
Morita et al. (1990) "Growth of Native Oxide on a Silicon Surface,"*J. Appl. Phys.* 68:1272-1281.
Naghii et al. (2011) "Comparative Effects of Daily and Weekly Boron Supplementation on Plasma Steroid Hormones and Proinflammatory Cytokines," *J. Trace Elem. Med. Bio.* 25:54-58.
Ouyang et al. (2004) "Polymer Optoelectronic Devices with High-Conductivity Poly(3,4-Ethylenedioxythiophene) Anodes," *Journal of Macromolecular Science.* 41(12)1 497-1511.
Ozisik et al. (1971) "Carbon Loss from Graphite Cylinders Exposed to Steam for Short Times," *Nuclear Science and Engineering.* 44:310-319.
Pan et al. (2010) "Design and Fabrication of Flexible Piezo-Microgenerator by Depositing ZnO Thin Films on PET Substrates," *Sensors and Actuators A.* 159:96-104.
Pandy et al. (1998) "Experimental Investigation of High Si/Al Selectivity During Anisotropic Etching in Tetra-Methyl Ammonium Hydroxide," *J. Vac. Sci. Technol. A.* 16(2):868-872.
Park et al. (1999) "Fabrication of Metallic Electrodes with Nanometer Separation by Electromigration," *Appl. Phys. Lett.* 75:301-303.
Park et al. (2005) "Wireless Thermal Micro-Ablation of Skin for Transdermal Drug Delivery," In; *The 13th International Conference on Solid-state Sensors, Actuators and Microsystems.* 2:1238-1241.
Park et al. (2007) "High Resolution Electrohydrodynamic Jet Printing," *Nature Materials.* 6:782-789.
Park et al. (2008) "High Aspect-Ratio Cylindrical Nanopore Arrays and Their Use for Templating Titania Nanoposts," *Adv. Mater.* 20:738-742.
Park et al. (2008) "Nanoscale Patterns of Oligonucleotides Formed by Electrohydrodynamic Jet Printing with Applications in Biosensing and Nanomaterials Assembly," *Nano Lett.* 8:4210-4216.
Perry et al. (2008) "Nano- and Micropatterning of Optically Transparent, Mechanically Robust, Biocompatible Silk Fibroin Films," *Adv. Mater.* 20:3070-3072.
Peuster et al. (2001) "A Novel Approach to Temporary Stenting: Degradable Cardiovascular Stents Produced from Corrodible Metal-Results 6-18 Months After Implantation Into New Zealand White Rabbits," *Heart.* 86:563-569.
Peuster et al. (2003) "Biocompatibility of Corroding Tungsten Coils: In Vitro Assessment of Degradation Kinetics and Cytotoxicity on Human Cells." *Biomaterials.* 24:4057-4061.
Peuster et al. (2003) "Degradation of Tungsten Coils Implanted Into the Subclavian Artery of New Zealand White Rabbits is not Associated with Local or Systemic Toxicity," *Biomaterials.* 24:393-399.
Philipp et al. (1999) "Shadow Evaporation Method for Fabrication of Sub 10 nm Gaps Between Metal Electrodes," *Microelectron. Eng.* 46:157-160.
Piispanen et al. (1995) "Complex Formation Equilibria of Some Aliphatic alpha-Hydroxycarboxylic Acids. 1. The Determination of Protonation Constants and the Study of Calcium(II) and Magnesium(II) Complexes," *Acta Chemica Scandinavica.* 49:235-240.
Racz et al. (2004) "Nanofabrication Using Nanotranslated Stencil Masks and Lift Off," *J. Vac. Sci. Technol. B.* 22(1):74-76.
Rácz et al. (2007) "Characterization and Control of Unconfined Lateral Diffusion Under Stencil Masks," *J. Vac. Sci. Technol. B.* 25:857-861.
Rimstidt et al. (1980) "Kinetics of Silica-Water Reactions," *Geochim. Cosmochim. Ac.* 44:1683-1699.
Robbie et al. (1997) "Sculptured Thin Films and Glancing Angle Deposition: Growth Mechanics and Applications," *J. Vac. Sci. Technol. A.* 15(3):1460-1465.\.

(56) References Cited

OTHER PUBLICATIONS

Robbie et al. (1998) "Advanced Techniques for Glancing Angle Deposition," *J. Vac. Sci. Technol. B.* 16(3):1115-1122.
Rogers et al. (2010) "Materials and Mechanics for Stretchable Electronics," *Science.* 327:1603-1607.
Sankir et al. (2008) "Electrical and Morphological Characterization of Polyaniline/Sulfonated Poly(Arylene ether Sulfone) Composite Films," J. Mater. Sci.: Mater. El. 19(4):389-392.
Santra et al. (2010) "Silicon on Insulator Diode Temperature Sensor-A Detailed Analysis for Ultra-High Temperature Operation," *IEEE Sens. J.* 10(5):997-1003.
Schift (2008) "Nanoimprint Lithography: An Old Story in Modern Times? A Review," *J. Vac. Sci. Technol. B.* 26(2):458-480.
Seidel et al. (1990) "Anisotropic Etching of Crystalline Silicon in Alkaline Solutions," *Electrochem. Soc.* 137(11):3612-3626.
Shen et al. (2007) "Submicron Particles of SBA-15 Modified with MgO as Carriers for Controlled Drug Delivery," *Chem. Pharm. Bull.* 55(7):985-991.
Sofia et al. (2001) "Functionalized Silk-Based Biomaterials for Bone Formation," *J. Biomed. Mater. Res.* 54:139-148.
Song (2007) "Control of Biodegradation of Biocompatible Magnesium Alloys," *Corrosion Science.* 49:1696-1701.
Sordan et al. (2001) "Removable Template Route to Metallic Nanowires and Nanogaps," *Appl. Phys. Lett.* 79(13):2073-2075.
Tao et al. (2010) "Gold Nanoparticle-Doped Biocompatible Silk Films as a Path to Implantable Thermo-Electrically Wireless Powering Devices," *Appl. Phys. Lett.* 97:123702.
Tao et al. (Nov. 27, 2012) "Implantable, Multifunctional, Bioresorbable Optics," *Proc. Natl. Acad. Sci. USA.* 109(48):19584-19589.
Toader et al. (2001) "Proposed Square Spiral Microfabrication Architecture for Large Three-Dimensional Photonic Band Gap Crystals," *Science.* 292(5519):1113-1136.
Tomozawa et al. (1999) "Time Dependent Diffusion Coefficient of Water Into Silica Glass at Low Temperatures," *Mater. Sci. Eng. A.* 272:114-119.
Trewyn et al. (2008) "Biocompatible Mesoporous Silica Nanoparticles with Different Morphologies for Animal Cell Membrane Penetration," *Chemical Engineering Journal.* 137:23-29.
Vazquez-Mena et al. (2008) "Metallic Nanowires by Full Wafer Stencil Lithography," *Nano Lett.* 8:3675-3682.
Vojtěch et al. (2011) "Mechanical and Corrosion Properties of Newly Developed Biodegradable Zn-Based Alloys for Bone Fixation," *Acta Biomaterialia.* 7:3515-3522.
Wang et al. (2009) "Self-Aligned Fabrication of 10 nm Wide Asymmetric Trenches for Si/SiGe Heterojunction Tunneling Field Effect Transistors Using Nanoimprint Lithography, Shadow Evaporation, and Etching," *J. Vac. Sci. Technol. B.* 27(6):2790-2794.
Weber et al. (1993) "Fabrication of Narrow Lines by Shadow-Evaporated Lift-Off Masks," *Physica Status Solidi (A).* 136(1):K41-K45.
Weimann et al. (2001) "Four-Angle Evaporation Method for the Preparation of Single Electron Tunneling Devices," *Microelectron. Eng.* 57-58:915-918.
Whitten et al. (2007) "Free Standing Carbon Nanotube Composite Bio-electrodes." *J. Biomed. Mater. Res. B.* 82:37-43.

Wilson (2009) "A Decade of Step and Flash Imprint Lithography," *J. Photopolym. Sci. Technol.* 22(2):147-153.
Witte (2010) "The History of Biodegradable Magnesium Implants," *Acta. Biomater.* 6:1680-1692.
Witte et al. (2008) "Degradable Biomaterials Based on Magnesium Corrosion," *Current Opinion in Solid State and Materials Science.* 12:63-72.
Won et al. (2011) "Piezoresistive Strain Sensors and Multiplexed Arrays Using Assemblies of Single-Crystalline Silicon Nanoribbons on Plastic Substrates," *IEEE T. Electron. Dev.* 58(11):4074-4078.
Wu et al. (2008) "Biomolecule-Assisted Synthesis of Water-Soluble Silver Nanoparticles and Their Biomedical Applications," *Inorg. Chem.* 47:5882-5888.
Xia et al. (1998) "Soft Lithography," *Angew. Chem. Int. Ed.* 37:550-575.
Xu et al. (2002) "Nanoditches Fabricated Using a Carbon Nanotube as a Contact Mask," *Nano Lett.* 2(10):1061-1065.
Xu et al. (2004) "Fabrication of Free-Standing Metallic Pyramidal Shells," *Nano. Lett.* 4(12):2509-2511.
Xu et al. (2005) "Approaching Zero: Using Fractured Crystals in Metrology for Replica Molding," *J. Am. Chem. Soc.* 127(3):854-855.
Xu et al. (2007) "Fabrication of Large-Area Patterned Nanostructures for Optical Applications by Nanoskiving," *Nano Lett.* 7(9):2800-2805.
Xu et al. (2008) "Nanoskiving: A New Method to Produce Arrays of Nanostructures," *Account. Chem. Res.* 41(12):1566-1577.
Yamagata et al. (2003) "Preparation of a Copoly (dl-lactic/glycolic acid)-Zinc Oxide Complex and its Utilization to Microcapsules Containing Recombinant Human Growth Hormone," *International Journal of Pharmaceuticals.* 251:133-141.
Yan et al. (2006) "Magnesium Oxide as a Candidate High-$k$ Gate Dielectric," *Appl. Phys. Lett.* 88:142901.
Young et al. (1997) *Dietary Reference Intakes for Calcium, Phosphorus, Magnesium, Vitamin D, and Fluoride.* National Academy Press, Washington, D.C.
Yu et al. (2004) "Triangular Profile Imprint Molds in Nanograting Fabrication," *Nano Lett.* 4(2):341-344.
Zhang et al. (2010) "Fabrication and Comparative Study of Top-Gate and Bottom-Gate ZnO TFTs with Various Insulator Layers," *J. Mater. Sci.: Mater. Electron.* 21:671-675.
Zhao et al. (2002) "Novel Nano-Column and Nano-Flower Arrays by Glancing Angle Deposition," *Nano. Lett.* 2(4):351-354.
Zhao et al. (2004) "Synthesis and Properties of a Water-Soluble Single-Walled Carbon Nanotube-Poly(m-aminobenzene Sulfonic Acid) Graft Copolymer," *Adv. Funct. Mater.* 14(1):71-76.
Zhou et al. (2003) "Simple Fabrication of Molecular Circuits by Shadow Mask Evaporation," *Nano Lett.* 3(10):1371-1374.
Zhou et al. (2006) "Dissolving Behavior and Stability of ZnO Wires in Biofluids: A Study on Biodegradability and Biocompatibility of ZnO Nanostructures," *Adv. Mater.* 18:2432-2435.
Zhou et al. (2008) "Flexible Piezotronic Strain Sensor," *Nano. Lett.* 8(9):3035-3040.
Zhu et al. (2009) "Biocompatibility of Pure Iron: In Vitro Assessment of Degradation Kinetics and Cytotoxicity on Endothelial Cells," *Materials Science and Engineering C.* 29:1589-1592.

\* cited by examiner

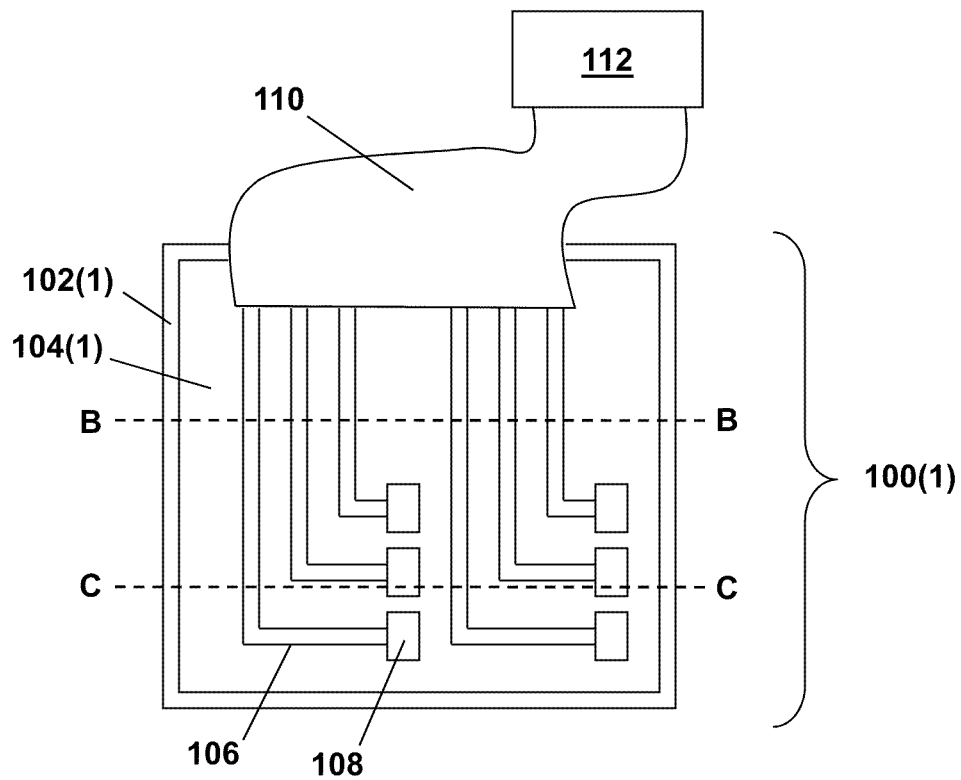
Fig. 1a
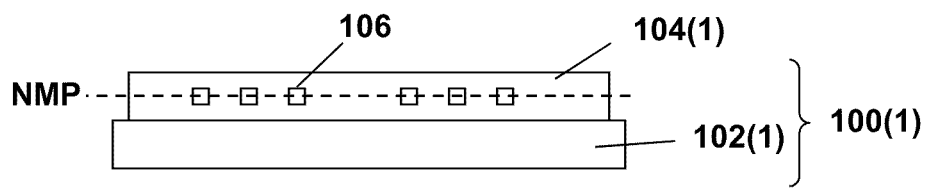
Fig. 1b
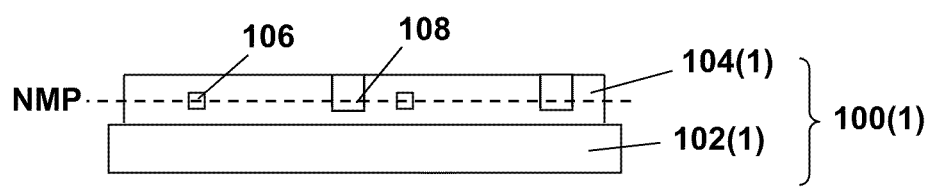
Fig. 1c
Figure 1

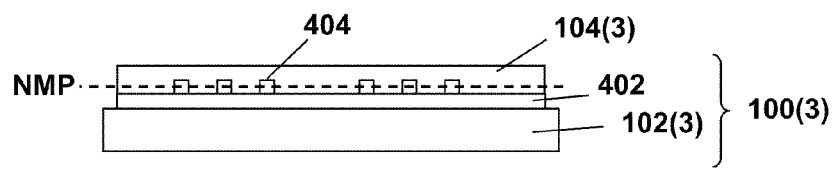
Figure 4
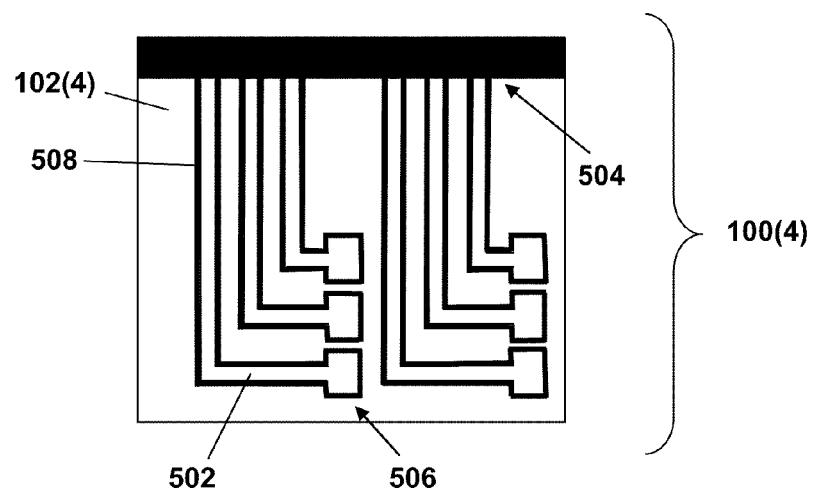
Fig. 5a
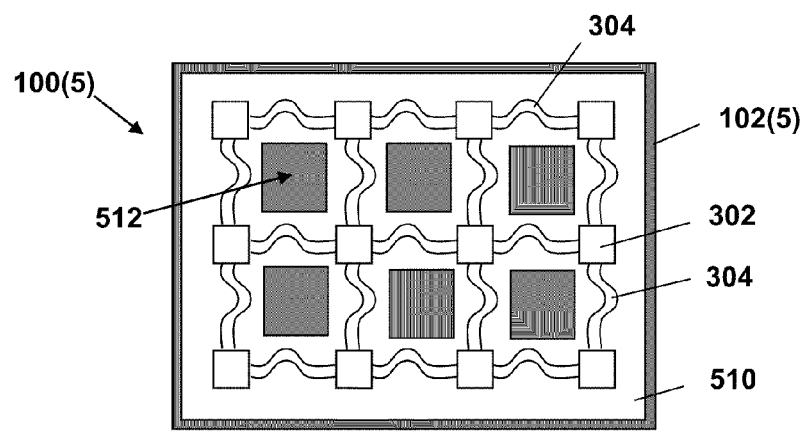
Fig. 5b
Figure 5

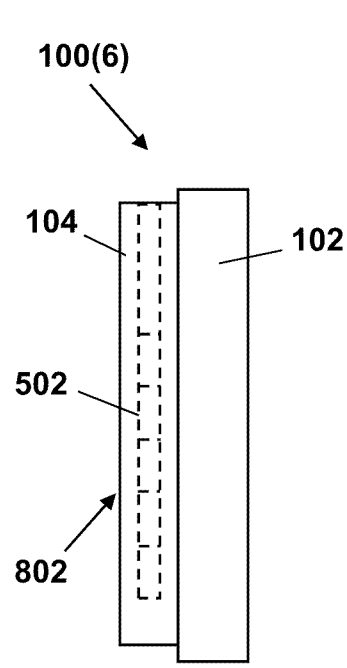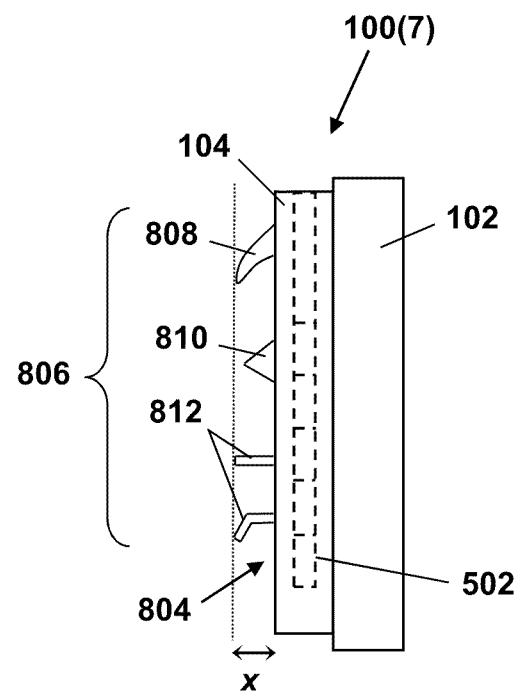
Fig. 8a  Fig. 8b
Figure 8

Fig. 9a
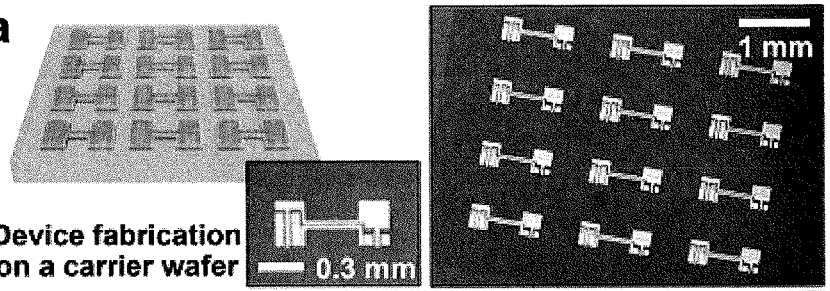
Fig. 9b
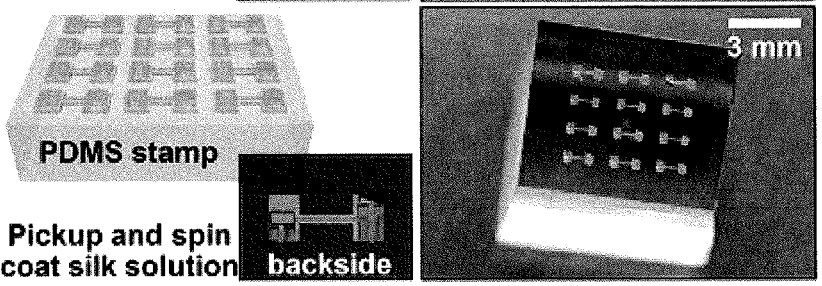
Fig. 9c
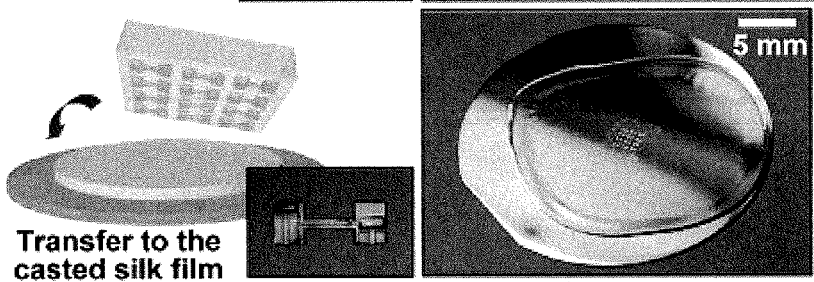
Fig. 9d
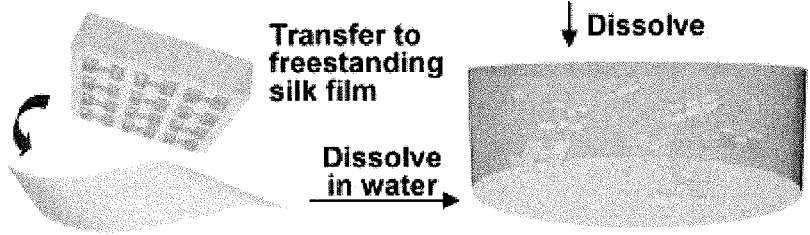
Figure 9

Fig. 10a
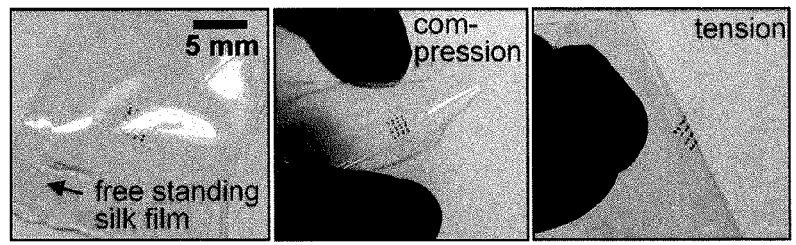
Fig. 10b
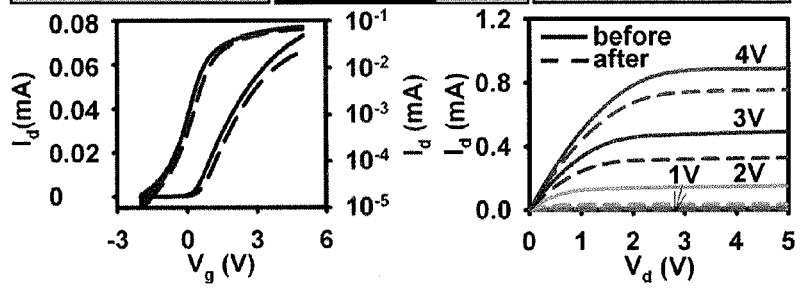
Figure 10
Fig. 11a
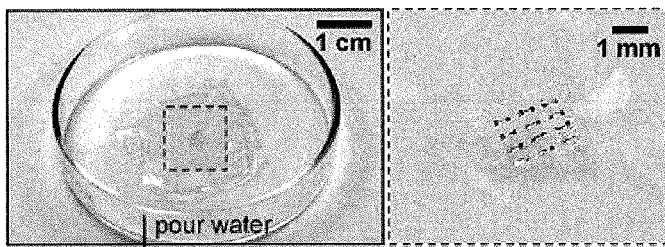
Fig. 11b
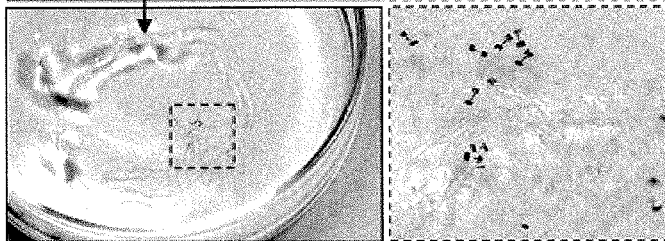
Fig. 11c
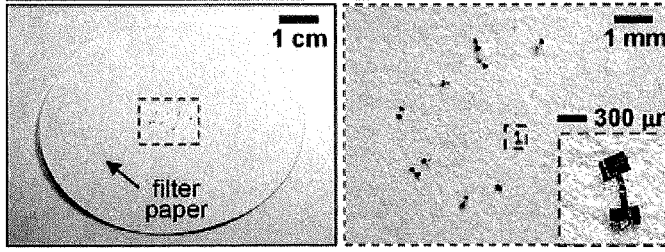
Figure 11

Fig. 13a
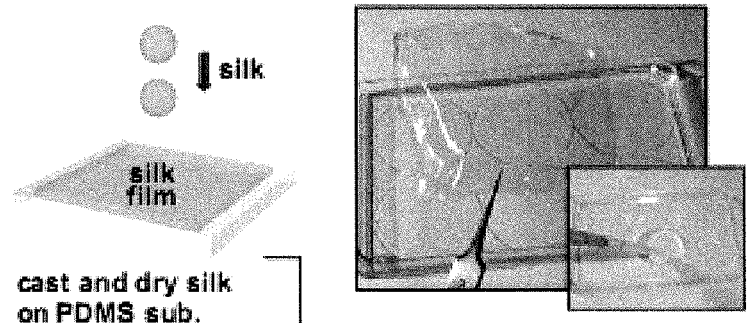
Fig. 13b
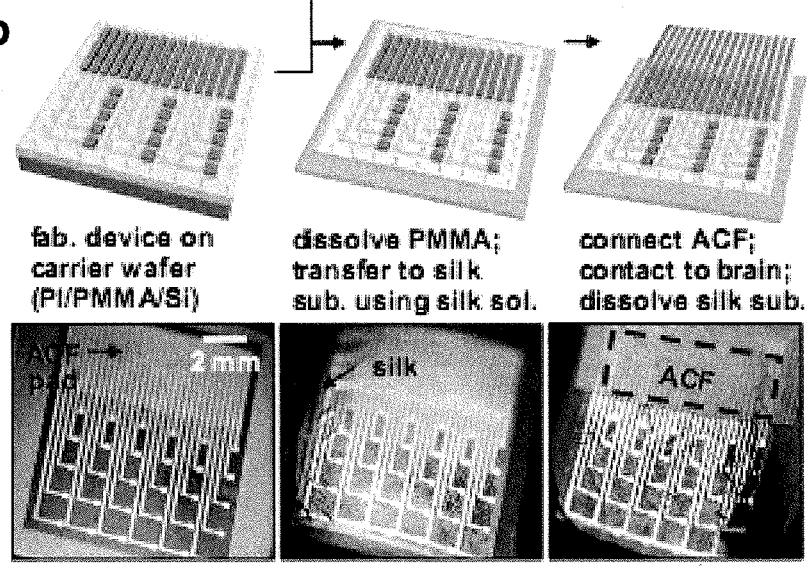
fab. device on carrier wafer (PI/PMMA/Si) → dissolve PMMA; transfer to silk sub. using silk sol. → connect ACF; contact to brain; dissolve silk sub.
Fig. 13c
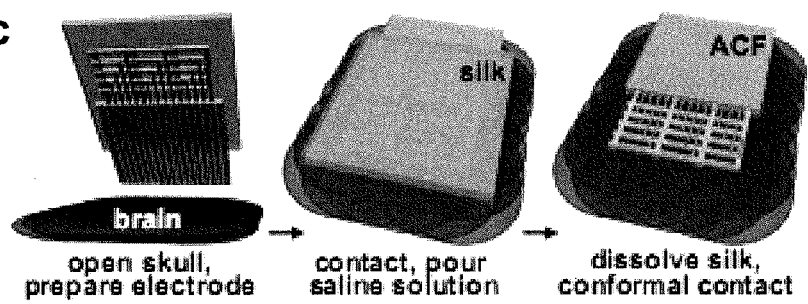
open skull, prepare electrode → contact, pour saline solution → dissolve silk, conformal contact
Figure 13

Fig. 14a Spin coat PDMS, attach Kapton film on glass

Fig. 14b Device fabrication, cut edge of kapton

Fig. 14c Detach from glass, connect ACF film

Fig. 15a
Fig. 15b
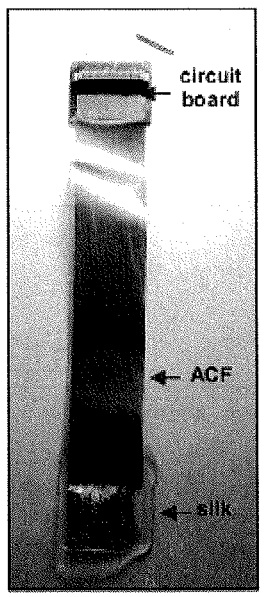
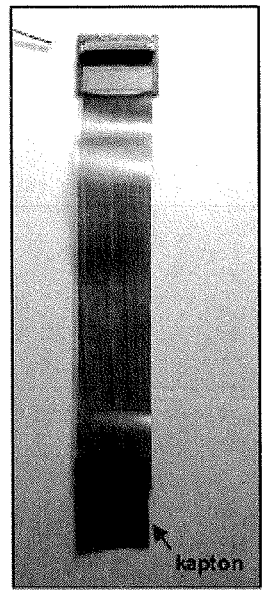
Figure 15

Fig. 20a
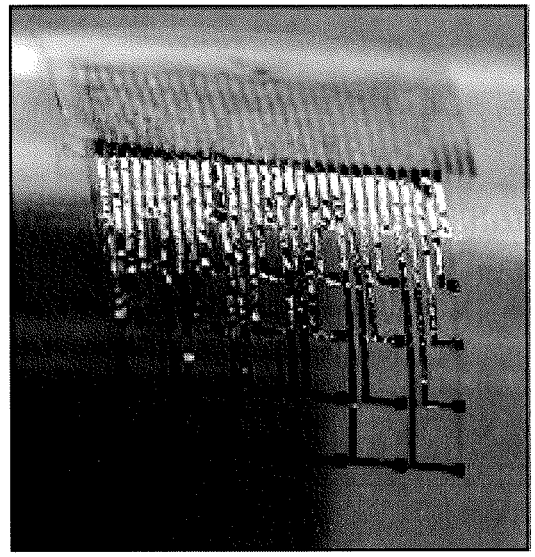
Fig. 20b
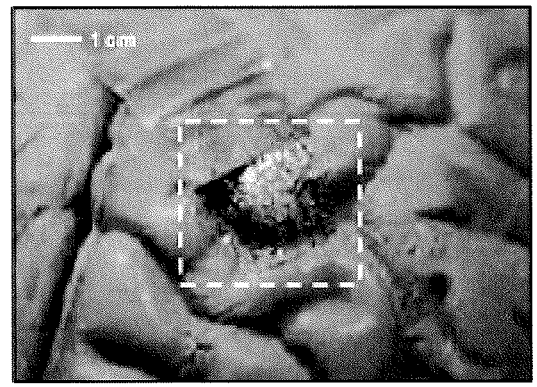
Figure 20

Fig. 21a 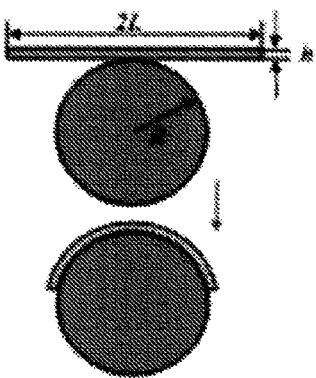 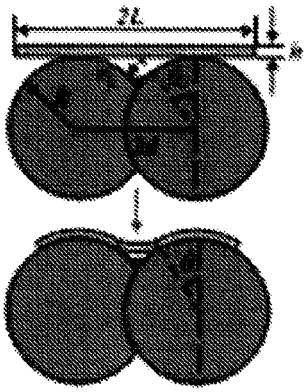 Fig. 21b
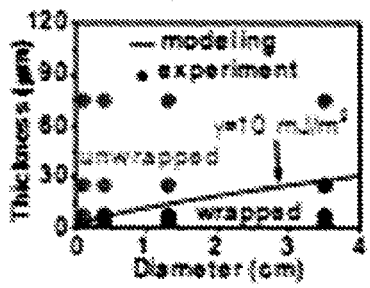 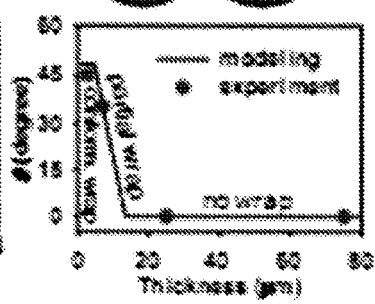

Figure 21

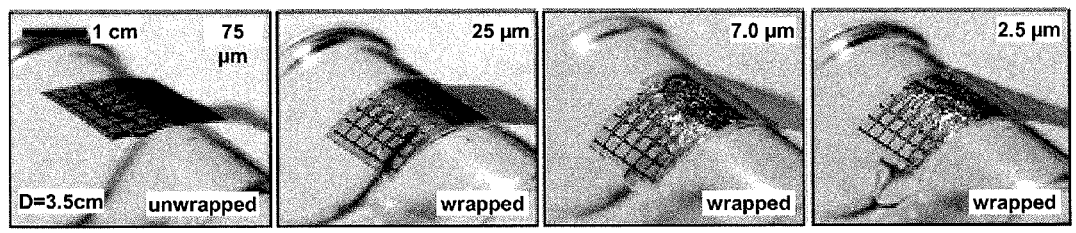
Fig. 22a
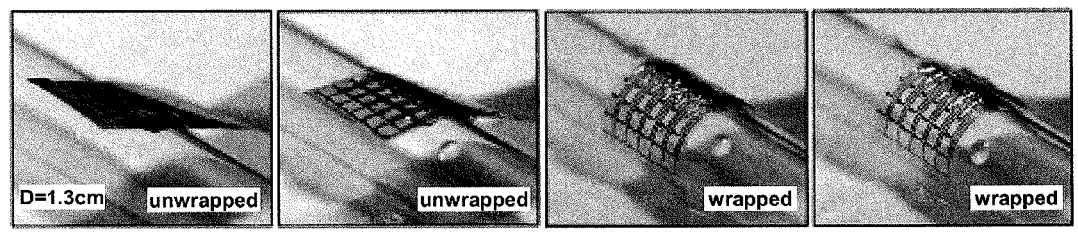
Fig. 22b
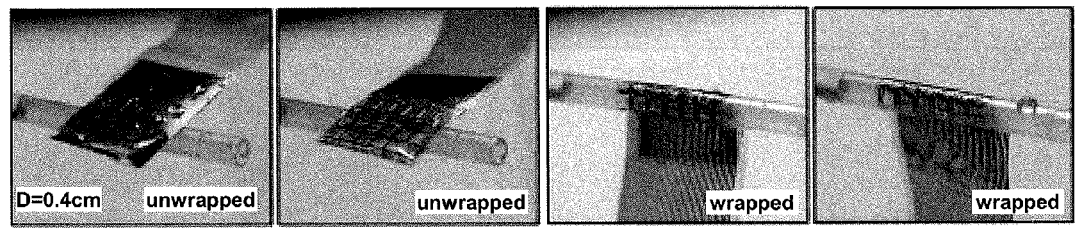
Fig. 22c
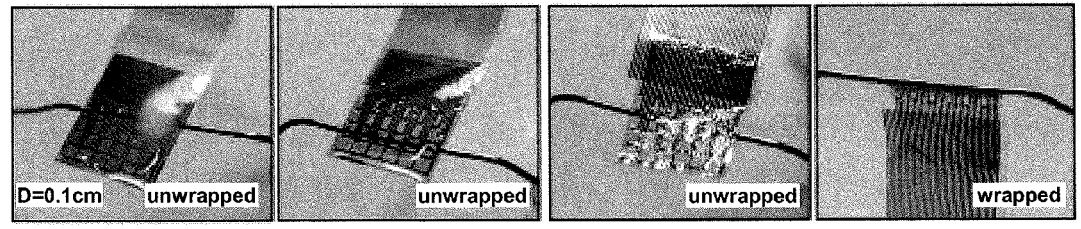
Fig. 22d
Figure 22

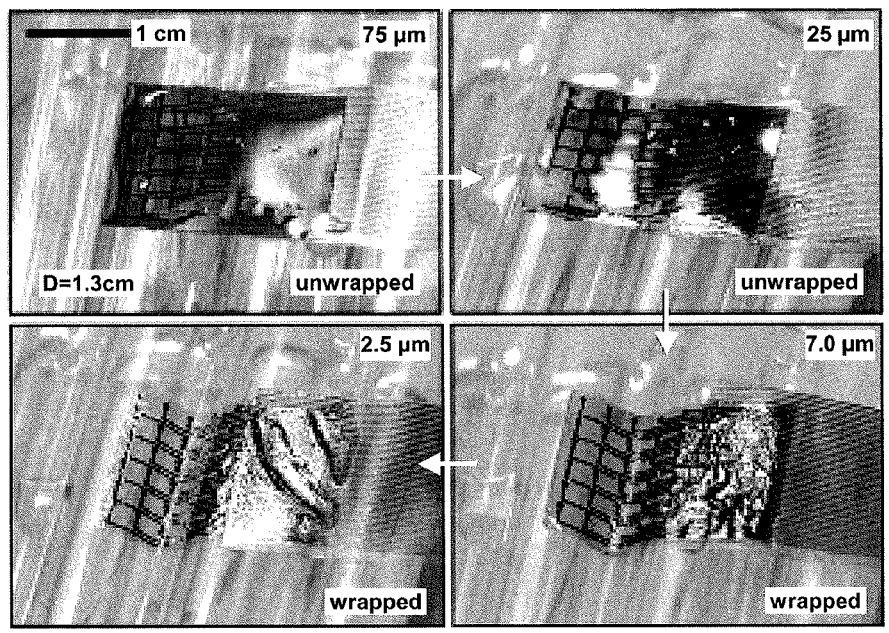
Fig. 23a
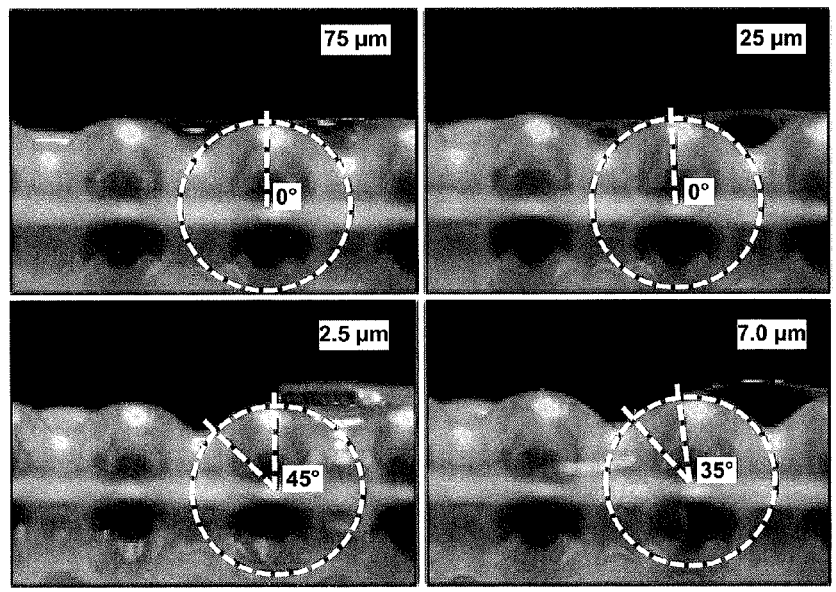
Fig. 23b
Figure 23

Figure 24

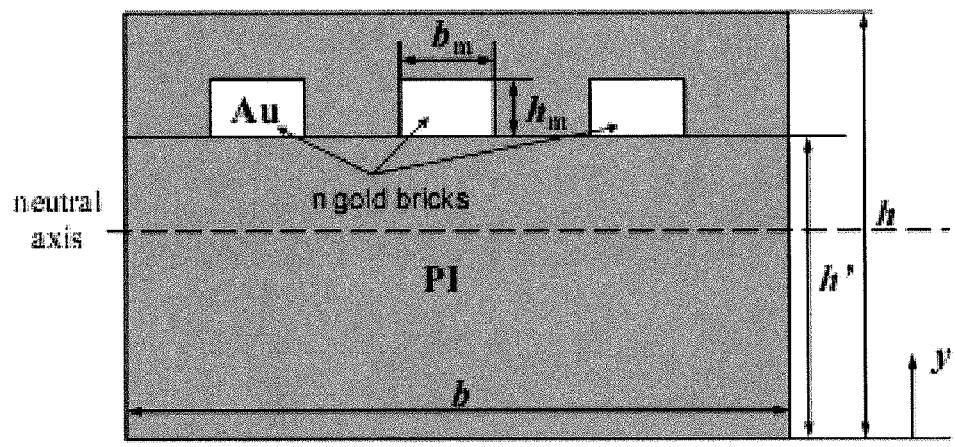
Fig. 26a
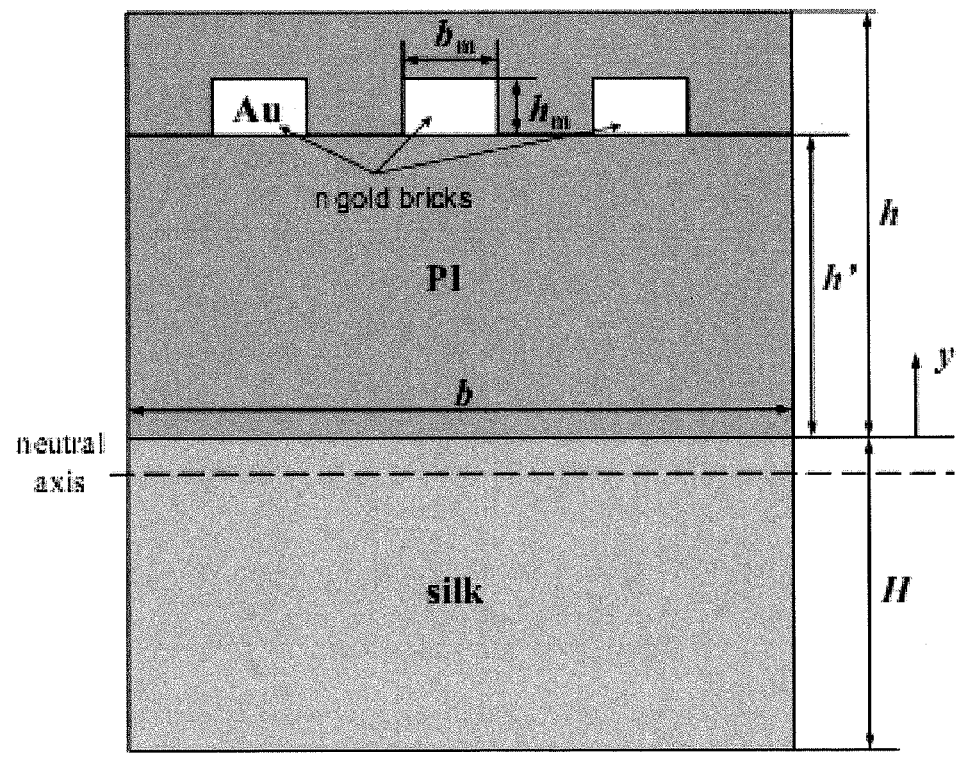
Fig. 26b
Figure 26 ic materials. International Patent Application Publication WO 2008/103464 discloses medical devices having nano-

IMPLANTABLE BIOMEDICAL DEVICES ON BIORESORBABLE SUBSTRATES

CROSS-REFERENCE TO RELATED APPLICATIONS

This application claims the benefit of priority of U.S. Provisional Patent Application No. 61/314,739, filed Mar. 17, 2010, which is hereby incorporated by reference in its entirety.

STATEMENT REGARDING FEDERALLY SPONSORED RESEARCH OR DEVELOPMENT

This invention was made with United States governmental support under Award Nos. DE-FG02-07ER46471 and DE-FG02-91ER45439 awarded by The U.S. Department of Energy, and by Contract No. W911 NF-07-1-0618 awarded by the U.S. Army Research Laboratory. The U.S. government has certain rights in the invention.

BACKGROUND

This invention is in the field of biomedical devices, and relates generally to implantable devices for sensing parameters associated with a target tissue and/or for actuating a target tissue. Methods for making, implanting, and using the implantable biomedical devices are provided.

Implantable biomedical devices have potential for a range of important clinical applications, such as treatment and/or monitoring of neurological disorders (e.g., epilepsy and Parkinson's disease), heart disorders (e.g., arrhythmias), vascular disorders, muscular and/or nerve disorders (e.g., as brain-computer interfaces for controlling prosthetics). Efficacious use of implantable biomedical devices, however, is dependent in part upon design strategies that provide compatibility between the hard, planar surfaces of conventional integrated circuits and medical devices and the soft, curvilinear tissues of biological systems. Overcoming this physical mismatch is important because differences in form traditionally lead to low fidelity coupling at the biotic/abiotic interface and limited long-term tissue health in connection with some conventional implantable devices.

Attempts to improve device-tissue coupling have in some cases sacrificed electronic performance by moving away from conventional silicon-based electronic components to amorphous silicon, organic or hybrid organic-inorganic semiconductors, which exhibit electronic properties, such as field effect mobilities, on/off ratios, etc., significantly inferior to corresponding single crystalline silicon-based devices. While such amorphous silicon and organic-based materials may be electronically inferior to singe crystalline silicon, they do have certain properties useful for biomedical applications, such as flexibility, chemically biocompatibility and, in some cases, biodegradability.

Recently, a number of patents and publications have disclosed implantable, biodegradable devices. For example, International Patent Application Publication WO 2008/085904 discloses biodegradable electronic devices that may include a biodegradable semiconducting material and a biodegradable substrate. International Patent Application Publication WO 2008/108838 discloses biodegradable devices for delivering fluids and/or biological material to tissue. International Patent Application Publication WO 2008/127402 discloses biodegradable sensors containing embedded biological materials. International Patent Application Publication WO 2008/103464 discloses medical devices having nanostructured surfaces, which are optionally coated with a biodegradable polymer. Similarly, International Patent Application Publication WO 99/45860 discloses devices having biocompatible, and optionally resorbable, substrates with projections that, depending on their spacing, either promote or discourage cell adhesion.

Other patents and publications have disclosed implantable electronic devices. For example, U.S. Pat. No. 5,403,700 discloses devices having polyimide substrates supporting patterned metal conductors. U.S. Pat. No. 7,190,051 discloses hermetically packaged and implantable electronics fabricated using silicon-on-insulator technology. International Patent Application Publications WO 2009/111641 and WO 2009/114689 disclose stretchable and flexible electronic devices and sensor arrays.

SUMMARY OF THE INVENTION

The invention provides devices and methods for implantable systems for biomedical applications, including in vivo sensing and/or actuating of tissue in a range of biological environments. In some embodiments, for example, implantable devices of the invention combine high performance single crystalline inorganic electronic materials and/or thin electrode arrays with bioresorbable substrates capable of at least partially resorbing upon contact with a target biological tissue. Incorporation of nanostructured single crystalline inorganic electronic materials and/or thin electrode arrays in some embodiments provides biocompatibility with a range of biological environments and provides mechanical properties (e.g., bending stiffness, Young's modulus, radius of curvature, etc.) and device attributes (e.g., flexibility, stretchability, etc.) useful for establishing conformal contact between the device and a target biological tissue. Incorporation of a bioresorbable substrate having a controllable and/or selectable resorption rate in some embodiments provides a biocompatible means of effectively deploying and interfacing the implantable device with a biological tissue of interest. In some embodiments, for example, at least partial resorption of the resorbable substrate establishes an interface providing for physical contact, electronic contact, thermal contact and/or optical communication between the device and a target biological tissue. In some embodiments, for example, devices of the present invention incorporate a highly biocompatible silk substrate providing useful and controllable resorption rates when provided in contact with a broad class of target tissues.

The invention enables a versatile tissue sensing and actuation platform supporting a class of implantable biomedical systems, materials and methods suitable for a broad range of biomedical applications, including sensing, electrochemical actuation, drug delivery and the treatment of disease. The combination of nanostructured single crystalline inorganic electronic materials or thin electrode arrays and bioresorbable substrates provides implantable systems that suppress, or entirely avoid, undesirable inflammation and/or immune responses upon implantation. Embodiments combining nanostructured single crystalline silicon or thin electrode arrays and silk resorbable substrates, and optionally a barrier layer having a mesh structure, provide implantable systems compatible with a broad class of tissue types, such as heart tissue, brain tissue, muscle tissue, nerve tissue, epithelial tissue or vascular tissue. In addition, the combination of nanostructured single crystalline inorganic electronic materials or thin electrode arrays and bioresorbable substrates provide implantable systems supporting a wide range of advanced device functionalities, including optical, electronic, electrochemical and chemical sensing and/or actuation.

Provided herein are implantable biomedical devices and methods of making and using implantable biomedical devices. For example, devices of the invention are useful for in vivo sensing of a parameter associated with a target tissue and/or biological environment, such as a chemical composition (e.g., pH, ionic strength, presence or concentration of a biomarker, protein, carbohydrate, etc.), an electrochemical parameter (e.g., current or voltage), temperature, and/or an optical parameter (e.g., absorption, scattering, etc.). For example, devices of the invention are useful for in vivo actuation of a target tissue in a biological environment such as electrochemical actuation, drug delivery, optical actuation etc. Also disclosed are methods of making an implantable biomedical device and methods of administering an implantable biomedical device onto a target tissue in a biological environment. When the implantable biomedical device is administered onto target tissue, a bioresorbable substrate of the implantable biomedical device at least partially resorbs into surrounding tissue of the biological environment, thereby allowing conformational changes to establish conformal contact and/or electrical contact and/or optical contact between the implantable biomedical device and the target tissue.

An implantable device of this aspect comprises a bioresorbable substrate; an electronic device comprising a plurality of inorganic semiconductor components or electrodes of an electrode array supported, directly or indirectly, by the bioresorbable substrate, where at least one of the inorganic semiconductor components has at least one physical dimension less than or equal to 100 microns, and a thin (e.g. thickness less than or equal to 100 microns) barrier layer having a mesh structure encapsulating at least a portion of the inorganic semiconductor components or electrodes of an electrode array, optionally entirely encapsulating the inorganic semiconductor components or electrodes of an electrode array. Optionally, the implantable device further comprises one or more additional substrate layers, such as one or more additional barrier layer or biocompatible layers, provided between the bioresorbable substrate and the inorganic semiconductor components to further provide encapsulation and/or selective electrical and/or chemical isolation of at least some of the inorganic semiconductor components.

In an embodiment, for example, provided is an implantable biomedical device for actuating a target tissue or sensing a parameter associated with the target tissue in a biological environment, the device comprising: (1) a bioresorbable substrate; (2) an electronic device comprising a plurality of inorganic semiconductor components supported by the bioresorbable substrate, wherein at least one of the inorganic semiconductor components has at least one physical dimension less than or equal to 100 microns; and (3) a barrier layer encapsulating at least a portion of the inorganic semiconductor components; wherein upon contact with the biological environment the bioresorbable substrate is at least partially resorbed, thereby establishing conformal contact between the implantable biomedical device and the target tissue in the biological environment. The implantable device of an aspect further comprises a biocompatible layer provided on the bioresorbable substrate, for example, provided between the bioresorbable substrate and at least a portion of the electronic device or components thereof. In an embodiment, the barrier layer and/or the biocompatible layer has mesh structure supporting and/or in physical contact with at least a portion of the inorganic semiconductor components of the device. In some embodiments, the electronic device is supported by, and in physical contact with, the bioresorbable substrate. In some embodiments, the electronic device is encapsulated by, and in physical contact with, the biocompatible layer and/or the barrier layer. In an embodiment, all of the inorganic semiconductor components have at least one physical dimension less than or equal to 100 microns.

In some embodiments, for example, the barrier layer, and optionally the biocompatible layer, function to encapsulate portions of, or all of, the electronic device, thereby preventing current leakage to the local biological environment and/or electrical shorting of the device. In an embodiment, the barrier layer and/or biocompatible layer encapsulates at least 50% of the inorganic semiconductor components of the device, optionally at least 90% of the inorganic semiconductor components of the device, and optionally all of the inorganic semiconductor components of the device. Optionally, the implantable device further comprises one or more electrodes in electrical contact with at least a portion of the semiconductor components, for example electrodes comprising a biocompatible or bioresorbable metal and/or electrodes at least partially, and optionally entirely, encapsulated by the barrier layer, bioresorbable substrate and/or the biocompatible layer.

In an embodiment, for example, provided is an implantable biomedical device for actuating a target tissue or sensing a parameter associated with the target tissue in a biological environment, the device comprising: an electrode array comprising a plurality of individually addressable metal electrodes, wherein each metal electrode has at least one physical dimension less than or equal to 100 microns; a barrier layer having a mesh structure, wherein the barrier layer at least partially supports the electrode array; and a bioresorbable substrate supporting the electrode array, the barrier layer or both of the electrode array and the barrier layer; wherein upon contact with the biological environment the bioresorbable substrate is at least partially resorbed, thereby establishing conformal contact between the electrode array and the target tissue in the biological environment. In an embodiment, at least a portion, and optionally all of, the electrodes of the electrode array are physically separated from each other. In an embodiment, the barrier layer is in physical contact with at least a portion of the electrode array, and optionally in physical contact with each of the electrodes of the array. In an embodiment, the bioresorbable substrate is in physical contact with at least a portion of the electrode array and/or in physical contact with at least a portion of the barrier layer. In an embodiment, each of the electrodes of the array is in electrical contact with at least one electronic interconnect, optionally configured for receiving and/or transmitting electronic signals to/from the individually addressable electrodes of the array.

Devices of this aspect are useful generally for in vivo biomedical applications including sensing, actuating, imaging and/or delivery of therapeutic agents to a local biological environment. In an embodiment, for example, devices of the invention are useful for making electrophysiology measurements of a target tissue in a biological environment or for electrophysically actuating a target tissue in a biological environment, where the biological environment may be an in-vivo biological environment, and where the target tissue may be selected from, but not limited to, heart tissue, brain tissue, muscle tissue, nerve tissue, epithelial tissue and vascular tissue.

Resorption of the bioresorbable substrate is useful for deploying, or otherwise positioning, manipulating and/or interfacing, the electronic device (e.g., a surface, a portion and/or component thereof) in a given biological environment. In some embodiments, for example, the electronic device is brought into conformal contact with a target tissue by a process involving resorption of the resorbable substrate, for example, wherein the resorption process brings the electronic device in contact (e.g., physical, electrical, thermal, etc.) with the target tissue, and optionally wherein the resorption process causes conformal and/or morphological changes to the electronic device that assists in interfacing the device with the target tissue. In some embodiments, the device is deployed in, or otherwise positioned, manipulated and/or interfaced with, a biological environment via a process involving complete resorption of the bioresorbable substrate, for example, so as to provide the electronic device in physical contact, electrical contact or optical communication with a target tissue. In some embodiments of this aspect, therefore, the resorbable layer functions as a sacrificial layer during deployment so as to facilitate interfacing the electronic device with the target tissue. Alternatively, in other embodiments, the device is deployed in, or otherwise positioned, manipulated and/or interfaced with, a biological environment via a process involving partial, but not complete, resorption of the bioresorbable substrate, for example, so as to provide the electronic device in physical contact, electrical contact or optical communication with a target tissue. In some embodiments of this aspect, therefore, the resorbable layer functions as a partial sacrificial layer during deployment but remains as a structural and/or functional component of the device during use. In the present devices and methods, resorption of the bioresorbable substrate provides a minimally invasive and/or biocompatible approach to establishing conformal contact, and optionally physical contact, conformal contact, thermal contact and/or electrical contact, between the electronic device and the target tissue. In some embodiments, for example, partial or complete resorption of the bioresorbable substrate provides a means of selectively adjusting and/or manipulating the physical dimensions, conformation, morphology and/or shape of the electronic device so as to facilitate establishing conformal contact with a target tissue. In some embodiments, partial or complete resorption of the bioresorbable substrate provides a means of selectively adjusting the chemical composition of the implantable device so as to establish conformal contact with a target tissue in a biocompatible manner, such as in a manner suppressing undesirable immune response and/or inflammation.

Incorporation of resorbable materials in the present invention may also be implemented in a manner to facilitate removal, biological degradation and/or clearance of the present implantable devices and components thereof. In an embodiment, a device of the invention has a composition, geometry and/or physical dimensions such that upon at least partial resorption of the bioresorbable substrate the device is broken up into fragments that are efficiently processed and cleared by a subject. In an embodiment, for example, the device is configured such that upon at least partial resorption of the bioresorbable substrate the device is broken up into fragments having lateral and thickness dimensions less than 100 microns, optionally less than 10 microns and optionally less than 1 micron, so as to facilitate processing and clearance of the device by a subject. Alternatively, the invention includes implantable devices having electronic device components that remain essentially intact (e.g., at least 70% intact or optionally at least 90% intact) upon at least partial resorption of the bioresorbable substrate, and optionally upon complete resorption. Embodiments of this aspect of the invention are useful for biomedical applications wherein the device is designed so as to be removable via a surgical procedure. In an aspect, for example, the electronic device component exhibits physical dimensions and/or mechanical properties (e.g., rigidity, hardness, Young's modulus, etc.) after at least partial resorption of the bioresorbable substrate such that the device may be physically removed after implantation (e.g., by a surgeon).

A variety of materials are useful for the bioresorbable substrate of the present devices, including materials that are efficiently processed and/or remodeled without formation of biologically active, toxic and/or harmful byproducts upon contact with a biological environment. Useful materials for the bioresorbable substrate include, for example, a biopolymer (e.g., protein, peptide, carbohydrate, polynucleotide, etc.), a synthetic polymer, a protein, a polysaccharide, silk, poly(glycerol-sebacate) (PGS), polydioxanone, poly(lactic-co-glycolic acid) (PLGA), polylactic acid (PLA), collagen, chitosan, fibroin, and combinations of these. Useful silk materials for bioresorbable substrates include, for example, silkworm fibroin, modified silkworm fibroin, spider silk, insect silk, recombinant silk, and any combination of these. As used herein, modified silkworm fibroin refers to a polymer composition that is derived via chemical modification of silkworm fibroin.

The physical dimensions and physical properties of the bioresorbable substrate are important parameters for supporting a range of device functionalities and compatibility with different tissue types. In some embodiments, the bioresorbable substrate has a thickness less than or equal to 10,000 µm, and optionally in some embodiments less than or equal to 1000 µm, and optionally in some embodiments less than or equal to 100 µm, and optionally in some embodiments less than or equal to 10 µm; and optionally in some embodiments less than or equal to 1 µm. Use of a thin bioresorbable substrate (e.g., thickness less than or equal to 100 microns, optionally less than or equal to 10 microns and optionally less than or equal to 1 micron) is useful for providing a flexible, or otherwise deformable, implantable device capable of establishing conformal contact with a wide range of tissue types, including tissues having complex, highly contoured surfaces. In some embodiments, the bioresorbable substrate has a thickness selected over the range of 100 nanometers and 10000 µm, optionally for some applications selected over the range of 1 µm and 1000 µm, and optionally for some embodiments selected over the range of 1 µm and 10 µm. In some embodiments, the composition and physical properties (e.g., Young's modulus, net bending stiffness, toughness, etc.) of the bioresorbable substrate are selected to provide sufficient structural support for the electronic device component, while also providing an ability to achieve a high degree of conformal contact upon deployment. In some embodiments, the bioresorbable substrate is a low modulus layer. Alternatively, the invention includes devices having a bioresorbable substrate that is a high modulus layer. In some embodiments, for example, the bioresorbable substrate has a Young's modulus less than or equal to 10 GPa, preferably for some applications a Young's modulus less than or equal to 100 MPa, optionally for some applications less than or equal to 10 MPa. In some embodiments, for example, the bioresorbable substrate has a Young's modulus selected over the range of 0.5 MPa and 10 GPa, and optionally for some applications selected over the range of 0.5 MPa and 100 MPa, and optionally for some applications selected over the range of 0.5 MPa and 10 MPa. In some embodiments, for example, the bioresorbable substrate has a net bending stiffness less than or equal to $1 \times 10^9$ GPa µm$^4$, optionally for some applications less than or equal to $1 \times 10^7$ GPa µm$^4$ and optionally for some applications less than or equal to $1 \times 10^6$ GPa µm$^4$. In some embodiments, for example, the bioresorbable substrate has a net bending stiffness selected over the range of $0.1 \times 10^4$ GPa µm$^4$ and $1 \times 10^9$ GPa µm$^4$, and optionally for some applications between 0.1× 10$^4$ GPa µm$^4$ and 5×10$^5$ GPa µm$^4$.

In some embodiments, the device includes a bioresobable substrate having a controllable and/or selectable in vivo resorption rate when provided in contact with a target tissue in a biological environment. The invention includes implantable devices having bioresorbable substrates exhibiting a range of resorption rates that are selected on the basis of an intended biological application, device functionality, tissue type, etc. In some embodiments, for example, the bioresorbable substrate exhibits a large resorption rate in vivo so as to provide rapid and complete resorption upon administration, for example, to facilitate interfacing the device with a target tissue and/or to facilitate conformational and/or morphological changes useful for deploying the device in a particular tissue environment. In other embodiments, for example, the bioresorbable substrate exhibits a small resorption rate in vivo so as to provide slow and incomplete resorption upon administration, for example, to provide encapsulation of the electronic components of the device and/or to provide structural properties useful for deploying or removing the device.

In some biological environments, such as an in vivo biological environment, the degradation of the bioresorbable substrate occurs via enzymatic degradation, for example, via protease mediated degradation. In addition, degradation occurs in some embodiments from the surfaces of the bioresorbable substrate that are exposed to the biological environment having degradation enzymes present, such as at the interface with a tissue and/or biological fluid. Accordingly, certain parameters of the bioresorbable substrate may be selected to effectively control the resorption rate. In an embodiment, the chemical composition, physical state and/or thickness of the bioresorbable substrate is selected so as to control the resorption rate. In an embodiment, for example, the bioresorbable substrate comprises a biopolymer exhibiting a useful resorption rate for a selected biological environment, such as a silk biopolymer exhibiting a useful resorption rate. The invention includes bioresorbable substrates comprising amorphous materials, crystalline materials, partially amorphous materials and partially crystalline materials. In an embodiment, the implantable device of the invention includes an at least partially crystalline material, wherein the extent of crystallinity of the bioresorbable substrate is selected to provide a useful and/or preselected resorption rate for a selected biological environment and device application. In some embodiments, the larger the degree of crystallinity of the bioresorbable substrate the slower the resorption rate when provided in contact with the target tissue. For example, the invention includes implantable devices having a bioresorbable substrate with a degree of crystallinity less than or equal to 55%, and optionally a degree of crystallinity less than or equal to 30% and optionally a degree of crystallinity less than or equal to 20%, and optionally a degree of crystallinity less than or equal to 5%. For example, the invention includes implantable devices having a bioresorbable substrate with a degree of crystallinity selected over the range of 0 to 55%, and optionally for some embodiments a degree of crystallinity selected over the range of 1 to 30%, and optionally for some embodiments a degree of crystallinity selected over the range of 5 to 20%. As used herein, 0% crystallinity refers to an entirely amorphous material and the given degree of crystallinity corresponds to the amount of a material provided in a crystalline state relative to the total amount of material. In some embodiments, for example those having a silk bioresorbable substrate, the degree of crystallinity refers to the beta sheet content of the silk bioresorbable substrate.

Bioresorbable substrates for some applications are biocompatible materials that are processed and/or remodeled upon contact with a target tissue without formation of biologically active, toxic and/or harmful byproducts.

The geometry and/or morphology of the bioresorbable substrate are other characteristics important to establishing the functional capabilities of the present implantable devices. In an embodiment, the bioresorbable substrate is a continuous layer having approximately uniform thickness (e.g., thicknesses within 10% of average thickness of the layer). Alternatively, the invention includes devices having a bioresobable substrate comprising a discontinuous layer and/or a layer having a nonuniform thickness profile. The invention includes implantable devices having additional bioresorbable substrates and/or layers, for example, for partial or full encapsulation and/or electronic isolation of electronic device components (e.g., semiconductors, electrodes, dielectrics, etc.).

In some embodiments, the bioresorbable substrate and/or barrier layer and/or second dielectric layer has a planar or non-planar (e.g., curved, concave, convex, etc.) contact surface for physically contacting the surface of a target tissue. Such embodiments are useful, for example, for providing sensing and/or actuation at the surface of a target tissue. In other embodiments, the bioresorbable substrate and/or barrier layer and/or second dielectric layer has a nanostructured or microstructured contact surface for physically contacting the target tissue. Nanostructured or microstructured contact surfaces for some applications comprise a plurality of relief features that physically contact and/or penetrate the surface of a target tissue. In some embodiments, the relief features extend from a surface of the bioresorbable substrate and/or barrier layer and/or second dielectric layer a length selected from the range of 10 nanometers to 1000 nanometers and preferably for some applications selected from the range of 10 nanometers to 500 nanometers. Useful relief features include, but are not limited to, barbs, spikes, columns, protrusions and any combination of these. Devices having a nanostructured bioresobable layer are useful in some embodiments for providing sensing and/or actuation below the surface of a target tissue and/or within the target tissue.

In some embodiments, at least a portion, and optionally all, of the plurality of inorganic semiconductor components of the electronic device is bonded to the bioresorbable substrate, barrier layer and/or the biocompatible layer. Bonding between the electronic device and the bioresorbable substrate, barrier layer and/or the biocompatible layer may be achieved directly involving covalent and noncovalent bonding (e.g., Van der Waals forces, hydrogen bonding, London dispersion forces, etc.) between layers and materials. Alternatively, bonding may be achieved by incorporation of an adhesive layer provided between the electronic device and the bioresorbable substrate, barrier layer and/or the biocompatible layer. Useful adhesive layers for bonding comprise a polymer, an elastomer (e.g. PDMS), a prepolymer, a thin metal layer, a silk layer, etc.

The implantable biomedical device has a neutral mechanical plane and, in some embodiments, at least a portion, and optionally all, of the plurality of semiconductor components or electrodes of the electrode array is positioned proximate (e.g., within 10 microns, and optionally within 1 micron) to the neutral mechanical plane. A thickness of the barrier layer and a thickness of the bioresorbable substrate may be selected so as to position at least a portion of the plurality of semiconductor components or electrodes of the electrode array proximate to the neutral mechanical plane. Embodiments having semiconductor components or electrodes of the electrode array positioned proximate to the neutral mechanical plane are useful for applications wherein the device undergoes a significant change in conformation upon deployment, for example, by enhancing the structural integrity of the device when provided in a non-planar (e.g., bent, curved, convex, concave, etc.) conformation and/or in a stretched conformation.

Useful inorganic semiconductor components include, but are not limited to, flexible semiconductor structures, stretchable semiconductor structures and/or semiconductor structures capable of undergoing a change in shape so as to conform to the surface of a target tissue. In an embodiment, for example, the inorganic semiconductor components comprises a microstructured material or a nanostructured material such as a nanoribbon, a nanomembrane, or a nanowire. As used herein, the term "microstructured" refers to a structure having at least one physical dimension selected over the range of 1 micron to 1000 microns and the term "nanostructured" refers to a structure having at least one physical dimension selected over the range of 10 nanometers to 1000 nanometers. In an embodiment, the inorganic semiconductor elements comprise a semiconductor device such as a transistor, a transistor channel, a diode, a p-n junction, a photodiode, a light emitting diode, a laser, an electrode, an integrated electronic device or combinations and/or arrays of these.

The physical dimensions and shape of the electronic device, and components thereof, and of the implantable device are important parameters for establishing adequate conformal contact between the implantable biomedical device and the target tissue and for minimizing immunological responses to the device, such as minimizing inflammation upon contact with a target tissue. Use of thin inorganic semiconductor components (e.g., thickness less than or equal to 100 microns, optionally less than or equal to 10 microns and optionally less than or equal to 1 micron) is useful for providing a flexible, or otherwise deformable, implantable device capable of establishing conformal contact with a wide range of tissue types, including tissues having complex, highly contoured surfaces. In some embodiments, at least some of, and optionally all of, the inorganic semiconductor components of the electronic device have a thickness less than or equal to 100 microns, and for some applications have a thickness less than or equal to 10 microns, and for some applications have a thickness less than or equal to 1 micron, and for some applications have a thickness less than or equal to 500 nanometers, and for some applications have a thickness less than or equal to 100 nanometers. In some embodiments, at least some of, and optionally all of, the inorganic semiconductor components of the electronic device have a thickness selected from a range of 50 nm to 100 µm, optionally for some applications selected from a range of 50 nm to 10 µm, and optionally for some applications selected from a range of 100 nm to 1000 nm. In some embodiments, at least some of, and optionally all of, the inorganic semiconductor components of the electronic device have lateral physical dimensions (e.g., length, width, diameter, etc.) less than or equal to 10000 µm, and for some applications have lateral physical dimensions less than or equal to 1000 µm, and for some applications have lateral physical dimensions less than or equal to 100 µm, and for some applications have lateral physical dimensions less than or equal to 1 µm. In some embodiments, at least some of, and optionally all of, the inorganic semiconductor components of the electronic device have lateral physical dimensions selected from the range of 100 nm to 10000 µm, optionally for some applications selected from a range of 500 nm to 1000 µm, optionally for some applications selected from a range of 500 nm to 100 µm, and optionally for some applications selected from a range of 500 nm to 10 µm.

As with other components of the implantable biomedical device, the physical properties of the inorganic semiconductor components (e.g., Young's modulus, net bending stiffness, toughness, etc.) allow the implantable biomedical device to achieve a high degree of conformal contact with a target tissue. In some embodiments, for example, at least a portion, and optionally all, of the inorganic semiconductor components of the electronic device have a Young's modulus less than or equal to 10 GPa, optionally for some applications less than or equal to 100 MPa, optionally for some applications less than or equal to 10 MPa. In some embodiments, for example, at least a portion, and optionally all, of the inorganic semiconductor components of the electronic device have a Young's modulus selected over the range of 0.5 MPa and 10 GPa, and optionally for some applications selected over the range of 0.5 MPa and 100 MPa, and optionally for some applications selected over the range of 0.5 MPa and 10 MPa. In some embodiments, at least a portion, and optionally all, of the inorganic semiconductor components of the electronic device have a net bending stiffness less than or equal to $1\times10^8$ GPa µm$^4$, optionally for some applications less than or equal to $5\times10^5$ GPa µm$^4$ and optionally for some applications less than or equal to $1\times10^5$ GPa µm$^4$. In some embodiments, at least a portion, and optionally all, of the inorganic semiconductor components of the electronic device have a net bending stiffness selected over the range of $0.1\times10^4$ GPa µm$^4$ and $1\times10^8$ GPa µm$^4$, and optionally for some applications between $0.1\times10$ GPa µm$^4$ and $5\times10^5$ GPa µm$^4$.

In some embodiments, the electronic device, or components thereof, are assembled on the bioresorbable substrate via a printing-based or molding-based process, for example, by transfer printing, dry contact transfer printing, solution-based printing, soft lithography printing, replica molding, imprint lithography, etc. In some of these embodiments, therefore, the electronic device, or components thereof, comprise printable semiconductor materials and/or devices. Integration of the electronic device and bioresorbable substrate components via a printing-based technique is beneficial in some embodiments, as it allows for independent processing of semiconductor devices/materials and processing for the bioresorbable substrate. For example, the printing-based assembly approach allows semiconductor devices/materials to be processed via techniques that would not be compatible with some bioresorbable substrates. In some embodiments, for example, the semiconductor device/materials are first processed via high temperature processing, physical and chemical deposition processing, etching and/or aqueous processing (e.g. developing, etc.), and then subsequently assembled on the bioresorbable substrate via a printing-based technique. An advantage of this approach is that it avoids processing of the semiconductor device/materials on the bioresorbable substrate in a manner that could negatively impact the chemical and/or physical properties of the bioresorbable substrate, for example, by negatively impacting biocompatibility, toxicity and/or the resorption properties (e.g., resorption rate, etc.) of the bioresorbable substrate. In some embodiments, for example, this approach allows for effective fabrication of the electronic device without exposing the bioresorbable substrate to aqueous processing, for example, processing involving exposure of the bioresorbable substrate to an etchant, a stripper or a developer.

Useful materials for the inorganic semiconductor components include high quality semiconductor materials such as single crystalline semiconductor materials including pure and doped single crystalline semiconductor materials. Integration of single crystalline semiconductor materials into an implantable biomedical device is particularly beneficial for providing implantable devices exhibiting very good electronic properties. In an embodiment, the semiconductor components comprise a material selected from the group consisting of Si, Ge, Se, diamond, fullerenes, SiC, SiGe, SiO, $SiO_2$, SiN, AlSb, AlAs, AlIn, AlN, AlP, AlS, BN, BP, BAs, $As_2S_3$, GaSb, GaAs, GaN, GaP, GaSe, InSb, InAs, InN, InP, CsSe, CdS, CdSe, CdTe, $Cd_3P_2$, $Cd_3As_2$, $Cd_3Sb_2$, ZnO, ZnSe, ZnS, ZnTe, $Zn_3P_2$, $Zn_3As_2$, $Zn_3Sb_2$, $ZnSiP_2$, CuCl, PbS, PbSe, PbTe, FeO, $FeS_2$, NiO, EuO, EuS, PtSi, TlBr, $CrBr_3$, SnS, SnTe, $PbI_2$, $MoS_2$, GaSe, CuO, $Cu_2O$, HgS, HgSe, HgTe, $HgI_2$, MgS, MgSe, MgTe, CaS, CaSe, SrS, SrTe, BaS, BaSe, BaTe, $SnO_2$, TiO, $TiO_2$, $Bi_2S_3$, $Bi_2O_3$, $Bi_2Te_3$, $BiI_3$, $UO_2$, $UO_3$, $AgGaS_2$, PbMnTe, $BaTiO_3$, $SrTiO_3$, $LiNbO_3$, $La_2CuO_4$, $La_{0.7}Ca_{0.3}MnO_3$, CdZnTe, CdMnTe, $CuInSe_2$, copper indium gallium selenide (CIGS), HgCdTe, HgZnTe, HgZnSe, PbSnTe, $Tl_2SnTe_5$, $Tl_2GeTe_5$, AlGaAs, AlGaN, AlGaP, AlInAs, AlInSb, AlInP, AlInAsP, AlGaAsN, GaAsP, GaAsN, GaMnAs, GaAsSbN, GaInAs, GaInP, AlGaAsSb, AlGaAsP, AlGaInP, GaInAsP, InGaAs, InGaP, InGaN, InAsSb, InGaSb, InMnAs, InGaAsP, InGaAsN, InAlAsN, GaInNAsSb, GaInAsSbP, and any combination of these. In some embodiments, the inorganic semiconductor components include a material selected from the group consisting of Si, SiC, SiGe, SiO, $SiO_2$, SiN, and any combination of these. In some embodiments, the inorganic semiconductor components comprise single crystalline silicon, porous silicon and/or polycrystalline silicon. In some embodiments, the inorganic semiconductor component comprises a single crystal inorganic semiconductor material. In some embodiments, the inorganic semiconductor component is a bioresorbable material or a bioinert material. Useful materials for a bioresorbable, inorganic semiconductor component include, but are not limited to, porous silicon, polycrystalline silicon, and any combination of these.

In some embodiments, electronic devices of this aspect comprise one or more interconnected island and bridge structures. For example, an island structure may comprise one or more semiconductor circuit components of the electronic device. A bridge structure may comprise one or more flexible and/or stretchable electrical interconnections providing electrical communication between elements, for example between different island structures. In this manner, electronic devices of the present invention may comprise stretchable electronic devices having a plurality of electrically interconnected inorganic semiconductor components comprising one or more island structures and one or more flexible and/or stretchable bridge structures providing electrical interconnection; e.g., stretchable electronic interconnects.

In some embodiments, the electronic device may include one or more additional device components selected from the group consisting of an electrode, a dielectric layer, a chemical or biological sensor element, a pH sensor, an optical sensor, an optical source, a temperature sensor, and a capacitive sensor. The additional device component may comprise a bioinert material or a bioresorbable material. Useful bioinert materials include, but are not limited to, titanium, gold, silver, platinum, and any combination of these. Useful bioresorbable materials include, but are not limited to, iron, magnesium, and any combination of these.

In some embodiments, at least a portion of the plurality of inorganic semiconductor components comprise one or more of an amplifier circuit, a multiplexing circuit, a current limiting circuit, an integrated circuit, a transistor or a transistor array. Useful multiplexing circuits include those configured to individually address each of a plurality of electrodes spatially arranged over the bioresorbable substrate.

The physical dimensions, composition and geometry of electrodes are important parameters of implantable electrode arrays and electronic devices of the invention. In an embodiment, the electrodes of the electrode array are metal films, for example thin (e.g., thickness <100 microns) metal films. Use of thin electrodes (e.g., thickness less than or equal to 100 microns, optionally less than or equal to 10 microns and optionally less than or equal to 1 micron) is useful for providing a flexible, or otherwise deformable, implantable device capable of establishing conformal contact with a wide range of tissue types, including tissues having complex, highly contoured surfaces. In an embodiment, at least a portion, and optionally all of, the electrodes comprise a biocompatible metal, such as titanium, gold, silver, platinum, and any combination of these. In an embodiment, at least a portion, and optionally all of, the electrodes comprise a bioresorbable metal, such as of iron, magnesium, and any combination of these. In an embodiment, the array comprises at least 10 electrodes and optionally comprises 10 to 10000 electrodes, optionally for some embodiments 10 to 1000 electrodes, and optionally for some embodiments 20 to 100 electrodes. In an embodiment, each of the electrodes has a thickness less than or equal to 10 microns, and optionally each of the electrodes has a thickness less than or equal to 1 micron, and optionally each of the electrodes has a thickness less than or equal to 500 nanometers. In an embodiment, each of the electrodes has a thickness selected over the range of 100 nanometers to 10 microns, and optionally a thickness selected over the range of 100 nanometers to 1 micron, and optionally a thickness selected over the range of 100 nanometers to 500 nanometers. In an embodiment, each of the electrodes has lateral dimensions less than or equal to 10000 microns, and optionally lateral dimensions less than or equal to 1000 microns, and optionally lateral dimensions less than or equal to 100 microns, and optionally lateral dimensions less than or equal to 10 microns. In an embodiment, electrodes in the electrode array are separated from adjacent electrodes by a distance greater than or equal to 10 microns, and optionally a distance greater than 100 microns. In an embodiment, adjacent electrodes are separated from each other by a distance selected from the range of 10 microns to 10 millimeters, and optionally the range of 10 microns to 1000 microns, and optionally the range of 10 to 100 microns.

In an embodiment, at least a portion of, and optionally all of, the electrodes and/or inorganic semiconductor components of the device are supported by a barrier layer having a mesh structure. Use of a barrier layer having a mesh structure is beneficial in the invention for providing a supporting layer allowing for efficient handling and administration of the implantable device, while at the same time providing mechanical properties (e.g., flexibility, deformability, bendability, etc.) useful for establishing conformal contact with the target tissue. In an embodiment, for example, a mesh structure refers to a layer or other structural component that occupies a portion of, but not all, the foot print area of the device, for example, occupying a portion of, but not all of, the area of the device that interfaces the target tissue. In an embodiment, for example, the foot print area of the device is an area corresponding to the perimeter of the device that establishes the interface with a target tissue, and the mesh structure of the barrier layer occupies a portion, but not all of the, foot print area. Mesh structures in some embodiments, occupy 75% or less than the foot print area and/or tissue interface area of the device, and optionally 50% or less than the foot print area and/or tissue interface area; and optionally 25% or less than the foot print area and/or tissue interface area of the device. In an embodiment, for example, the barrier layer has a mesh structure that is a lattice structure, a perforated structure or a tentacle structure. In an embodiment, for example, the barrier layer is a mesh structure having structural regions at least partially supporting, or optionally in physical contact with, the inorganic semiconductor components or electrodes, wherein structural regions of the barrier layer are separated from each other by voids where the barrier layer is not present. In such embodiments, therefore, the presence of the void regions provides a mesh structured barrier layer occupying less than the foot print area of the device. In an embodiment, for example, the barrier layer having a mesh structure is a discontinuous layer, as opposed to a continuous layer, such as a continuous film or sheet.

The composition and physical dimensions of the barrier layer are also parameters useful for providing an implantable device useful for establishing conformal contact with a target tissue. Use of a thin barrier layer (e.g., thickness less than or equal to 100 microns, optionally less than or equal to 10 microns, and optionally less than or equal to 1 micron) is useful for providing a flexible, or otherwise deformable, implantable device capable of establishing conformal contact with a wide range of tissue types, including tissues having complex, highly contoured surfaces. In an embodiment, the barrier layer comprises a polymer material, such as an elastomer, a thermoset, a thermoplastic, or a composite polymer material. In an embodiment, for example, the barrier layer is polyimide. The invention includes barrier layers comprising other materials, for example, SU-8, an insulator, a polyimide, a dielectric, and an inorganic dielectric, $Si_3N_4$. In an embodiment, the barrier layer has a thickness less than or equal to 10000 μm, and optionally a thickness less than or equal to 1000 μm, and optionally a thickness less than or equal to 100 μm, and optionally a thickness less than or equal to 10 μm. In an embodiment, the barrier layer has a thickness selected from the range of 500 nanometers to 1000 μm, and optionally a thickness selected from the range of 500 nanometers to 100 μm, and optionally a thickness selected from the range of 500 nanometers to 10 μm. In some embodiments, the barrier layer is a low modulus layer. Alternatively, the invention includes devices having a barrier layer that is a high modulus layer.

"Spatially arranged over the bioresorbable substrate" as used herein, refers to a distribution of elements (e.g. device components) over the surface area of a bioresorbable substrate such that each element is located at a different position. Inter-element spacing can be uniform or variable. In some embodiments, the elements are spatially arranged in a regular array pattern with equal inter-element spacing, for example in a 2D array. In some embodiments, the elements are spatially arranged in a line (e.g., a 1D array). Useful spatial arrangements include regular and irregular distributions of elements.

In some embodiments, the barrier layer and/or bioresorbable substrate encapsulates all of the inorganic semiconductor components and/or electrodes of the electronic device. In other embodiments, the barrier layer and/or bioresorbable substrate completely encapsulates the electronic device itself. In some embodiments, for example, the barrier layer, biocompatible layer, first dielectric layer, second dielectric layer and/or bioresorbable substrate has a thickness less than or equal to 10000 μm, optionally for some embodiments, a thickness less than or equal to 1000 μm, and optionally for some embodiments, a thickness less than or equal to 100 μm, and optionally for some embodiments, a thickness less than or equal to 10 μm. In some embodiments, for example, the barrier layer, biocompatible layer, first dielectric layer, second dielectric layer and/or bioresorbable substrate has a thickness selected from a range of 1 μm to 10000 μm, optionally for some applications selected from a range of 1 μm to 1000 μm, and optionally for some applications selected from a range of 1 μm to 100 μm. In some embodiments, the barrier layer and/or bioresorbable substrate limits net leakage current from the electronic device upon deployment in an in vivo biological environment to 10 μA/μm² or less.

Useful materials for the barrier layer and/or biocompatible layer and/or first dielectric layer and/or second dielectric layer include, for example, a polymer, an organic polymer, SU-8, an insulator, a polyimide, a dielectric, an inorganic dielectric, $Si_3N_4$, and any combination of these. In a specific embodiment, the barrier layer and/or biocompatible layer comprises an electrical insulator. In some embodiments, the barrier layer and/or biocompatible layer comprises a bioresorbable material or a bioinert material.

In an embodiment, the physical properties of the implantable biomedical device and/or electrode array (e.g., Young's modulus, net bending stiffness, toughness, etc.) provide rigidity for the device to be self-supporting, while also being capable of achieving a high degree of conformal contact with a target tissue. In an embodiment, the bioresorbable substrate, the electronic device having a plurality of inorganic semiconductor elements, and the barrier layer provide a net bending stiffness of the implantable biomedical device of less than $1 \times 10^9$ GPa μm⁴, or a net bending stiffness selected from a range of $0.1 \times 10^4$ GPa μm⁴ to $1 \times 10^8$ GPa μm⁴, optionally $1 \times 10^5$ GPa μm⁴ to $1 \times 10^8$ GPa μm⁴. In some embodiments, the bioresorbable substrate, the electronic device, and the barrier layer each independently comprise a bioresorbable material. In an embodiment, the bioresorbable substrate, the biocompatible layer, the electrode array comprising a plurality of electrodes, and the barrier layer provide a net bending stiffness of the implantable biomedical device of less than $1 \times 10^9$ GPa μm⁴, or a net bending stiffness selected from a range of $0.1 \times 10^4$ GPa μm⁴ to $1 \times 10^9$ GPa μm⁴, optionally $0.1 \times 10^4$ GPa μm⁴ to $1 \times 10^6$ GPa μm⁴.

In an embodiment, the electronic device and barrier layer have a mesh structure, which is formed by removing at least a portion of one or more supporting or encapsulating layers located proximate to an electronic device component (e.g., inorganic semiconductor element, electrode, etc.) to provide a perforated structure, having one or more holes, or a tentacle structure, where semiconductor components are physically connected at a proximal end but physically separated at a distal end.

In an embodiment, the implantable device, and/or components thereof, are at least partially optically transparent with respect to visible and/or infrared electromagnetic radiation. In an embodiment, for example, the electronic device, bioresorbable substrate, electrode array and/or barrier layer components exhibit a percentage transmission for light in the visible region of the electromagnetic spectrum equal to or greater than 70% and equal to or greater than 90% for some applications. At least partially optically transparent implantable devices are useful for visualizing and/or imaging the device during administration, use and/or removal. In addition, devices of the invention that are at least partially optically transparent are useful for coupling electromagnetic radiation into and/or out of the device. The invention includes, for example, implantable devices having an LED or laser array component for illuminating a target tissue or optical sensing, wherein the device is capable of transmitting light from the electronic device component through other components of the device, such as the bioresorbable substrate.

In another aspect, provided are methods for administering and using an implantable biomedical device. A method of this aspect comprises the steps of providing an implantable biomedical device comprising a bioresorbable substrate, an electronic device comprising a plurality of inorganic semiconductor components supported by the bioresorbable substrate, wherein at least one of the inorganic semiconductor components has at least one physical dimension less than or equal to 100 microns, and a barrier layer encapsulating at least a portion of the inorganic semiconductor components; contacting the implantable biomedical device with a target tissue of a subject in a biological environment, and at least partially resorbing the bioresorbable substrate in the biological environment, thereby establishing conformal contact between the implantable biomedical device and the target tissue in the biological environment.

Methods of this aspect are useful for administering an implantable biomedical device onto target tissue in a biological environment, where the biological environment is an in-vivo biological environment and where the target tissue may be selected from, but not limited to, heart tissue, brain tissue, muscle tissue, nerve tissue, epithelial tissue and vascular tissue.

In some embodiments, the Young's modulus of the implantable biomedical device decreases by at least 20%, or optionally by at least 50%, or optionally by at least 70%, upon complete or partial resorption of the bioresorbable substrate. The net bending stiffness of the implantable biomedical device, in some embodiments, decreases by at least 20%, or optionally by at least 50%, or optionally by at least 70%, upon complete or partial resorption of the bioresorbable substrate.

In another aspect, provided are methods of actuating a target tissue or sensing a parameter associated with the target tissue of a subject. A method of this aspect comprises the steps of providing an implantable biomedical device comprising a bioresorbable substrate, an electronic device comprising a plurality of inorganic semiconductor components supported by the bioresorbable substrate, wherein at least one of the inorganic semiconductor components has at least one physical dimension less than or equal to 100 microns, and a barrier layer encapsulating at least a portion of the inorganic semiconductor components; contacting the implantable biomedical device with the target tissue in the biological environment; at least partially resorbing the bioresorbable substrate in the biological environment, thereby establishing conformal contact between the implantable biomedical device and the target tissue in the biological environment; and actuating the target tissue or sensing the parameter associated with the target tissue that is in conformal contact with the implantable biomedical device.

In another aspect, the invention provides methods for actuating a target tissue or sensing a parameter associated with the target tissue of a subject in a biological environment, the method comprising: (1) providing an implantable biomedical device comprising: an electrode array comprising a plurality of individually addressable metal electrodes, wherein each metal electrode has at least one physical dimension less than or equal to 100 microns; a barrier layer having a mesh structure, wherein the barrier layer at least partially supports the electrode array; and a bioresorbable substrate supporting the electrode array, the barrier layer or both of the electrode array and the barrier layer; contacting the implantable biomedical device with the target tissue in a biological environment; wherein upon contact with the biological environment the bioresorbable substrate is at least partially resorbed, thereby establishing conformal contact between the electrode array and the target tissue in the biological environment; and actuating the target tissue or sensing the parameter associated with the target tissue that is in conformal contact with the implantable biomedical device.

In an embodiment, the method of this aspect further comprises measuring a voltage at a surface of the target tissue and/or generating a voltage at a surface of the target tissue. In some embodiments, the voltage generated at the surface of the target tissue is sufficient to electrophysically actuate the target tissue. In an embodiment, the method of this aspect further comprises measuring electromagnetic radiation at a surface of the target tissue and/or generating electromagnetic radiation at a surface of the target tissue. In some embodiments, the electromagnetic radiation generated at the surface of the target tissue has a power sufficient to optically actuate the target tissue. In an embodiment, the method of this aspect further comprises measuring a current at a surface of the target tissue and/or generating a current at a surface of the target tissue. In some embodiments, the current generated at the surface of the target tissue has a value sufficient to electrophysically actuate the target tissue.

In another aspect, provided are methods for making an implantable biomedical device, for example using a printing-based technique, such as transfer printing. In an embodiment, a method of the invention comprises the steps of: (1) providing a bioresorbable substrate having a receiving surface; and (2) assembling a plurality of inorganic semiconductor components or electrodes of an electrode array on the receiving surface of the bioresorbable substrate by transfer printing. In an embodiment, the step of assembling the plurality of inorganic semiconductor components or electrodes of the electrode array on the receiving surface of the bioresorbable substrate by transfer printing is carried out using dry contact transfer printing, for example, using an elastomeric stamp or a composite stamp. In an embodiment, the method further comprises providing a barrier layer encapsulating at least a portion of, and optionally all of, the inorganic semiconductor components or electrodes of the electrode array on the receiving surface of the bioresorbable substrate, for example, a barrier layer having a mesh structure. The barrier layer in these aspects may completely or partially encapsulate the inorganic semiconductor components or electrodes of the electrode array. In a method of this aspect, the inorganic semiconductor components or electrodes of the electrode array have thicknesses less than or equal to 100 microns, optionally less than or equal to 10 microns, and optionally less than or equal to 1 microns. In an embodiment, the step of encapsulating at least a portion of, and optionally all of, the inorganic semiconductor components or electrodes of the electrode array is carried out before the step of assembling the plurality of inorganic semiconductor components or electrodes of the electrode array on the receiving surface of the bioresorbable substrate by transfer printing. In an embodiment, the method further comprises providing an adhesive layer on the receiving surface of the bioresorbable substrate prior to the step of assembling the plurality of inorganic semiconductor components or electrodes of the electrode array on the receiving surface of the bioresorbable substrate by transfer printing.

In an embodiment, the invention provides a method of making an implantable electronic device, the method comprising the steps of: (1) providing a bioresorbable substrate having a receiving surface; (2) providing a handle substrate having a sacrificial layer; (3) generating a plurality of semiconductor elements or electrodes of an electrode array on the sacrificial layer of the substrate; (4) providing a barrier layer on the plurality of semiconductor elements or electrodes of the electrode array; (5) removing the sacrificial layer on the handle substrate, thereby releasing the plurality of semiconductor elements or electrodes of the electrode array; (6) assembling the plurality of inorganic semiconductor components or electrodes of an electrode array on the receiving surface of the bioresorbable substrate by transfer printing. The barrier layer in these aspects may completely or partially encapsulate the inorganic semiconductor components or electrodes of the electrode array. In an embodiment, the step of assembling the plurality of inorganic semiconductor components or electrodes of the electrode array on the receiving surface of the bioresorbable substrate by transfer printing is carried out using dry contact transfer printing, for example, using an elastomeric stamp or a composite stamp. In an embodiment, the method further comprises removing material from selected regions of the barrier layer to generate a mesh structure, for example, via wet or dry etching (e.g., reactive oxygen etching). In a method of this aspect, the inorganic semiconductor components or electrodes of the electrode array have thicknesses less than or equal to 100 microns, optionally less than or equal to 10 microns, and optionally less than or equal to 1 microns. In an embodiment, the method further comprises providing an adhesive layer on the receiving surface of the bioresorbable substrate prior to the step of assembling the plurality of inorganic semiconductor components or electrodes of an electrode array on the receiving surface of the bioresorbable substrate by transfer printing.

A range of transfer printing methods are useful in the present invention, including those using a conformable transfer device. In an embodiment, the step of assembling the plurality of inorganic semiconductor components or electrodes of the electrode array on the receiving surface of the bioresorbable substrate by transfer printing comprises the steps of: (1) contacting one or more contact surfaces of the semiconductor components or electrodes of the electrode array with a transfer surface of a conformable transfer device, thereby generating a conformable transfer device having the semiconductor components or electrodes of the electrode array disposed on a transfer surface; (2) contacting the transfer surface of the conformable transfer device having the semiconductor components or electrodes of the electrode array with the receiving surface of the bioresorbable substrate in a manner to establish conformal contact between the transfer surface of the conformal transfer device and the receiving surface of the bioresorbable substrate; and (3) separating the conformable transfer device and the semiconductor components or electrodes of the electrode array, thereby transferring the semiconductor components or electrodes of the electrode array to the receiving surface of the bioresorbable substrate. In an embodiment, the semiconductor components or electrodes of the electrode array are at least partially encapsulated by barrier layer and the transfer surface of the conformable transfer device contacts the barrier layer provided on the contact surfaces of the semiconductor components or electrodes of the electrode array. In an embodiment, the conformal transfer device is a stamp, such as an elastomer stamp or a composite elastomer stamp.

The invention provides a method of making an implantable device, the method comprising the steps of (1) providing a substrate having a sacrificial layer; applying a first dielectric layer on the sacrificial layer of the substrate; (2) providing at least one inorganic semiconductor component on the first dielectric layer; (3) covering a portion of the at least one inorganic semiconductor component with a second dielectric layer, thereby generating a covered inorganic semiconductor component having an exposed distal end; (4) providing an electrode that physically contacts the exposed distal end of the inorganic semiconductor component; (5) removing at least a portion of the first dielectric layer, the second dielectric layer or both, thereby generating a mesh structure; (6) removing the sacrificial layer on the substrate to leave a mesh structure; and (7) transferring the mesh structure to a receiving surface of a bioresorbable substrate. In an embodiment, the step of removing at least a portion of the first dielectric layer and the second dielectric layer to generate the mesh structure comprises etching, for example, oxygen reactive ion etching. In an embodiment, the step of providing at least one inorganic semiconductor component on the first dielectric layer is carried out via transfer printing, for example, via dry contact transfer printing. In an embodiment, the step of transferring the mesh structure to a receiving surface of a bioresorbable substrate is carried out via transfer printing, for example, via dry contact transfer printing. In embodiments, implantable biomedical devices described above are made according to methods of this aspect. In an embodiment, the inorganic semiconductor component has on dimension less than or equal to 100 microns, optionally for some embodiment less than or equal to 10 microns and optionally for some embodiment less than or equal to 1 micron.

In another aspect, provided are methods for making an implantable biomedical device. A method of this aspect comprises the steps of: (1) providing a sacrificial layer on a substrate; (2) applying a first polymer layer on the sacrificial layer on the substrate; (3) providing an electrode array on the first polymer layer, wherein the electrode array comprises a plurality of electrodes; (4) removing at least a portion of the first polymer layer, thereby generating a mesh structure; (5) removing the sacrificial layer on the substrate; and (6) transferring the mesh structure and electrode array to a receiving surface of a bioresorbable substrate. In an embodiment, the step of removing at least a portion of the first polymer comprises dissolving or etching, for example, oxygen reactive ion etching. In an embodiment, the step of providing an electrode array on the first polymer layer, is carried out via transfer printing, for example, via dry contact transfer printing. In an embodiment, the step of transferring the mesh structure and electrode array to a receiving surface of a bioresorbable substrate, is carried out via transfer printing, for example, via dry contact transfer printing.

In embodiments, implantable biomedical devices described above are made according to methods of this aspect.

Useful materials for the sacrificial layer on the substrate include, but are not limited to, a polymer, polymethylmethacrylate (PMMA), polyimide, polyethylene terepthalate (PET), polystyrene, polycarbonate, polyvinyl alcohol (PVA), polybenzimidazole, tetrafluoroethylene, SU-8, parylene, polyester, poly-dimethyl-siloxane (PDMS), and any combination of these.

The implantable biomedical devices described above may be used in the disclosed methods.

In some embodiments, the geometry of electronic devices may be used to provide stretchability, flexibility, conformability and/or compressibility. In an embodiment, the devices may exploit inorganic semiconductor materials configured into structural shapes that can geometrically accommodate large mechanical deformations without imparting significant strain in the materials themselves. For example, bridges connecting rigid device islands may be wavy, buckled, serpentine or meandering as further described in U.S. patent application Ser. No. 11/851,182 (U.S. Pub. No. 2008/0157235); U.S. patent application Ser. No. 12/405,475 (U.S. Pub. No. 2010/

059863); and U.S. patent application Ser. No. 12/398,811 (U.S. Pub. No. 2010/0002402), each of which is hereby incorporated by reference.

In an aspect, devices disclosed herein comprise one or more stretchable components, such as disclosed in U.S. patent application Ser. No. 11/851,182 and/or U.S. patent application Ser. No. 12/405,475 and/or U.S. patent application Ser. No. 12/398,811, and are made by one or more of the processes disclosed therein. U.S. patent application Ser. No. 11/851,182; U.S. patent application Ser. No. 12/405,475; and U.S. patent application Ser. No. 12/398,811 are hereby incorporated by reference.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIGS. 1a, 1b and 1c provide top plan and cross-sectional views of an implantable biomedical device, according to an exemplary embodiment.

FIG. 4 provides a side plan view of an implantable biomedical device having a biocompatible layer, according to an exemplary embodiment.

FIGS. 5a and 5b provide a process flow schematic for making implantable biomedical devices having mesh structures, according to multiple embodiments.

FIGS. 8a and 8b provide side plan views of implantable biomedical devices showing planar contact surfaces and nanostructured or microstructured contact surfaces, respectively.

FIGS. 9a, 9b, 9c and 9d provide schematic diagrams and images of implantable biomedical devices having single crystalline silicon electronics. Schematic diagram (left) corresponding high resolution image (right) and microscope image (inset) of (a) ultrathin devices on a carrier wafer, (b) devices lifted onto the surface of a PDMS stamp, and (c) process for transfer printing onto a silk film cast on a silicon wafer. (d) Schematic diagram of transfer printing onto a freestanding silk film (left) and dissolution (right).

FIGS. 10a and 10b provide images and data showing bending and electronic properties of the implantable biomedical devices of FIG. 9. (a) Ultrathin devices on a flexible silk substrate, in flat (left) and bent (center and right) configurations. (b) Transfer curves (left) and IV curves (right) before (solid curve) and after (dotted curve) dissolution, where $I_d$, $V_g$, and $V_d$ represent the drain current, gate voltage, and drain voltage, respectively. The voltage for each IV curve in the right frame denotes the gate bias voltage.

FIGS. 11a, 11b and 11c show images of in-vitro bioresorbable substrate dissolution. Images of the water dissolution of a system of silicon electronics on silk, at various time stages (left) with magnified views (right): (a) start and (b) after 3 min. (c) Image of devices recovered on filter paper after complete dissolution of the silk (left) with magnified view (right).

FIGS. 13a, 13b and 13c provide schematic illustrations and images corresponding to steps for fabricating silk-supported implantable biomedical devices. Schematic illustration and images corresponding to steps for fabricating conformal silk-supported PI electrode arrays. a, Casting and drying of silk fibroin solution on a temporary substrate of PDMS; 5-15 μm thick silk film after drying for 12 hours at room temperature. b, Steps for fabricating the electrode arrays, transfer printing them onto silk, and connecting to ACF cable. c, Schematic illustration of clinical usage of a representative device in an ultrathin mesh geometry with dissolvable silk support.

FIGS. 15a and 15b provide images of implantable biomedical devices on silk and polyimide, respectively, after connection of anisotropic conductive film cables and circuit boards. Images of electrode array after connection of ACF and circuit board. a, electrode array with thin (<10 μm) substrate thickness. b, electrode array with thick (>10 μm) substrate thickness.

FIGS. 20a and 20b provide images of mesh implantable biomedical devices on a glass cylinder and a human brain model, respectively, after dissolution of a silk substrate.

FIGS. 21a, 21b, 21c, 21d and 21e provide images and graphs of mechanically modeled, theoretically predicted, and measured properties of implantable biomedical devices. Mechanical modeling, theoretical predictions and measured properties. a, A thin film wrapped around a cylinder of radius R. The unwrapped and wrapped states appear in the top and center frames, respectively. The bottom frame compares the mechanics model and experiments. b, A thin film wrapped around two overlapped cylinders. The top and center frames show the unwrapped and wrapped states, respectively. The bottom frame shows a comparison between the mechanics model and experiments. c, Images of electrode arrays (76 µm sheet in left top, 2.5 µm sheet in right top and 2.5 µm mesh in bottom panel) wrapped onto a glass hemisphere. d, Mechanics models for sheet (left frame) and mesh (right frame) designs. e, The critical adhesion energy (left frame) and the normal (peeling) stress between the film and sphere surface (right frame) for sheet and mesh designs.

FIGS. 22a, 22b, 22c and 22d provide images of wrapping experiments on glass cylinders of different diameters (diameter is a, 3.5 cm, b, 1.3 cm, c, 0.4 cm and d, 0.1 cm.)

FIGS. 23a and 23b provide images of wrapping experiments on overlapped cylinders (a, angled view. b, side view).

FIGS. 26a and 26b provide schematic diagrams of implantable biomedical devices. Schematic diagram for analytical model and its modeling result. a, Cross section of the neural sensor, with geometrical parameters illustrated. b, Cross section of the neural sensor on a silk backing substrate.

DETAILED DESCRIPTION OF THE INVENTION

Figure 2:
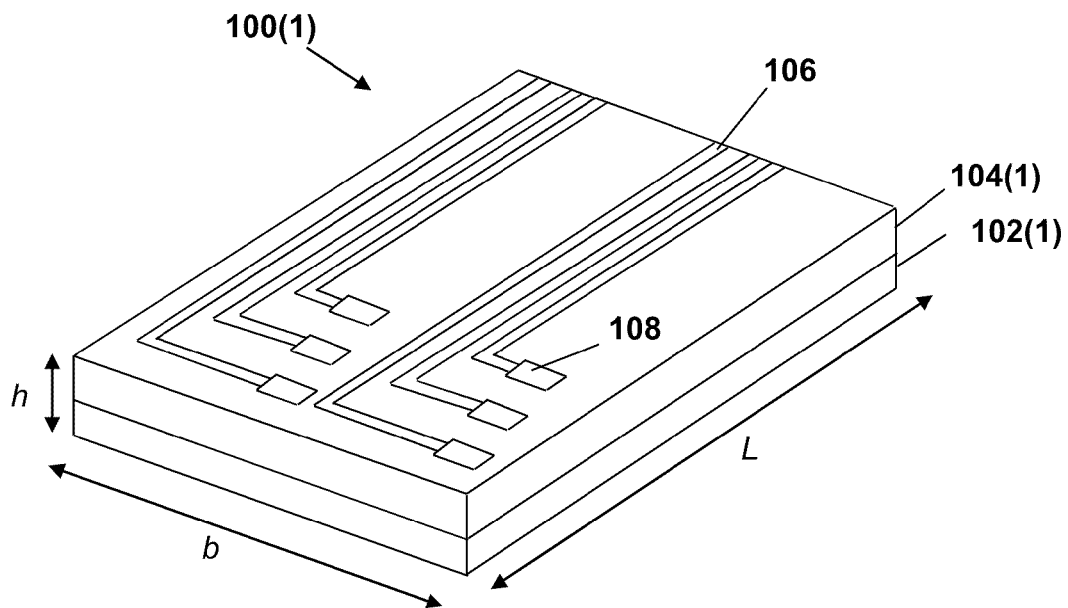
FIG. 2 provides a top perspective view of the implantable biomedical device of FIG. 1.

In general, the terms and phrases used herein have their art-recognized meaning, which can be found by reference to standard texts, journal references and contexts known to those skilled in the art. The following definitions are provided to clarify their specific use in the context of the invention.

"Functional layer" refers to a layer that imparts some functionality to the device. For example, the functional layer may contain semiconductor components. Alternatively, the functional layer may comprise multiple layers, such as multiple semiconductor layers separated by support layers. The functional layer may comprise a plurality of patterned elements, such as interconnects running between electrodes or islands. The functional layer may be heterogeneous or may have one or more properties that are inhomogeneous. "Inhomogeneous property" refers to a physical parameter that can spatially vary, thereby effecting the position of the neutral mechanical plane within a multilayer device.

"Structural layer" refers to a layer that imparts structural functionality, for example by supporting and/or encapsulating device components.

"Semiconductor" refers to any material that is an insulator at a very low temperature, but which has an appreciable electrical conductivity at a temperature of about 300 Kelvin. In the present description, use of the term semiconductor is intended to be consistent with use of this term in the art of microelectronics and electronic devices. Useful semiconductors include those comprising elemental semiconductors, such as silicon, germanium and diamond, and compound semiconductors, such as group IV compound semiconductors such as SiC and SiGe, group III-V semiconductors such as AlSb, AlAs, AlN, AlP, BN, BP, BAs, GaSb, GaAs, GaN, GaP, InSb, InAs, InN, and InP, group III-V ternary semiconductors alloys such as $Al_xGa_{1-x}As$, group II-VI semiconductors such as CsSe, CdS, CdTe, ZnO, ZnSe, ZnS, and ZnTe, group I-VII semiconductors such as CuCl, group IV-VI semiconductors such as PbS, PbTe, and SnS, layer semiconductors such as $PbI_2$, $MoS_2$, and GaSe, oxide semiconductors such as CuO and $Cu_2O$. The term semiconductor includes intrinsic semiconductors and extrinsic semiconductors that are doped with one or more selected materials, including semiconductors having p-type doping materials and n-type doping materials, to provide beneficial electronic properties useful for a given application or device. The term semiconductor includes composite materials comprising a mixture of semiconductors and/or dopants. Specific semiconductor materials useful for some embodiments include, but are not limited to, Si, Ge, Se, diamond, fullerenes, SiC, SiGe, SiO, $SiO_2$, SiN, AlSb, AlAs, AlIn, AlN, AlP, AlS, BN, BP, BAs, $As_2S_3$, GaSb, GaAs, GaN, GaP, GaSe, InSb, InAs, InN, InP, CsSe, CdS, CdSe, CdTe, $Cd_3P_2$, $Cd_3As_2$, $Cd_3Sb_2$, ZnO, ZnSe, ZnS, ZnTe, $Zn_3P_2$, $Zn_3As_2$, $Zn_3Sb_2$, $ZnSiP_2$, CuCl, PbS, PbSe, PbTe, FeO, $FeS_2$, NiO, EuO, EuS, PtSi, TlBr, $CrBr_3$, SnS, SnTe, $PbI_2$, $MoS_2$, GaSe, CuO, $Cu_2O$, HgS, HgSe, HgTe, $HgI_2$, MgS, MgSe, MgTe, CaS, CaSe, SrS, SrTe, BaS, BaSe, BaTe, $SnO_2$, TiO, $TiO_2$, $Bi_2S_3$, $Bi_2O_3$, $Bi_2Te_3$, $BiI_3$, $UO_2$, $UO_3$, $AgGaS_2$, PbMnTe, $BaTiO_3$, $SrTiO_3$, $LiNbO_3$, $La_2CuO_4$, $La_{0.7}Ca_{0.3}MnO_3$, CdZnTe, CdMnTe, $CuInSe_2$, copper indium gallium selenide (CIGS), HgCdTe, HgZnTe, HgZnSe, PbSnTe, $Tl_2SnTe_5$, $Tl_2GeTe_5$, AlGaAs, AlGaN, AlGaP, AlInAs, AlInSb, AlInP, AlInAsP, AlGaAsN, GaAsP, GaAsN, GaMnAs, GaAsSbN, GaInAs, GaInP, AlGaAsSb, AlGaAsP, AlGaInP, GaInAsP, InGaAs, InGaP, InGaN, InAsSb, InGaSb, InMnAs, InGaAsP, InGaAsN, InAlAsN, GaInNAsSb, GaInAsSbP, and any combination of these. Porous silicon semiconductor materials are useful for aspects described herein. Impurities of semiconductor materials are atoms, elements, ions and/or molecules other than the semiconductor material(s) themselves or any dopants provided to the semiconductor material. Impurities are undesirable materials present in semiconductor materials which may negatively impact the electronic properties of semiconductor materials, and include but are not limited to oxygen, carbon, and metals including heavy metals. Heavy metal impurities include, but are not limited to, the group of elements between copper and lead on the periodic table, calcium, sodium, and all ions, compounds and/or complexes thereof.

A "semiconductor component" broadly refers to any semiconductor material, composition or structure, and expressly includes high quality single crystalline and polycrystalline semiconductors, semiconductor materials fabricated via high temperature processing, doped semiconductor materials, inorganic semiconductors, and composite semiconductor materials.

A "component" is used broadly to refer to an individual part of a device. An "interconnect" is one example of a component, and refers to an electrically conducting structure capable of establishing an electrical connection with another component or between components. In particular, an interconnect may establish electrical contact between components that are separate. Depending on the desired device specifications, operation, and application, an interconnect is made from a suitable material. Suitable conductive materials include semiconductors.

Other components include, but are not limited to, thin film transistors (TFTs), transistors, electrodes, integrated circuits, circuit elements, control elements, microprocessors, transducers, islands, bridges and combinations thereof. Components may be connected to one or more contact pads as known in the art, such as by metal evaporation, wire bonding, and application of solids or conductive pastes, for example.

"Neutral mechanical plane" (NMP) refers to an imaginary plane existing in the lateral, b, and longitudinal, l, directions of a device. The NMP is less susceptible to bending stress than other planes of the device that lie at more extreme positions along the vertical, h, axis of the device and/or within more bendable layers of the device. Thus, the position of the NMP is determined by both the thickness of the device and the materials forming the layer(s) of the device.

"Coincident" refers to the relative position of two or more objects, planes or surfaces, for example a surface such as a neutral mechanical plane that is positioned within or is adjacent to a layer, such as a functional layer, substrate layer, or other layer. In an embodiment, a neutral mechanical plane is positioned to correspond to the most strain-sensitive layer or material within the layer.

"Proximate" refers to the relative position of two or more objects, planes or surfaces, for example a neutral mechanical plane that closely follows the position of a layer, such as a functional layer, substrate layer, or other layer while still providing desired conformability without an adverse impact on the strain-sensitive material physical properties. "Strain-sensitive" refers to a material that fractures or is otherwise impaired in response to a relatively low level of strain. In general, a layer having a high strain sensitivity, and consequently being prone to being the first layer to fracture, is located in the functional layer, such as a functional layer containing a relatively brittle semiconductor or other strain-sensitive device element. A neutral mechanical plane that is proximate to a layer need not be constrained within that layer, but may be positioned proximate or sufficiently near to provide a functional benefit of reducing the strain on the strain-sensitive device element when the device is conformed to a tissue surface.

"Electronic device" generally refers to a device incorporating a plurality of components, and includes large area electronics, printed wire boards, integrated circuits, component arrays, biological and/or chemical sensors, and physical sensors (e.g., temperature, etc.).

"Sensing" refers to detecting the presence, absence, amount, magnitude or intensity of a physical and/or chemical property. Useful electronic device components for sensing include, but are not limited to electrode elements, chemical or biological sensor elements, pH sensors, temperature sensors and capacitive sensors.

"Actuating" refers to stimulating, controlling, or otherwise affecting an external structure, material or fluid, for example a biological tissue. Useful electronic device components for actuating include, but are not limited to, electrode elements, electromagnetic radiation emitting elements, light emitting diodes, lasers, and heating elements.

"Island" refers to a relatively rigid component of an electronic device comprising a plurality of semiconductor components. "Bridge" refers to structures interconnecting two or more islands or one island to another component. Specific bridge structures include semiconductor interconnects.

"Encapsulate" refers to the orientation of one structure such that it is at least partially, and in some cases completely, surrounded by one or more other structures. "Partially encapsulated" refers to the orientation of one structure such that it is partially surrounded by one or more other structures. "Completely encapsulated" refers to the orientation of one structure such that it is completely surrounded by one or more other structures. The invention includes implantable devices having partially or completely encapsulated inorganic semiconductor components and/or electrodes.

"Barrier layer" refers to a component spatially separating two or more other components or spatially separating a component from a structure, material or fluid external to the device. In one embodiment, a barrier layer encapsulates one or more components. In some embodiments, a barrier layer separates one or more components from an aqueous solution, a biological tissue or both.

A barrier layer(s), and optionally a sacrificial layer on a substrate, may be etched to produce a "mesh structure", where at least a portion of the barrier layer(s), and optionally the sacrificial layer on a substrate, is removed. For example a portion of the barrier layer(s) disposed approximately 10 nanometers or more from an inorganic semiconductor component or additional component is removed. Removal of at least a portion of the barrier layer(s), and optionally the sacrificial layer on the substrate, may produce (i) one or more holes within the barrier layer(s) and/or (ii) electrical components, which are physically joined by a barrier layer(s) at a proximal end and physically separated at a distal end. In one embodiment, a mesh structure may be disposed upon a contiguous bioresorbable substrate, which provides structural support for the device during deployment into a biological environment.

"Contiguous" refers to materials or layers that are touching or connected throughout in an unbroken sequence. In one embodiment, a contiguous layer of an implantable biomedical device has not been etched to remove a substantial portion (e.g., 10% or more) of the originally provided material or layer.

"Active circuit" and "active circuitry" refer to one or more components configured for performing a specific function. Useful active circuits include, but are not limited to, amplifier circuits, multiplexing circuits, current limiting circuits, integrated circuits, transistors and transistor arrays.

"Substrate" refers to a material, layer or other structure having a surface, such as a receiving surface, that is capable of supporting one or more components or electronic devices. A component that is "bonded" to the substrate refers to a component that is in physical contact with the substrate and unable to substantially move relative to the substrate surface to which it is bonded. Unbonded components or portions of a component, in contrast, are capable of substantial movement relative to the substrate.

"Bioresorbable" refers to a material that is susceptible to being chemically broken down into lower molecular weight chemical moieties by reagents that are naturally present in a biological environment. In an in-vivo application, the chemical moieties may be assimilated into human or animal tissue.

A bioresorbable material that is "substantially completely" resorbed is highly resorbed (e.g., 95% resorbed, or 98% resorbed, or 99% resorbed, or 99.9% resorbed, or 99.99% resorbed), but not completely (i.e., 100%) resorbed.

"Biocompatible" refers to a material that does not elicit an immunological rejection or detrimental effect when it is disposed within an in-vivo biological environment. For example, a biological marker indicative of an immune response changes less than 10%, or less than 20%, or less than 25%, or less than 40%, or less than 50% from a baseline value when a biocompatible material is implanted into a human or animal.

"Bioinert" refers to a material that does not elicit an immune response from a human or animal when it is disposed within an in-vivo biological environment. For example, a biological marker indicative of an immune response remains substantially constant (plus or minus 5% of a baseline value) when a bioinert material is implanted into a human or animal.

"Nanostructured contact surface" and "microstructured contact surface" refer to device surfaces having nanometer-sized and micrometer-sized relief features, respectively, for contacting and penetrating a target tissue and improving adhesion between the implantable biomedical device and the target tissue. The relief features extend a length, x, from a substantially contiguous plane of the device surface. Quantitative descriptors of a structured contact surface include surface roughness parameters, such as $R_{max}$, $R_a$, and normalized roughness ($R_a/R_{max}$), all of which may be measured by atomic force microscopy (AFM). $R_{max}$ is the maximum height between a highest peak to a lowest valley. $R_a$ is the center-line-mean roughness, which is the average of an absolute value of a deviation from a center line of a roughness curve to the roughness curve. The surface of a substrate or barrier layer is "substantially smooth", for the purposes of this disclosure, if the surface has an $R_a$ value of 100 nm or less. If the surface has an $R_a$ value greater than 100 nm, the surface is considered to be a "structured surface" for purposes of this disclosure. A structured surface may contain at least one feature selected from the group consisting of barbs, spikes, protrusions and any combination of these.

"Dielectric" refers to a non-conducting or insulating material. In an embodiment, an inorganic dielectric comprises a dielectric material substantially free of carbon. Specific examples of inorganic dielectric materials include, but are not limited to, silicon nitride, silicon dioxide and polymers.

"Polymer" refers to a macromolecule composed of repeating structural units connected by covalent chemical bonds or the polymerization product of one or more monomers, often characterized by a high molecular weight. The term polymer includes homopolymers, or polymers consisting essentially of a single repeating monomer subunit. The term polymer also includes copolymers, or polymers consisting essentially of two or more monomer subunits, such as random, block, alternating, segmented, grafted, tapered and other copolymers. Useful polymers include organic polymers or inorganic polymers that may be in amorphous, semi-amorphous, crystalline or partially crystalline states. Crosslinked polymers having linked monomer chains are particularly useful for some applications. Polymers useable in the methods, devices and components include, but are not limited to, plastics, elastomers, thermoplastic elastomers, elastoplastics, thermoplastics and acrylates. Exemplary polymers include, but are not limited to, acetal polymers, biodegradable polymers, cellulosic polymers, fluoropolymers, nylons, polyacrylonitrile polymers, polyamide-imide polymers, polyimides, polyarylates, polybenzimidazole, polybutylene, polycarbonate, polyesters, polyetherimide, polyethylene, polyethylene copolymers and modified polyethylenes, polyketones, poly(methyl methacrylate), polymethylpentene, polyphenylene oxides and polyphenylene sulfides, polyphthalamide, polypropylene, polyurethanes, styrenic resins, sulfone-based resins, vinyl-based resins, rubber (including natural rubber, styrene-butadiene, polybutadiene, neoprene, ethylene-propylene, butyl, nitrile, silicones), acrylic, nylon, polycarbonate, polyester, polyethylene, polypropylene, polystyrene, polyvinyl chloride, polyolefin or any combinations of these.

"Elastomeric stamp" and "elastomeric transfer device" are used interchangeably and refer to an elastomeric material having a surface that can receive as well as transfer a material. Exemplary elastomeric transfer devices include stamps, molds and masks. The transfer device affects and/or facilitates material transfer from a donor material to a receiver material.

"Elastomer" refers to a polymeric material which can be stretched or deformed and returned to its original shape without substantial permanent deformation. Elastomers commonly undergo substantially elastic deformations. Useful elastomers include those comprising polymers, copolymers, composite materials or mixtures of polymers and copolymers. Elastomeric layer refers to a layer comprising at least one elastomer. Elastomeric layers may also include dopants and other non-elastomeric materials. Useful elastomers include, but are not limited to, thermoplastic elastomers, styrenic materials, olefinic materials, polyolefin, polyurethane thermoplastic elastomers, polyamides, synthetic rubbers, PDMS, polybutadiene, polyisobutylene, poly(styrene-butadiene-styrene), polyurethanes, polychloroprene and silicones. In some embodiments, an elastomeric stamp comprises an elastomer. Exemplary elastomers include, but are not limited to silicon containing polymers such as polysiloxanes including poly(dimethyl siloxane) (i.e. PDMS and h-PDMS), poly(methyl siloxane), partially alkylated poly(methyl siloxane), poly(alkyl methyl siloxane) and poly(phenyl methyl siloxane), silicon modified elastomers, thermoplastic elastomers, styrenic materials, olefinic materials, polyolefin, polyurethane thermoplastic elastomers, polyamides, synthetic rubbers, polyisobutylene, poly(styrene-butadiene-styrene), polyurethanes, polychloroprene and silicones. In an embodiment, a polymer is an elastomer.

"Conformable" refers to a device, material or substrate which has a bending stiffness that is sufficiently low to allow the device, material or substrate to adopt any desired contour profile, for example a contour profile allowing for conformal contact with a surface having a pattern of relief features. In certain embodiments, a desired contour profile is that of a tissue in a biological environment.

"Conformal contact" refers to contact established between a device and a receiving surface, which may for example be a target tissue in a biological environment. In one aspect, conformal contact involves a macroscopic adaptation of one or more surfaces (e.g., contact surfaces) of an implantable device to the overall shape of a tissue surface. In another aspect, conformal contact involves a microscopic adaptation of one or more surfaces (e.g., contact surfaces) of an implantable device to a tissue surface resulting in an intimate contact substantially free of voids. In an embodiment, conformal contact involves adaptation of a contact surface(s) of the implantable device to a receiving surface(s) of a tissue such that intimate contact is achieved, for example, wherein less than 20% of the surface area of a contact surface of the implantable device does not physically contact the receiving surface, or optionally less than 10% of a contact surface of the implantable device does not physically contact the receiving surface, or optionally less than 5% of a contact surface of the implantable device does not physically contact the receiving surface.

"Young's modulus" is a mechanical property of a material, device or layer which refers to the ratio of stress to strain for a given substance. Young's modulus may be provided by the expression:

$$E = \frac{\text{(stress)}}{\text{(strain)}} = \left(\frac{L_0}{\Delta L}\right)\left(\frac{F}{A}\right), \quad \text{(I)}$$

where E is Young's modulus, $L_0$ is the equilibrium length, $\Delta L$ is the length change under the applied stress, F is the force applied, and A is the area over which the force is applied. Young's modulus may also be expressed in terms of Lame constants via the equation:

$$E = \frac{\mu(3\lambda + 2\mu)}{\lambda + \mu}, \quad \text{(II)}$$

where $\lambda$ and $\mu$ are Lame constants. High Young's modulus (or "high modulus") and low Young's modulus (or "low modulus") are relative descriptors of the magnitude of Young's modulus in a given material, layer or device. In some embodiments, a high Young's modulus is larger than a low Young's modulus, preferably about 10 times larger for some applications, more preferably about 100 times larger for other applications, and even more preferably about 1000 times larger for yet other applications. In an embodiment, a low modulus layer has a Young's modulus less than 100 MPa, optionally less than 10 MPa, and optionally a Young's modulus selected from the range of 0.1 MPa to 50 MPa. In an embodiment, a high modulus layer has a Young's modulus greater than 100 MPa, optionally greater than 10 GPa, and optionally a Young's modulus selected from the range of 1 GPa to 100 GPa.

"Inhomogeneous Young's modulus" refers to a material having a Young's modulus that spatially varies (e.g., changes with surface location). A material having an inhomogeneous Young's modulus may optionally be described in terms of a "bulk" or "average" Young's modulus for the entire material.

"Low modulus" refers to materials having a Young's modulus less than or equal to 10 MPa, less than or equal to 5 MPa or less than or equal to 1 MPa.

"Bending stiffness" is a mechanical property of a material, device or layer describing the resistance of the material, device or layer to an applied bending moment. Generally, bending stiffness is defined as the product of the modulus and area moment of inertia of the material, device or layer. A material having an inhomogeneous bending stiffness may optionally be described in terms of a "bulk" or "average" bending stiffness for the entire layer of material.

Described herein are implantable biomedical devices for sensing a parameter associated with a target tissue and/or actuating a target tissue in a biological environment, as well as methods for making and using the implantable biomedical devices. These devices are capable of intimate integration on the soft, curvilinear surfaces of biological tissues and are useful for monitoring and/or treating medical conditions in real time and with high spatial precision. The disclosed devices and methods also include those specially suited for monitoring and/or actuating tissues in-vivo. The approaches rely on dissolvable, biocompatible, and bioresorbable substrates, where dissolution and capillary forces drive a wrapping process. Purely passive electrode systems serve to demonstrate the advantages and underlying aspects of these systems, but the same approaches are compatible with fully active electronics and optoelectronics.

Implantable biomedical devices and methods of making and using the devices will now be described with reference to the figures. For clarity, multiple items within a figure may not be labeled and the figures may not be drawn to scale. Like numerals in multiple figures represent like items, and items numbered with parentheses, e.g., implantable biomedical devices 100(1)-100(7), represent species within a genus, which may be broadly referred to without parentheses, e.g., implantable biomedical device 100.

FIG. 1a shows a top plan view of an implantable biomedical device 100(1) having a plurality of electronic interconnects 106 and electrodes 108, which form part of an electronic device, disposed upon or encapsulated within a barrier layer 104(1) that is supported by a bioresorbable substrate 102(1). Connection of an anisotropic conductive film (ACF) cable 110 to implantable biomedical device 100(1) allows for communication with a circuit board 112, which may be used in conjunction with known software, memory devices, user interfaces, and power sources (not shown) to analyze data obtained from device 100(1) and/or to deliver electromagnetic radiation to device 100(1). FIG. 1b shows a cross-sectional view of implantable biomedical device 100(1) taken through a plane defined by line B-B. Interconnects 106 are shown as encapsulated within barrier layer 104(1) and coincident to a neutral mechanical plane (NMP) of the device. FIG. 1c shows a cross-sectional view of implantable biomedical device 100(1) taken through a plane defined by line C-C. Interconnects 106 remain disposed within barrier layer 104(1), but electrodes 108 are shown as exposed to ambient conditions. In other embodiments (not shown), the entire electronic device including electrodes 108 may be encapsulated within a barrier layer.

FIG. 2 provides a top perspective view of implantable biomedical device 100(1) having physical dimensions including a vertical dimension or height, h, a lateral dimension or width, b, and a longitudinal dimension or length, L. Implantable biomedical device 100(1) may have any regular or irregular shape, but will often be in the form of a square or rectangular parallelogram.

Figure 3:
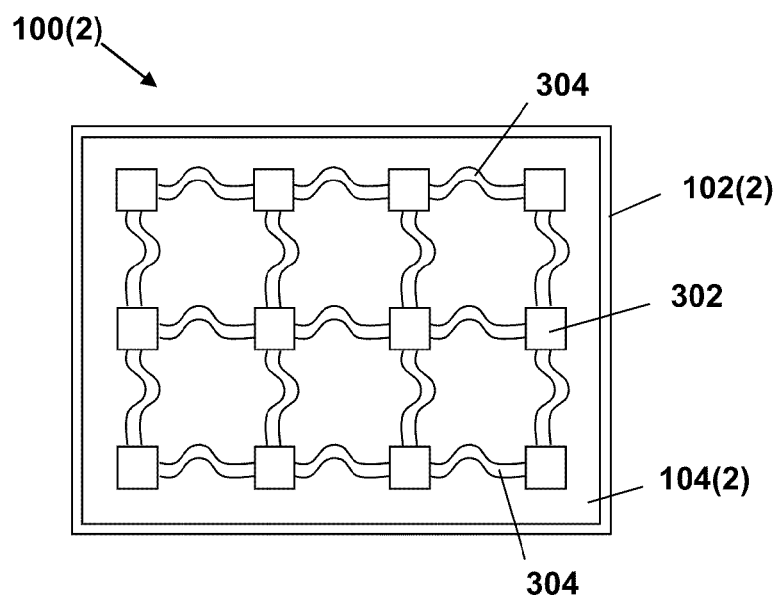
FIG. 3 provides a top plan view of an implantable biomedical device having islands and bridges, according to an exemplary embodiment.

FIG. 3 shows a top plan view of an implantable biomedical device 100(2) having islands 302 and bridges 304, which form part of an electronic device. Islands 302 and bridges 304 are at least partially encapsulated by a barrier layer 104(2) and supported by a bioresorbable substrate 102(2). Islands 302 may, for example, be rigid semiconductor components linked by bridges 304, which may have a wavy, serpentine or meandering configuration that allows for a high degree of flexibility, bendability, conformability or compressibility. Bridges 304 may be disposed completely within the plane of the islands or at least a portion of bridges 304 may extend vertically above the plane of the islands, such that a void space exists beneath at least part of each bridge 304.

FIG. 4 shows a side plan view of an implantable biomedical device 100(3) having a biocompatible layer 402 in addition to a bioresorbable substrate 102(3), a barrier layer 104(3) and electronic device components 404, such as interconnects, electrodes, islands, bridges, etc.

FIGS. 5a and 5b provide schematic illustrations of implantable biomedical devices 100(4) and 100(5) having mesh structures. FIG. 5a shows an electronic device having a tentacle mesh structure, where semiconductor components 502 are at least partially encapsulated by a barrier layer and/or biocompatible layer 508. Layer 508 physically joins proximal ends 504 of semiconductor components 502, but distal ends 506 of semiconductor components 502 are physically separated. In some embodiments, each semiconductor component 502 is separated from every other semiconductor component at its distal end 506. In other embodiments, groups of two or more semiconductor components 502 may be physically separated from other groups of neighboring semiconductor components 502. A bioresorbable substrate 102(4) provides support for the mesh electronic device.

FIG. 5b shows an electronic device having a perforated mesh structure, where semiconductor components in the form of islands 302 and bridges 304 are at least partially encapsulated by a barrier layer and/or biocompatible layer 510. Layer 510 contains holes 512 where the material of layer 510 has been removed, e.g., by reactive ion etching. A bioresorbable substrate 102(5) provides support for the mesh electronic device. Perforated mesh structures are not limited to electronic devices comprising islands and bridges. Barrier and/or biocompatible layer material may be removed to form holes in any of the electronic devices described herein. For example, etching of implantable biomedical device 100(4) (FIG. 5a) that removes material between semiconductor components 502 but leaves both proximal 504 and distal 506 ends joined will create a perforated mesh structure.

Figure 6:
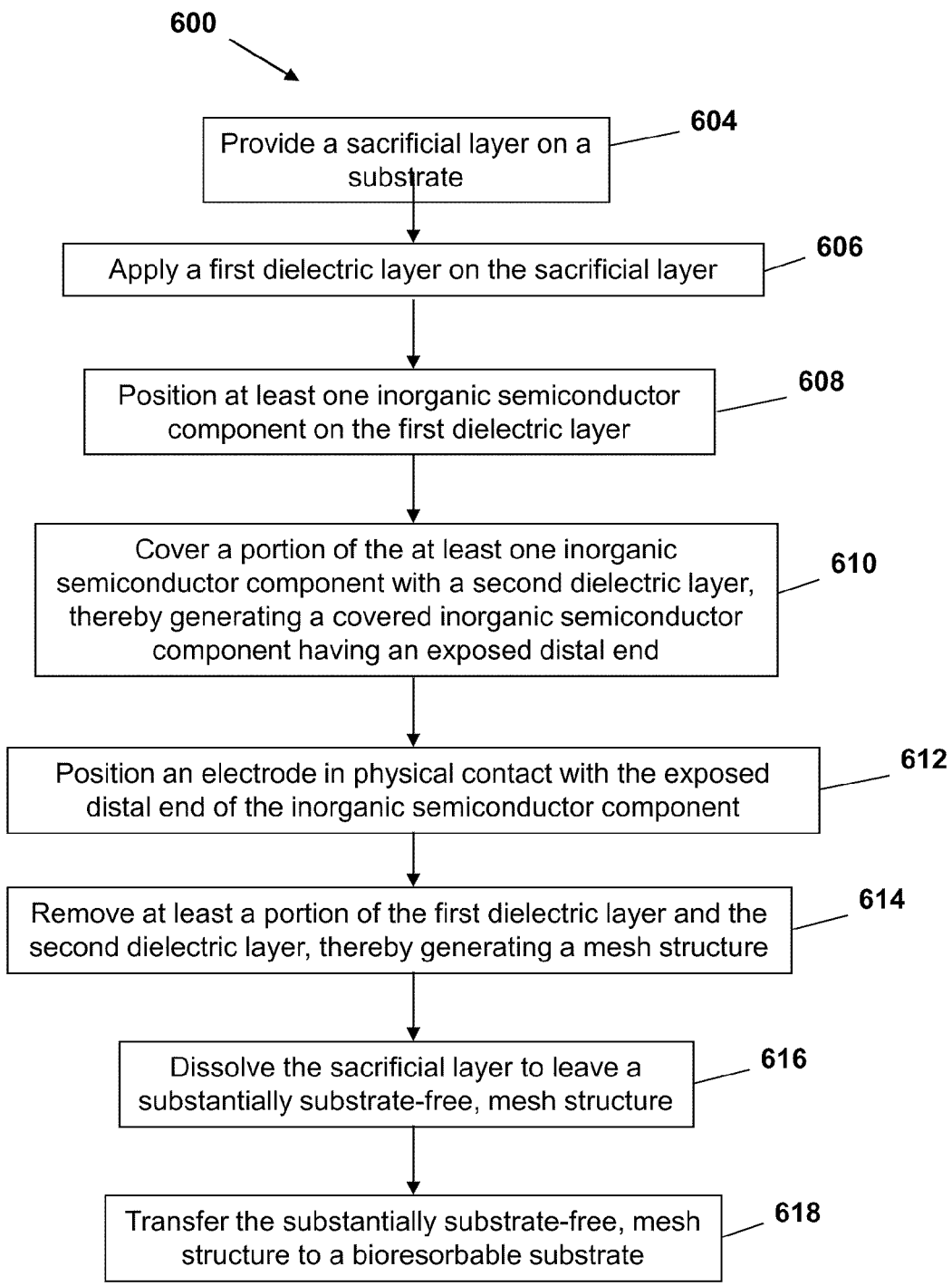
FIG. 6 provides a flowchart illustrating exemplary steps for making implantable biomedical devices having mesh structures.

FIG. 6 provides a flowchart 600 illustrating exemplary steps for making implantable biomedical devices 100 having a mesh structure, e.g., 100(4) and 100(5). In step 604, a sacrificial layer is provided on a substrate. A first dielectric layer is applied to the sacrificial layer on a substrate in step 606, and at least one inorganic semiconductor component is positioned or otherwise assembled on the first dielectric layer in step 608. A portion of the at least one inorganic semiconductor component is covered with a second dielectric layer, in step 610, to generate a covered inorganic semiconductor component having an exposed distal end. In step 612, an electrode is positioned to physically contact the exposed distal end of the inorganic semiconductor component. A portion of the first and second dielectric layers is then removed to generate a mesh structure in step 614. The sacrificial layer on the substrate is removed (e.g., dissolved or etched), in step 616, to leave a substantially substrate-free, mesh structure. The substantially substrate-free, mesh structure is transferred to a bioresorbable substrate in step 618, for example using transfer printing, such as dry contact transfer printing.

Figure 7:
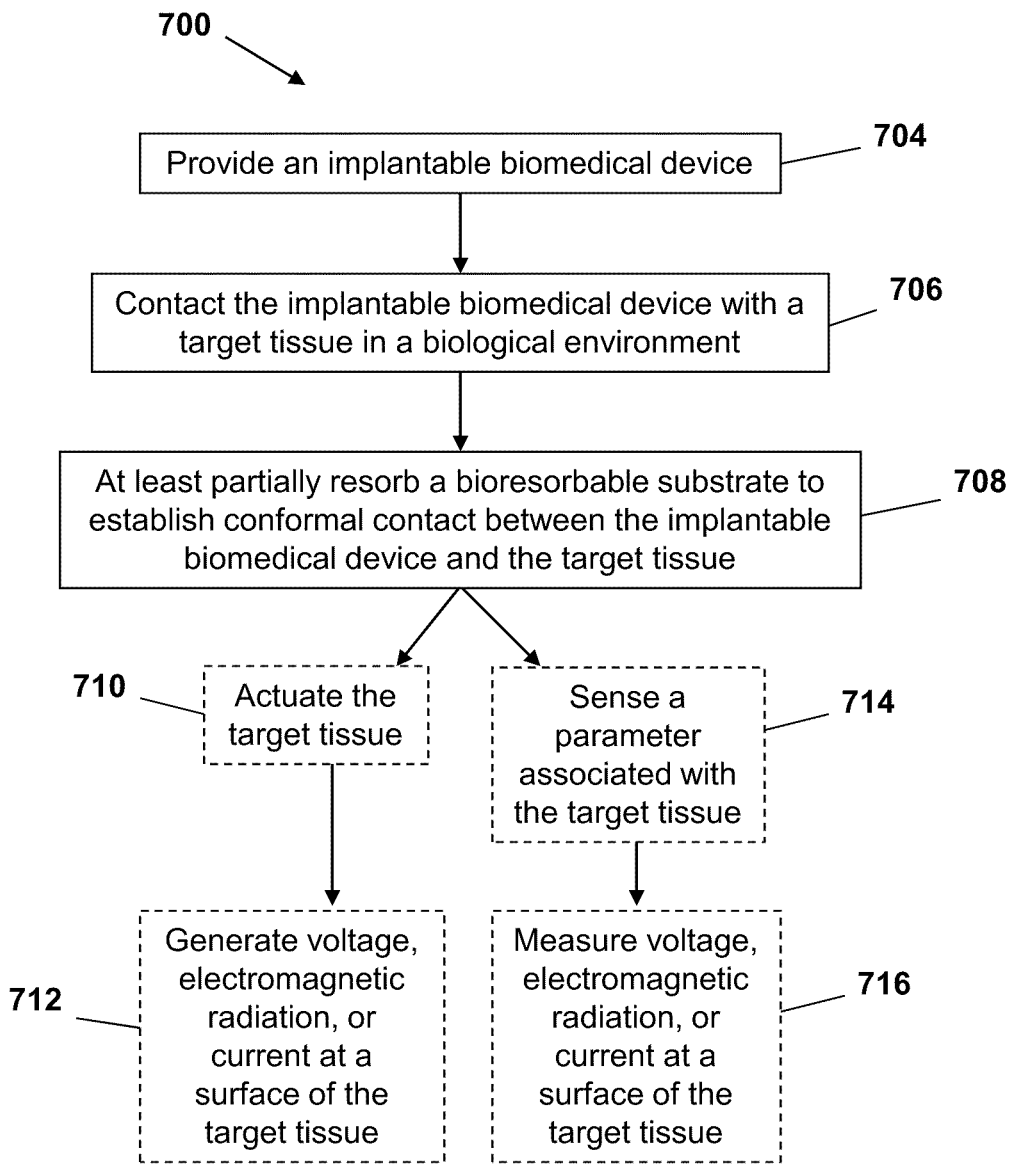
FIG. 7 provides a flowchart illustrating exemplary steps for implanting a biomedical device, and optionally using the implanted biomedical device to actuate a target tissue and/or sense a parameter associated with the target tissue.

FIG. 7 provides a flowchart 700 illustrating exemplary steps for implanting a biomedical device 100, and optionally using the implanted biomedical device to actuate a target tissue and/or sense a parameter associated with the target tissue. In step 704, an implantable biomedical device 100 is provided. The implantable biomedical device is then contacted, in step 706, with a target tissue in a biological environment and a bioresorbable substrate of the implantable biomedical device is at least partially resorbed to establish conformal contact between the implantable biomedical device and the target tissue, in step 708. In optional step 710, the target tissue is actuated. A voltage, electromagnetic radiation or current may be generated at a surface of the target tissue, in optional step 712. In another optional step, 714, a parameter associated with the target tissue may be sensed. A voltage, electromagnetic radiation or current may be measured at a surface of the target tissue, in optional step 716. Steps 710 and 712 for actuating the target tissue and steps 714 and 716 for sensing a parameter associated with the tissue are not mutually exclusive. For example, in one embodiment, a portion of semiconductor components of an implantable biomedical device may actuate the target tissue while another portion senses parameters associated with the target tissue. In another embodiment, all the semiconductor components of an implantable biomedical device may alternately sense and actuate, e.g., in accordance with a feedback loop.

FIGS. 8a and 8b show side plan views of implantable biomedical devices 100(6) and 100(7) having planar contact surfaces 802 and nanostructured or microstructured contact surfaces 804, respectively. As shown in FIG. 8, barrier layer 104 interfaces with the target tissue. However, in alternate embodiments, bioresorbable substrate 102 may interface with the target tissue, and bioresorbable substrate 102 may be planar or structured. Structured contact surfaces 804, have nanometer-sized or micrometer-sized relief features 806, such as barbs 808, spikes 810, and protrusions 812, which may extend a length, x, from a surface of implantable biomedical device 100(7).

In some embodiments, implantable biomedical devices advantageously utilize silk as a bioresorbable substrate. Silk is biocompatible, FDA-approved, optically transparent, mechanically robust (high mechanical modulus and toughness), and flexible in thin film form. It is also compatible with aqueous processing, which preserves sensitive electronic functions, and amenable to chemical and biological functionalization. The presence of diverse amino acid side chains facilitates coupling chemistry for functionalizing silks. Silk is also water soluble with programmable rates of proteolytic biodegradation (yielding non-inflammatory amino acids) over a range from minutes to hours to years.

Some other natural polymers that exhibit properties similar to or analogous to silk include, but are not limited to, chitosan, collagen, gelatin, agarose, chitin, polyhydroxyalkanoates, pullan, starch (amylose amylopectin), cellulose, hyaluronic acid, or any combination of these.

Silk may be obtained from various natural sources, for example, from the silkworm *Bombyx mori* or from the spider *Nephila clavipes*. Silk solutions used in accordance with embodiments of the present invention may be obtained, for example, from a solution containing a dissolved silkworm silk (e.g. from *Bombyx mori*), a dissolved spider silk (e.g. from *Nephila clavipes*), or from a solution containing a recombinant silk, such as from bacteria, yeast, mammalian cells, transgenic animals, or transgenic plants.

In an embodiment, the silk of the bioresorbable substrate may be silk fibroin protein, which consists of layers of antiparallel beta sheets and has a primary structure consisting mainly of the recurrent amino acid sequence (Gly-Ser-Gly-Ala-Gly-Ala)$_n$. Fibroin is known to arrange itself in three structures, called silk I, II, and III. Silk I is the natural, amorphous form of fibroin, as emitted from the *Bombyx mori* silk glands. Silk II refers to the crystalline arrangement of fibroin molecules in spun silk, which has greater strength. Silk III is formed principally in solutions of fibroin at an interface (i.e. air-water interface, water-oil interface, etc.). In the disclosed implantable biomedical devices, silk I, II and/or III may be used.

Silk substrates were typically prepared from material derived from *Bombyx mori* cocoons, according to published procedures. See, Sofia, S., McCarthy, M. B., Gronowicz, G. & Kaplan, D. L. Functionalized silk-based biomaterials for bone formation. *J. Biomed. Mater. Res.* 54, 139-148 (2001); Perry, H., Gopinath, A., Kaplan, D. L., Negro, L. D. & Omenetto, F. G. Nano- and micropatterning of optically transparent, mechanically robust, biocompatible silk fibroin films. *Adv. Mater.* 20, 3070-3072 (2008); and WO 2008/108838. Briefly, boiling the cocoons in a 0.02 M aqueous solution of sodium carbonate for 60 minutes removed sericin, a water-soluble glycoprotein that binds fibroin filaments in the cocoon but which can induce undesirable immunological responses. An aqueous solution of lithium bromide at 60° C. solubilized the silk fibroin fibers and subsequent dialysis removed the lithium bromide. Centrifugation followed by microfiltration eliminated particulates to yield solutions of 8-10% silk fibroin with minimal contaminants.

Using an alternate method, silk solutions may be prepared using organic solvents, as described in WO 2008/108838 which is hereby incorporated by reference in its entirety. Use of organic solvents in the preparation of silk materials can alter the biocompatibility and physical properties of silk materials. For example, immersion of silk films in organic solvents, such as methanol, may cause dehydration of the hydrated or swollen structure, leading to crystallization and, thus, loss of solubility in water. Further, the use of organic solvents can render the silk material less degradable.

As noted above, the presence of organic solvents, as compared to aqueous solvents, in the silk solution, may generate silk substrates with more crystalline structures, as compared to amorphous structures. This phenomenon may be used to control, for example, the rate of bioresorption of the silk. Accordingly, depending on the desired resorption rate, the silk solution may be prepared using any suitable ratio of aqueous:organic solution, for example, 100% aqueous, about 80% aqueous, about 60% aqueous, about 50% aqueous, about 40% aqueous, about 20% aqueous, or about 10% aqueous.

Additional techniques may be used to control the bioresorption rate of the silk substrate. For example, the rate at which resorption occurs may be tailored by altering: substrate material, substrate thickness, crosslinking, the extent of interchain hydrogen bonding or Van der Weals forces, and/or molecular alignment (e.g., via mono-axial or bi-axial stretching, spinning into fiber, and/or weaving). In an embodiment, it may be desirable to rapidly resorb the bioresorbable substrate at the time of device implantation. Bioresorption may be accelerated, for example, by washing the implanted device with water or saline.

Additional bioresorbable polymers including, but not limited to, a biopolymer, a synthetic polymer, a protein, a polysaccharide, poly(glycerol-sebacate) (PGS), polydioxanone, poly(lactic-co-glycolic acid) (PLGA), polylactic acid (PLA), collagen, chitosan, or any combination of these, may be used alone as the bioresorbable substrate or may be added to the silk solution to generate composite silk substrates. In one embodiment, a substrate comprises from about 50 to about 99.99 parts by volume (vol %) silk protein solution and from about 0.01 to about 50 vol % additional polymer.

In some aspects, implantable biomedical devices described herein may be used for drug delivery. In one embodiment, one or more therapeutic agents may be encapsulated within the substrate material as a liquid, a gel, a dispersed solid, or any other appropriate physical form, to be administered to a patient upon resorption of the substrate. To form these therapeutically enhanced substrate materials, the silk or other bioresorbable polymer solution may be mixed with one or more therapeutic agents, and optionally a pharmaceutically acceptable carrier, prior to forming the substrate. Any pharmaceutical carrier that does not dissolve the bioresorbable material may be used.

In some embodiments, implantable biomedical devices of the invention are used to administer, deliver and/or activate a therapeutic agent provided to a subject. In an embodiment of this aspect, the bioresorbable substrate is a multifunctional component that releases a therapeutic agent upon administration to a biological environment and/or contact with a target tissue. The invention includes, for example, bioresorbable substrates having embedded therapeutic agents, such as drugs (e.g., small molecule therapeutics), nanoparticles and/or biomolecules, such as proteins, peptides, oligonucleotides (e.g., DNA or RNA), etc. This aspect of the present invention may be useful for a range of therapeutic applications including controlled release of therapeutic agents and/or targeted administration of therapeutic agents to a selected tissue type. Release of the therapeutic agent in these embodiments may occur by processes mediated by resorption of the bioresorbable substrate in contact with a target tissue. The invention includes implantable devices and systems wherein the electronic device component mediates release of therapeutic agent from the bioresorbable substrate via thermal means, for example by local heating of components of the implantable device, such as the bioresorbable substrate. The invention includes implantable devices and systems wherein the electronic device component mediates release of therapeutic agent from the bioresorbable substrate via processes driven by generation and control of local electric fields, such as electrophoresis processes for the release of proteins or peptides. The invention includes implantable devices and systems wherein the electronic device component mediates release and/or activation of a therapeutic agent from the bioresorbable substrate via processes driven by absorption of electromagnetic radiation. In an embodiment, the implantable device includes an electronic device component, such as a laser or LED array, capable of optically activating a therapeutic agent during and/or upon release from the bioresorbable substrate. This aspect of the invention is useful for therapeutic applications including phototherapy.

Therapeutic agents that may be used in conjunction with the devices described herein include, but are not limited to: small molecules; proteins; peptides; nucleotides; nucleic acids; carbohydrates; simple sugars; cells; genes; anti-thrombotics; anti-metabolics; anticoagulants; antimitotics; fibrinolytics; anti-inflammatory steroids; monoclonal antibodies; vitamins; sedatives; steroids; hypnotics; antiinfectives, such as antibiotics and antiviral agents; chemotherapeutic agents (i.e., anticancer agents); prostaglandins, radiopharmaceuticals, anti-rejection agents; analgesics; anti-inflammatory agents; hormones, such as steroids; growth factors (inhibitors and promoters), such as epidermal growth factor, fibroblast growth factor, platelet-derived growth factor, insulin-like growth factor, transforming growth factors, and vascular endothelial growth factor; anti-angiogenic proteins such as endostatin; polysaccharides; glycoproteins; lipoproteins; and any combination of these.

For example, a therapeutic agent circulating through an in-vivo biological environment may be activated when it receives electromagnetic radiation from a biomedical device implanted at a therapeutic site. In particular, energy within the ultraviolet and visible regions of the electromagnetic spectrum may be useful.

The invention may be further understood by the following non-limiting examples.

EXAMPLE 1

Silicon Electronics on Silk as a Path to Bioresorbable, Implantable Devices

Many existing and envisioned classes of implantable biomedical devices require high performance electronics/sensors. An approach that avoids some of the longer term challenges in biocompatibility involves a construction in which some parts or all of the system resorbs in the body over time. This example describes strategies for integrating single crystalline silicon electronics, where the silicon is in the form of nanomembranes, onto water soluble and biocompatible silk substrates. Electrical, bending, water dissolution and animal toxicity studies suggest that this approach might provide many opportunities for future biomedical devices and clinical applications.

Advanced implantable bioMedical devices have great potential in clinical applications. Systems that allow insertion into the body to establish conformal contact with the curvilinear surfaces of various organs must be flexible and biocompatible. The conformal and flexible characteristics could be enabled by recently reported organic, inorganic, and nanomaterial based electronics. Achieving biocompatibility, on the other hand, can be challenging, due to the complex nature of the biological response to many organic and inorganic materials. An ideal solution to this problem that largely avoids the longer term issues involves the construction of the electronics out of materials that are soluble and biodegradable; here the device simply disappears, or resorbs, over time. Alternatively, a large fraction of the device can be designed to resorb, such that a sufficiently small amount of material remains that its induced biological response is negligible. This approach has the advantage that it does not require the development of an entire set of biodegradable electronic materials, but still yields an overall system that dissipates bulk material features at a rate suitable for the application. This example describes the combination of silicon electronics, based on nanomembranes of silicon, with biodegradable thin film substrates of silk protein, to yield a flexible system and device that is largely resorbable in the body. The use of silicon provides high performance, good reliability, and robust operation. Silk is attractive, compared to other biodegradable polymers such as poly(glycolic acid), poly(L-lactic acid), and collagen, because of its robust mechanical properties, the ability to tailor the dissolution, and/or biodegradation rates from hours to years, the formation of noninflammatory amino acid degradation products, and the option to prepare the materials at ambient conditions to preserve sensitive electronic functions FIG. 9 shows the schematic fabrication process. Single crystalline nanomembranes of silicon (thickness ~260 nm p-type, SOITEC, France) were used to construct transistors on ultrathin sheets of polyimide (PI). Briefly, the doped silicon nanomembranes were transfer printed onto a film of PI (PI, ~1.2 μm, Sigma Aldrich, USA) cast onto a thin sacrificial layer of poly(methylmethacrylate) (PMMA, ~100 nm, A2 PMMA, MicroChem, USA) on a silicon wafer (i.e., carrier wafer for processing). After printing, a series of fabrication processes, including photolithography, reactive ion etching, plasma enhanced chemical vapor deposition of oxides, and electron beam evaporation of metals, formed silicon metal oxide field effect transistors connected by metal lines. Next, spin coating a layer of PI (~1.2 μm) encapsulated the active devices and located them near the neutral mechanical plane. Dry etching the polymer layers completed the fabrication of an array of isolated devices on PMMA, as shown in FIG. 9(a). Next, dissolving the PMMA with acetone released the devices from the carrier wafer. These devices were lifted onto the surface of a transfer stamp of poly(dimethylsiloxane) (PDMS, Sylgard 184, Dow Corning, USA), as shown in FIG. 9(b). Transfer printing delivered the devices to either a spin cast film of silk on a silicon substrate (FIG. 9(c)) or a freestanding silk membrane (FIG. 9(d)). To accomplish transfer at high yield, a ~7% aqueous silk solution was spin coated on the backsides of the devices while on the PDMS stamp, at spin rates between 2000 and 3000 rpm for 30 s. This layer of silk served as an adhesive for a transfer, which involves first establishing conformal contact with the silk substrate while on a hot plate (~110° C.) and then slowly retrieving the stamp. This process yielded a system in which the substrate is water soluble, and resorbable, but the devices are not, as shown in the schematic diagram in FIG. 9(d). An important point is that the devices can be constructed in very small dimensions (interconnected or not, depending on the application), with very small total amounts of material, thereby offering the possibility to minimize their effects on the biology. Further, the mode of processing the silk can be designed to yield rapid dissolution rates, as is the case here, or to degrade over years.

FIG. 10(a) shows a freestanding silk film with transfer printed silicon devices. The center and right frames of FIG. 10(a) demonstrate the mechanical flexibility of the system. Under bending at these levels (radius of curvature, R, as ~5 mm), no mechanical or adhesive failure was observed. It is estimated that the bend induced strains at the top surface of the silk film (~25 μm, ~5 mm bending radius) are in the range of ~0.25%. Electrical measurements of a typical n channel device show expected properties (solid line of FIG. 10(b)). Here, the channel length and width was 13 and 100 μm, respectively, and the gate oxide thickness was 50 nm. The electron mobility, threshold voltage, and on/off ratio calculated from the transfer curve in the left frame of FIG. 10(b) are ~500 $cm^2/V$ s, ~0.2 V, and $>10^4$, respectively. The current-voltage characteristics at different gate biases are shown in the right frame of FIG. 10(b). The gate leakage current was less than tens of picoamperes. Also, the nMOS transistor was characterized after dissolving the silk substrate in water and then filtering out the devices onto filter paper (dotted line of FIG. 10(b)). Even after dissolution, the transistors functioned with only modest changes in properties. The electron mobility, threshold voltage, and on/off ratio were estimated from the transfer curves to be ~440 $cm^2/V$ s, ~0.5 V, and $>10^4$.

This dissolution process relies on the capability of silk to disintegrate in water, leaving proteins as the products that are then degraded by proteolytic activity. The resulting silk fibroin protein is a Food and Drug Administration (FDA) approved biocompatible material that generates noninflammatory amino acid degradation products usable in cell metabolic functions. Further, the mechanical properties of the silk substrate can be tailored, based on the mode of processing, to match the level of toughness required. To illustrate the process, images were collected at various times after dipping a typical device into a petri dish filled with water, at room temperature. With a ~25 μm thick silk substrate, complete dissolution within 3 min was observed, as shown in FIGS. 11(a) and 11(b). FIG. 11(c) shows devices recovered onto a piece of filter paper. Since the vast majority of this type of implantable device consists of the substrate and because the sizes of the active devices can be reduced even further by using standard microelectronic technology, very tiny or negligible residues of nonresorbable materials can remain after dissolution.

Figure 12:
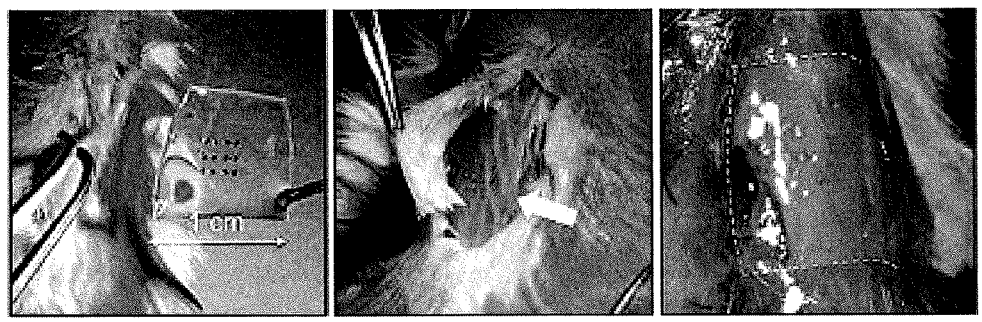
FIG. 12 provides photographs of a biomedical device implanted in a mouse model. Procedure and result of the animal toxicity test: image before (left) and shortly after (center) and two weeks after (right) implantation.

Similar types of devices were implanted into animals to determine the inflammatory response. Here, the devices consisted of doped silicon, silicon dioxide, and metal layers encapsulated with PI, similar to those described previously. Since PI and gold are known to be biocompatible, the main concerns were for the silicon and silicon dioxide. Recent reports on the biocompatibility of porous nanoparticles of silicon and silicon dioxide suggest the possibility of biocompatibility in the $Si/SiO_2$ components used in the transistors. To examine this issue directly, samples were implanted subcutaneously in mice (left and center frame of FIG. 12) and retrieved after two weeks. The results show the partial dissolution of the film in this time frame, as well as the lack of any inflammation around the implant site. The mice did not exhibit any sign of abscessing or liquid buildup, and initial integration of the silk carrier into the subcutaneous layers could be observed. The size of the implant is estimated to be between 15%-20% smaller than the originally implanted device and detachment of a few transistor structures can be observed, as shown in the right frame of FIG. 12. Although additional studies are required, these initial in vivo tests suggest some promise for this form of biodegradable electronics.

In conclusion, unconventional material processing and device fabrication procedures have been developed for a class of implantable biomedical device that is largely, but not completely, bioresorbable. The systems combine an FDA approved biomaterial substrate, silk, and with silicon nanomaterial electronic devices. Preliminary in vivo toxicity and inflammatory evaluations showed no harmful effects on a living animal. A technology of this type could open various possible applications for insertion of high performance flexible electronics into implantable biomedical devices. Further, since silk is the toughest known natural biopolymer in fiber form, this substrate provides a suitable base substrate upon which to develop a family of such implantable devices, where in vivo lifetime of components can be tailored from short to long term, hours to years.

REFERENCES

K. D. Wise, A. M. Sodagar, Y. Yao, M. N. Gulari, G. E. Perlin, and K. Najafi, Proc. IEEE 96, 1184 (2008).
Y. Sun and J. A. Rogers, Adv. Mater. (Weinheim, Ger.) 19, 1897 (2007).
Q. Cao and J. A. Rogers, Adv. Mater. (Weinheim, Ger.) 21, 29 (2009).
S. R. Forrest, Nature (London) 428, 911 (2004).
Y. Wang, D. D. Rudymb, A. Walsh, L. Abrahamsen, H.-J. Kim, H. S. Kim, C. Kirker-Head, and D. L. Kaplan, Biomaterials 29, 3415 (2008).
C. Vepari and D. L. Kaplan, Prog. Polym. Sci. 32, 991 (2007).
D.-H. Kim, W. M. Choi, J.-H. Ahn, H.-S. Kim, J. Song, Y. Y. Huang, Z. Liu, C. Lu, C. G. Koh, and J. A. Rogers, Appl. Phys. Lett. 93, 044102 (2008).
D.-H. Kim, J. Song, W. M. Choi, H.-S. Kim, R.-H. Kim, Z. Liu, Y. Y. Huange, K.-C. Hwang, Y.-W. Zhang, and J. A. Rogers, Proc. Natl. Acad. Sci. U.S.A. 105, 18675 (2008).
R. L. Horan, K. Antle, A. L. Collette, Y. Wang, J. Huang, J. E. Moreau, V. Volloch, D. L. Kaplan, and G. H. Altman, Biomaterials 26, 3385 (2005).
H.-J. Jin, J. Park, U.-J. Kim, R. Valluzzi, P. Cebe, and D. L. Kaplan, Biomacromolecules 5, 711 (2004).
H. J. Jin, J. Park, V. Karageorgiou, U. J. Kim, R. Valluzzi, R. Cebe, and D. L. Kaplan, Adv. Funct. Mater. 15, 1241 (2005).
J. D. Yeager, D. J. Phillips, D. M. Rector, and D. F. Bahr, J. Neurosci. Methods 173, 279 (2008).
J.-H. Park, L. Gu, G. V. Maltzahn, E. Ruoslahti, S. N. Bhatia, and M. J. Sailor, Nature Mater. 8, 331 (2009).

EXAMPLE 2

Dissolvable Films of Silk Fibroin for Ultrathin, Conformal Bio-Integrated Electronics Electronics that are capable of intimate, non-invasive integration with the soft, curvilinear surfaces of biological tissues offer important opportunities for diagnosing and treating disease and for improving brain-machine interfaces. This example describes a material strategy for a type of bio-interfaced system that relies on ultrathin electronics supported by bioresorbable substrates of silk fibroin. Mounting such devices on tissue and then allowing the silk to dissolve and resorb initiates a spontaneous, conformal wrapping process driven by capillary forces at the biotic/abiotic interface. Specialized mesh designs and ultrathin forms for the electronics ensure minimal stresses on the tissue and highly conformal coverage, even for complex curvilinear surfaces. Combined experimental and theoretical studies of the materials and underlying mechanics reveal the key mechanisms. In vivo, neural mapping experiments on feline animal models illustrate one mode of use for this class of technology. These concepts provide capabilities for implantable or surgical devices that lie outside those of wafer-based technologies or known forms of flexible electronics.

Strategies for bio-integrated electronics must overcome the challenges associated with the mismatch between the hard, planar surfaces of semiconductor wafers and the soft, curvilinear tissues of biological systems. These differences in mechanics and form lead, almost invariably, to low fidelity coupling at the biotic/abiotic interface and limited long-term tissue health. The difficulties are most pronounced and the solutions are perhaps most important in systems designed for brain-computer interfaces (BCIs). Penetrating microelectrode arrays consisting of sharp pins (typically, 10×10 arrays of pins with base widths ~80 μm, lengths ~1.5 mm and pitch ~400 μm) that connect to flat platforms for conventional wafer-based electronics are valuable for research in BCI, but they damage the tissue and do not offer long-term electrical interface stability. Comparable BCI performance can be achieved with non-penetrating, surface electrode systems that are minimally-invasive and provide greatly improved stability. Standard clinical subdural electrode arrays are useful for BCI but their widely spaced (~1 cm), large contact electrodes (~0.35 cm diameter) spatially undersample the electrical signals present on the surface of the brain. Decreasing the spacing and size of the measurement points can improve BCI performance by providing access to high temporal and spatial frequency signals. Such designs, however, demand excellent conformal coverage over the highly convoluted brain surface to ensure direct coupling between the brain surface and the electrodes.

Reducing the thickness of the substrate decreases the bending rigidity, thereby improving conformal contact. Unfortunately, clinical arrays and even the thinnest devices designed for research have thicknesses (700 μm and >10 μm, respectively) that are larger than desired. In conventional designs, ultrathin geometries (i.e. <10 μm; thinner better) are impractical because the films are not sufficiently self-supporting to be manipulated effectively during fabrication or implantation. Another disadvantage is that even extremely thin, flexible systems can only wrap shapes with zero Gaussian curvature (i.e. developable surfaces such as cylinders and cones). Complex surfaces of tissue like the brain are impossible without introducing wrinkles or folds. This example presents solutions to these two problems, via the combined use of ultrathin electronics (down to <3 μm) in highly open, mesh geometries mounted on sacrificial, bioresorbable silk fibroin substrates.

Silk is an appealing biopolymer for this application because it is optically transparent, mechanically robust and flexible in thin film form, compatible with aqueous processing, amenable to chemical and biological functionalization, and it is biocompatible, bioresorbable, and water soluble with programmable rates of dissolution. In addition, the ability of silk films to serve as a platform for transistors and various classes of photonic devices has been demonstrated. The process for preparing silk substrates for the purposes reported here began with material derived from *Bombyx mori* cocoons, and followed published procedures. Briefly, boiling the cocoons in a 0.02 M aqueous solution of sodium carbonate for 60 minutes removed sericin, a water-soluble glycoprotein that binds fibroin filaments in the cocoon but can induce undesirable immunological responses. An aqueous solution of lithium bromide at 60° C. solubilized the fibers and subsequent dialysis removed the lithium bromide. Centrifugation followed by micro-filtration eliminated particulates to yield solutions of 8%-10% silk fibroin with minimal contaminants. Casting a small amount of the solution on a flat piece of poly(dimethylsiloxane) (PDMS) followed by crystallization in air (~12 h) yielded uniform films (thickness of 20-50 μm) (FIG. 13a) that were subsequently removed from the PDMS for integration with separately fabricated electronics.

Figure 14:
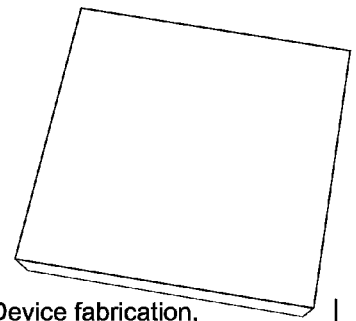
FIGS. 14a, 14b and 14c provide images of an implantable biomedical device fabrication process using a thick polyimide film. Electrode array fabrication process using thick PI film (Kapton, Dupont, USA). a, attach PI film to PDMS coated glass. b, electrode array fabrication. c, ACF connection.
Figure 14:
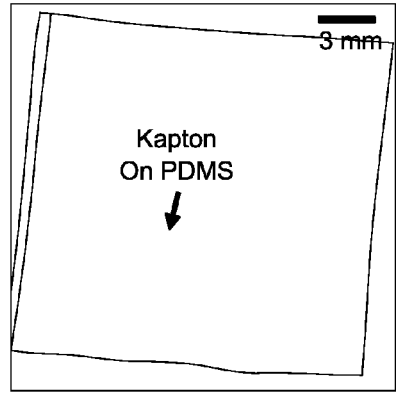
Figure 14:
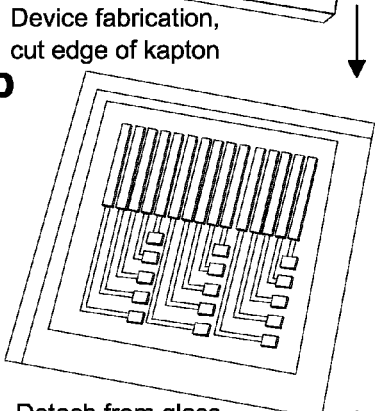
Figure 14:
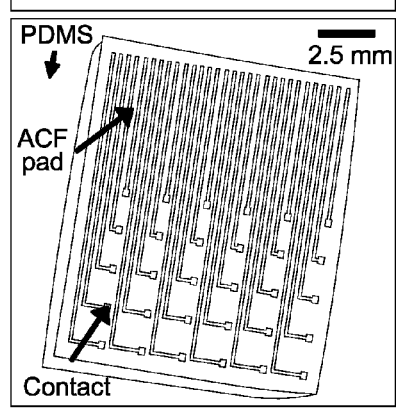
Figure 14:
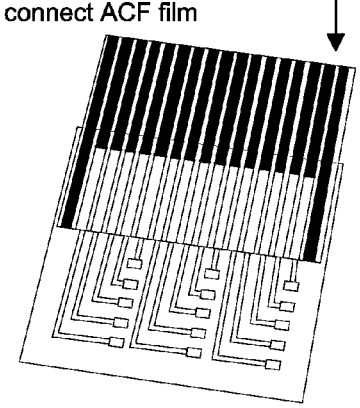
Figure 14:
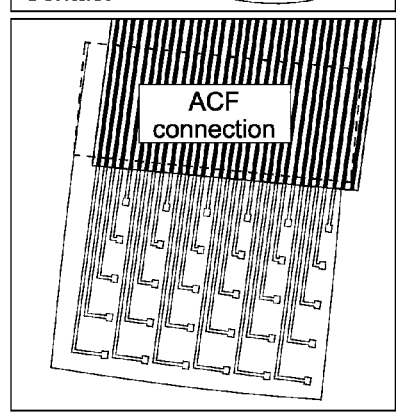

For the systems described in the following, polyimide (PI) served as a support for arrays of electrodes designed for passive neural recording. Control devices consisted of otherwise similar layouts, but formed using standard photolithographic procedures applied directly on commercial PI films (Kapton, DuPont) with thicknesses of 25 and 75 μm (FIG. 14). Anisotropic conductive film (ACF) bonded to electrode pads at one end of the arrays provided electrical connection to the external data acquisition system (FIG. 15). Ultrathin PI films, with or without mesh layouts, cannot be manipulated effectively for processing, interconnecting or implanting onto the brain due to their extreme flexibility and mechanical fragility. For these cases, the fabrication process exploited layers of PI spin cast onto silicon wafers coated with sacrificial films of poly(methylmethacrylate) (PMMA) (left frame of FIG. 13b). After the electrode fabrication, the mesh structure devices underwent further etching to remove unwanted parts of the PI. The processing was completed by dissolving the PMMA layer with acetone, transfer printing the entire assembly to a film of silk and connecting the ACF, yielding easily manipulated bioresorbable neural recording systems. See schematic illustrations and images of FIG. 13b. In all cases, the electrode arrays consisted of 30 measurement electrodes (Au, 150 nm) in a 6×5 configuration, each with dimensions of 500 μm×500 μm and spaced by 2 mm. Interconnection wires to each electrode were protected by a thin (~1.2 μm) overcoat of PI to prevent contact with the tissue. Details of the fabrication steps appear in the methods section. The electrode arrays were implanted by placing them on the brain and then flushing with saline to dissolve the silk, thereby inducing spontaneous, conformal wrapping of the device, as illustrated schematically for the mesh design in FIG. 13c.

Figure 16A:
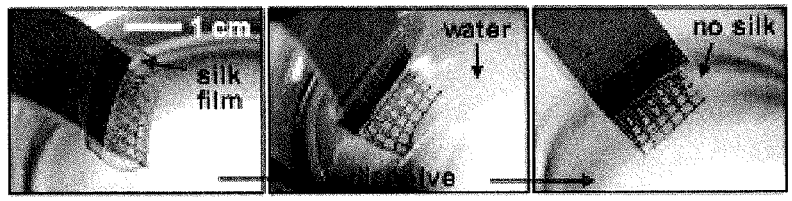
FIGS. 16a, 16b, 16c show time-dependent changes as a silk substrate dissolves. Time dependent changes as the silk substrate dissolves. a, Dissolution of the silk via submersion in warm water. b, Total bending stiffness of 7 μm and 2.5 μm electrode arrays on supporting silk films as a function of thickness of the supporting silk film; inset shows the ratio of bending stiffness between 7 μm and 2.5 μm. c, Time dependent change in volume of a silk film during dissolution (left frame) and bending stiffness calculated for silk treated in 70% ethanol for 5 seconds for two different array thicknesses (right frame). The 5 second ethanol treatment increases the dissolution time from minutes to about 1 hour.
Figure 16B:
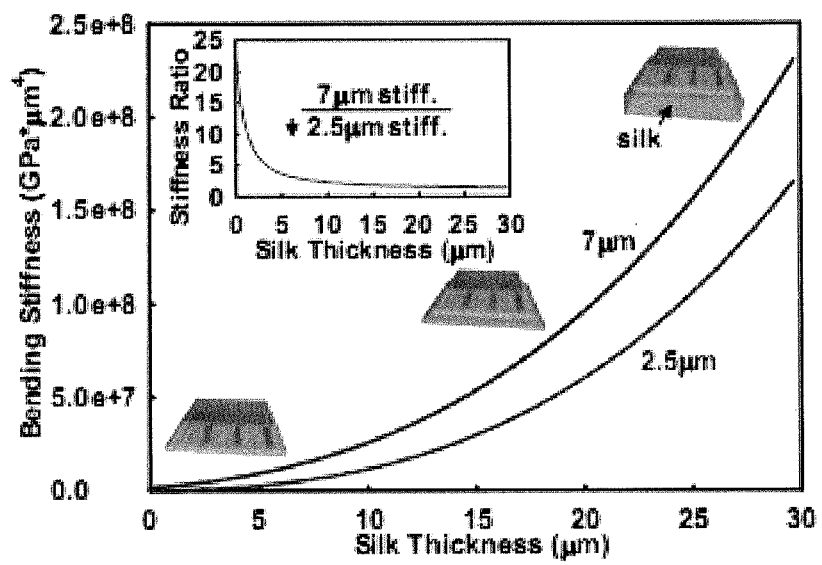
Figure 16C:
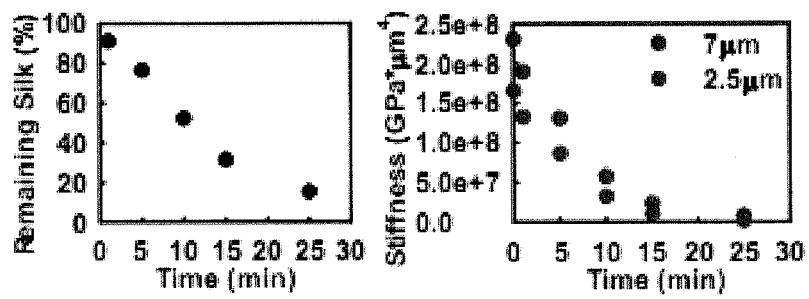
Figure 16D:
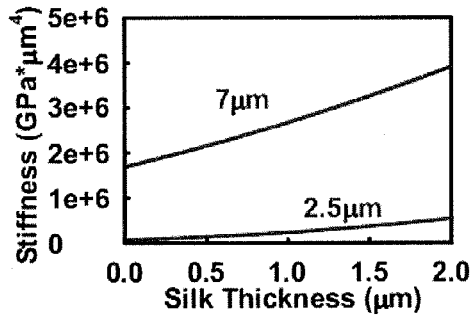
FIG. 16d shows The bending stiffness of the neural sensor of thickness 7 μm and 2.5 μm on a silk backing substrate.
Figure 17:
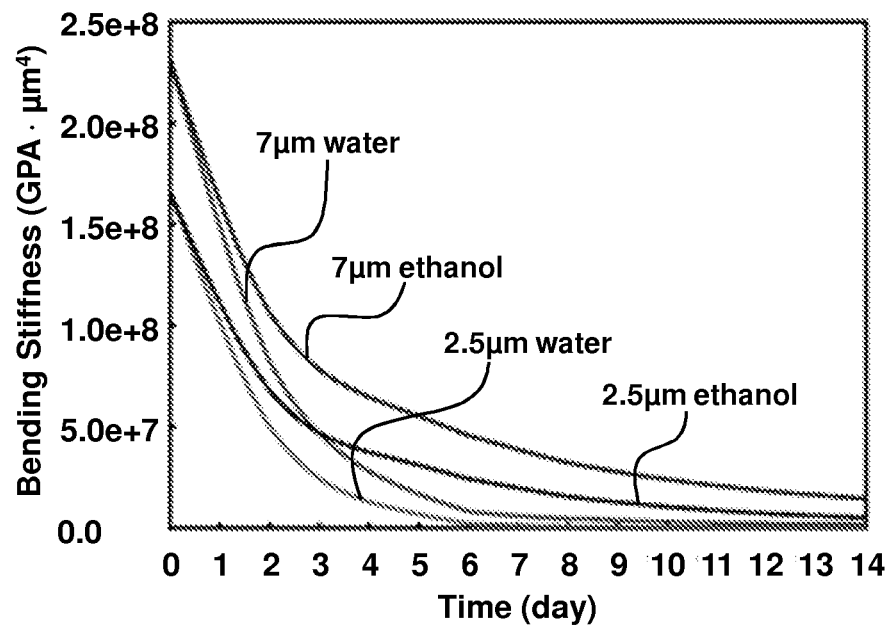
FIG. 17 shows time-dependent bending stiffness changes for 7 μm and 2.5 μm implantable biomedical devices.

The sequence of images in FIG. 16a shows the dissolution process for a representative case (7 μm thick PI film, connected to ACF on a silk substrate with thickness of ~25 μm) inserted into warm water (~35° C.). As the silk substrate disappears, the total bending stiffness, EI, diminishes dramatically due to its cubic dependence on thickness. Computed results appear in FIG. 16b and FIG. 16d for PI thicknesses of 2.5 and 7 μm. To highlight the benefits of reduced thickness, the inset shows the ratio of EI for these two cases. Through programmed control of the dissolution rate via modifications of the silk protein secondary structure, these changes in EI can be designed to occur over periods of time ranging from seconds to years, depending on requirements. FIG. 16c shows, as an example, the dissolution rate of silk film slightly treated with ethanol (left frame) and computed time dependence of EI in devices that employ more thorough ethanol treatment (right frame). See below for detailed conditions. This dissolution time can be lengthened even more by extending the treatment time to days or weeks; the corresponding time dependence of EI appears in FIG. 17.

Figure 18A:
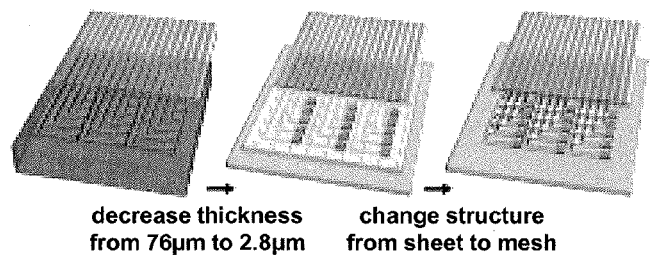
FIGS. 18a, 18b, 18c and 18d show photographs of neural implantable biomedical devices of varying thickness on simulated brain models. Neural electrode arrays of varying thickness on simulated brain models to illustrate flexibility. a, Schematic illustration of trends in thickness and structure that improve conformal contact. b, Series of pictures illustrating how the thickness of the electrode array contributes to conformal contact on a brain model. c, Magnified view of these pictures. d, Image of an electrode array with a mesh design on dissolvable silk substrate. Arrows indicate struts in the mesh that help to stabilize the Au interconnects after dissolution of the silk. The inset illustrates the high degree of conformal contact that can be achieved on the brain model once the silk substrate has been dissolved.
Figure 18B:
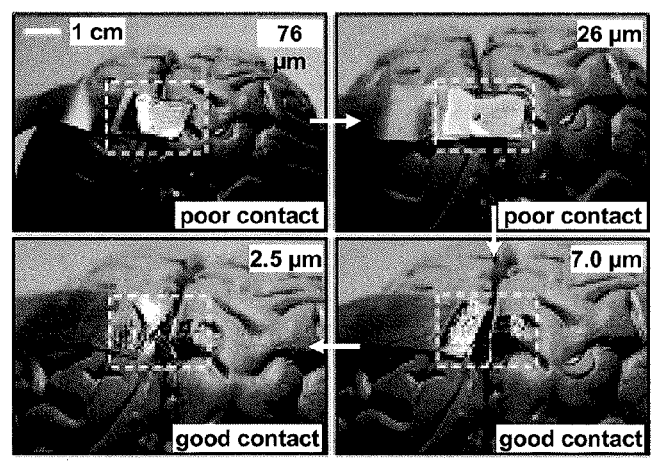
Figure 18C:
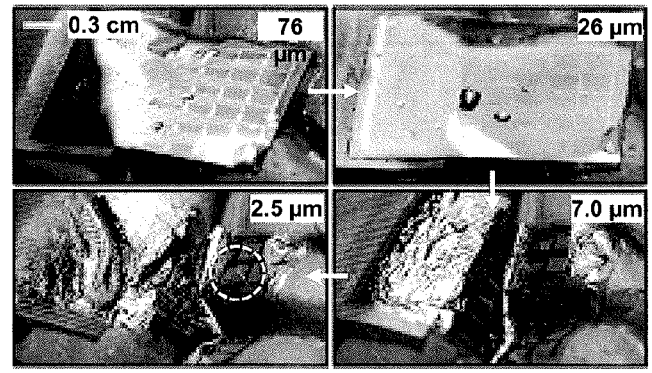
Figure 18D:
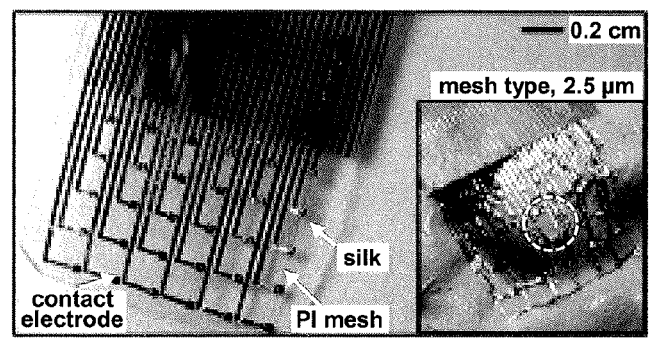
Figure 19:
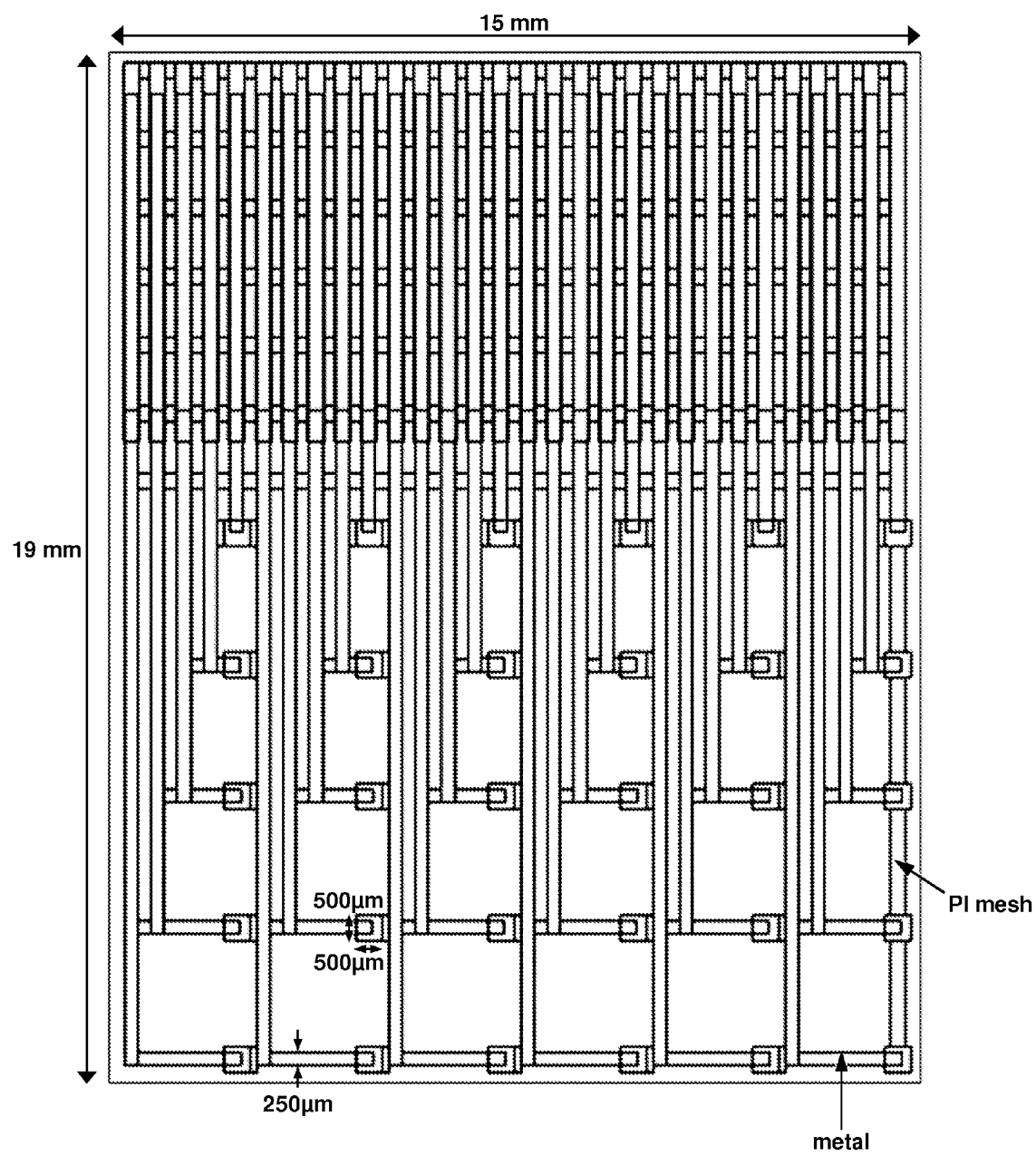
FIG. 19 shows design parameters for a mesh electrode array.

To examine the ability of these systems to conform to relevant surfaces, experiments were performed using a human brain model, following the basic steps shown in FIG. 13c. FIG. 18 provides images for various cases after washing with saline, including relatively thick control devices that do not incorporate silk. Clearly, the extent of conformal coverage increases with decreasing thickness; the mesh design provides further improvements, as shown in FIGS. 18d, 19 and 20. To reveal the underlying mechanics, systematic and quantitative studies were performed on well-defined surfaces that capture certain basic features of the curvature of the brain. The first set of experiments explored wrapping the devices on isolated and overlapped cylindrical surfaces. FIG. 21a shows the simplest case of a device with bending stiffness EI, thickness h, width b and length 2 L, wrapped on a cylinder with radius R. Analytical expressions for EI can be written for the multilayer structures of FIG. 13 in terms of material properties and geometries, as described below. The unwrapped state (top frame of FIG. 21a) corresponds to zero energy. The energy of the wrapped state (center frame of FIG. 21a) consists of two parts, the bending energy of the thin film $U_b = EIL/R^2$, and the adhesion energy between the thin film and the cylinder $U_a = -2\gamma bL$, where $\gamma$ is the adhesion energy per unit area. For the wrapped state to be energetically favorable, $U_b + U_a \leq 0$, which gives $$\gamma \geq \gamma_c = \frac{EI}{2R^2 b}. \tag{1}$$

The bottom frame of FIG. 21a compares the above relation with a series of experiments (FIG. 22). The data are consistent with an adhesion energy per unit area $\gamma$ on the order of 10 mJ/m$^2$, which is comparable to reported values for wet interfaces. Reducing the thickness provides clear benefits, e.g. wrapping cylinders using only capillary adhesion forces is possible for R ~1 cm when h<~15 μm.

A pair of overlapped cylinders represents a simple model for a gyrus of the brain. FIG. 21b shows cylinders with radii R, a center-to-center separation of 2d and connected by a smooth arc of radius $r_0$, at the angular position $\theta_0 \sin^{-1}[d/(R+r_0)]$. As with the single cylinder, the energy of the unwrapped state (top frame of FIG. 21b) was chosen to be zero. The wrapped configuration involves bending energy of the film and adhesion energy at the interface, according to (see below for details)

$$U_2 = \frac{EI}{R}\left[\frac{R\theta\sin\theta}{d - R\sin\theta} - \left(\frac{\gamma}{\gamma_c} - 1\right)\left(\frac{L}{R} + \theta - \frac{d\theta}{R\sin\theta}\right)\right], \tag{2}$$

where $\gamma_c$ is given in Eq. (1), and $\theta$ is the contact angle of thin film with one cylinder, which is determined by minimizing $U_2$ to give $$\frac{R\sin\theta}{d - R\sin\theta} + \frac{dR\theta\cos\theta}{(d - R\sin\theta)^2} - \left(\frac{\gamma}{\gamma_c} - 1\right)\left(1 - \frac{d}{R\sin\theta} + \frac{d\theta\cos\theta}{R\sin^2\theta}\right) = 0. \tag{3}$$

The solution of Eq. 3 takes the form $\theta = \theta(d/R, \gamma/\gamma_c)$. For $\gamma_c < \gamma'_c$, the energy has a minimum at $\theta = 0$, and the film does not wrap around the cylinders. Partial wrapping occurs to a contact angle of $\theta$ (i.e. contact for angles between 0 and $\theta < \theta_0$) for $\gamma_c \leq \gamma < \gamma'_c$, where $\gamma'_c$ is obtained from Eq. (3) with $\theta = \theta_0$ as $\gamma'_c = \gamma_c\{1 + (1+\lambda)R^2/[(1-\lambda)r_0^2]\}$ and $\lambda = r_0 d/\{(R+r_0)$ $\sqrt{(R+r_0)^2-d^2}\sin^{-1}[d/(R+r_0)]\}$. For $\gamma \geq \gamma'_c$, wrapping is complete (i.e. conformal contact for angles between 0 and $\theta_0$)). By comparing Eq. (3) with the experiment in FIG. 23, the extracted adhesion energy per unit area is found to be $\gamma=10$ mJ/m². Results appear in the bottom frame of FIG. 21b, where the parameters correspond roughly to features on the brain model: R=6.14 mm, d=5.93 mm and $r_0$=1.72 mm. (Experimental images appear in FIG. 23.) The critical thickness for conformal contact is $h_0$=4.9 µm, i.e., devices thinner than ~4.9 µm achieve conformal contact on this surface. The experimental results are consistent with this calculation.

Figure 21C:
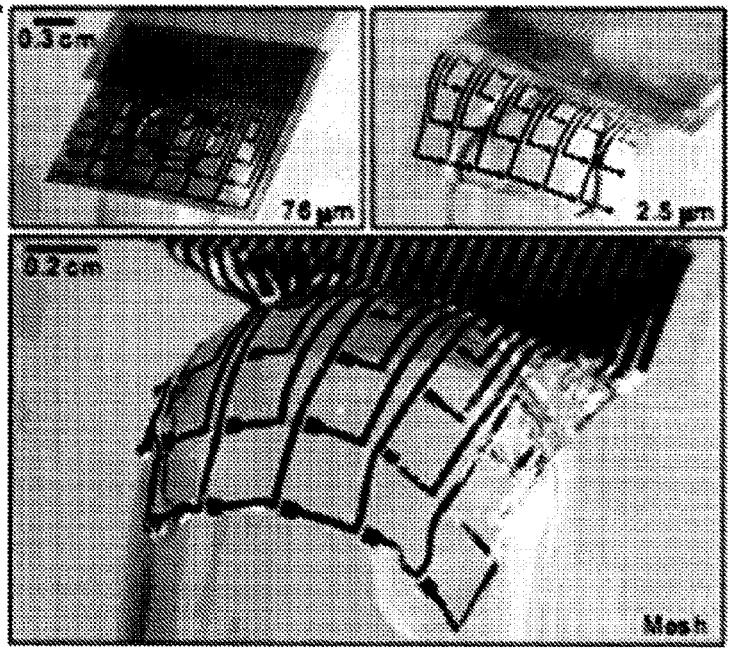
Figure 21D:
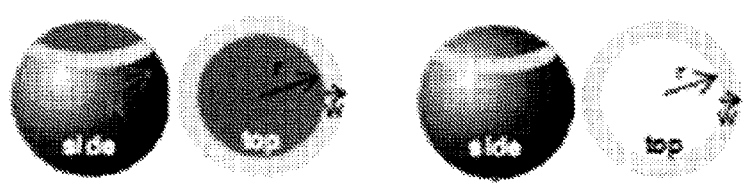

Cylindrical surfaces like those of FIGS. 21a and 21b are developable; the brain is not. As a model of non-developable surface, the case of a hemispherical substrate was examined. FIG. 21c shows results for electrode arrays with sheet designs at thicknesses of 7 and 2.5 µm and with an open mesh layout at 2.5 µm, each on a glass hemisphere with radius of curvature of 6.3 mm. With only water capillarity as the adhesion force, the mesh electrode array achieves excellent conformal contact. The sheets show comparatively poor contact, with large wrinkles, even for the thinnest case (i.e. 2.5 µm). Mechanical analysis of a simple model reveals the underlying physics. The left frame of FIG. 21d shows the case of a circular film with radius r+w wrapped onto a sphere with radius R. The central green part denotes a Pl plate of radius r, tension stiffness $(Eh)_{Pl}$ and equi-biaxial bending stiffness $(EI)_{Pl}$. The yellow ring corresponds to a multilayer structure of Pl and Au, of width w, tension stiffness $(Eh)_{composite}$ and equi-biaxial bending stiffness $(EI)_{composite}$. For the film to wrap around the sphere, the required minimum adhesion energy per unit area is obtained analytically as $$\gamma_c^{sheet} = \frac{(EI)_{Pl}}{R^2} + \frac{(EI)_{Pl}}{r^2}\int_0^r \left(1 - \frac{R}{x}\sin\frac{x}{R}\right)^2 x\,dx + \frac{2w(EI)_{composite}}{rR^2} + \frac{w(Eh)_{composite}}{r}\left(1 - \frac{R}{r}\sin\frac{r}{R}\right)^2. \quad (4)$$

A model for the mesh design that consists of only a circular strip of a corresponding multilayer of Pl and Au appears in the right frame of FIG. 21d. In this case, the minimum adhesion energy per unit area is $$\gamma_c^{mesh} = \frac{(EI)_{composite}}{R^2} + \frac{w^2(Eh)_{composite}}{24r^2}\left(1 - \sqrt{1-\frac{r^2}{R^2}}\right)^2. \quad (5)$$

Figure 21E:
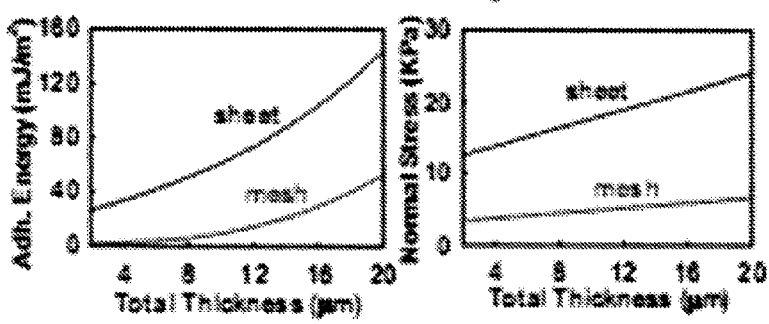
Figure 24A:
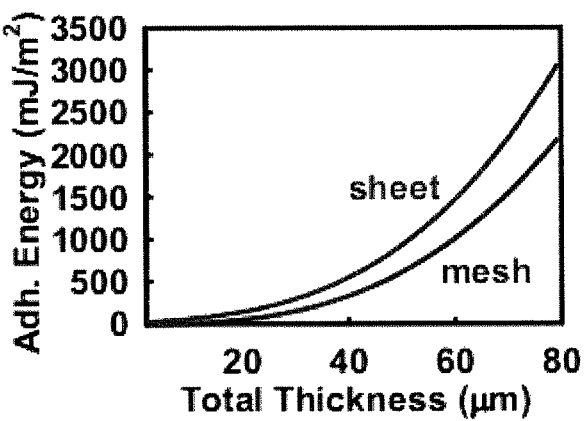
FIGS. 24a and 24b provide modeling results for the critical adhesion energy and normal (peeling) stress, respectively. a, The critical adhesion energy for sheet and mesh designs. b, The normal (peeling) stress between the film and sphere surface for sheet and mesh designs.
Figure 24B:
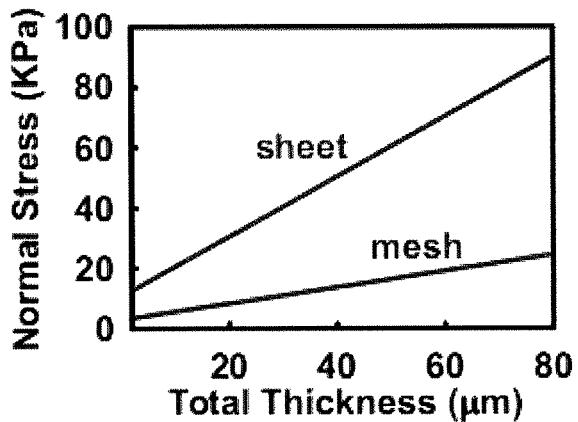

For the case that w<<r, $\gamma_c^{sheet}$ in Eq. (4) is always larger than $\gamma_c^{mesh}$ in Eq. (5), i.e., $\gamma_c^{sheet} > \gamma_c^{mesh}$. The inference is that the open mesh design requires much lower adhesion energy than the corresponding sheet, thereby leading to greatly improved ability for conformal coverage, as shown in the left frame of FIG. 21e. FIG. 24a shows critical adhesion energies for films with thicknesses up to 80 µm. For a thickness of 2.5 µm and w/r=4, $\gamma_c^{sheet}$=29.1 mJ/m² for the sheet, which is more than 12 times larger than the mesh $\gamma_c^{mesh}$=2.4 mJ/m². In addition, the mesh design involves membrane strains that are smaller, by roughly a factor of w/r, compared to sheets with similar thickness. For the experimental mesh systems, this ratio is on the order of 1/4. As a result, for a representative critical wrinkling strain of 0.1%, nearly two thirds of the sheet will wrinkle. Under the same conditions, the entire mesh gives perfect, conformal contact. Finally, the normal (peeling) interfacial stresses for the mesh is only 1/4 of that for the sheet (right frame of FIG. 21e and FIG. 24b), leading to improved adhesion and reduced forces applied to the substrate. See below for details.

In-vivo neural monitoring experiments on a feline animal model demonstrated the practical implications of these favorable mechanics. The tests involved an anesthetized cat mounted in a sterotaxic apparatus with its eyes focused on a monitor that subtended 28×22 degrees of space. An initial craniotomy and durotomy exposed a 2×3 cm region of cortex. The electrode arrays covered much of visual cortex, as shown in the left frames of FIGS. 25a, b and c. Visual stimuli consisted of full-field drifting gratings presented for 1 second at 2 Hz with a spatial frequency of 0.5 cycles/degree. Gratings were presented at 2 different directions over 8 different orientations (16 unique stimuli).

Figure 25:
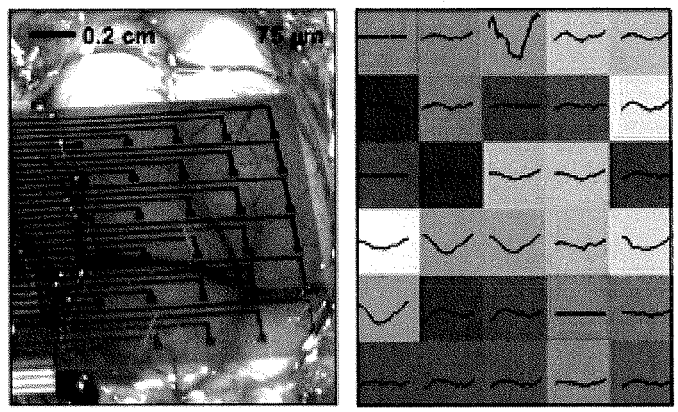
FIGS. 25a, 25b, 25c and 25d provide photographs and data from animal validation experiments. Photographs and data from animal validation experiments. Image of electrode array on cat brain (left) and average evoked response from each electrode with the color showing the extent of cross-correlation between the evoked response on each electrode and an average of all the responses (right) for 75 µm a, 2.5 µm b and 2.5 µm mesh c electrode array. d, Representative voltage data from a single electrode in a 2.5 µm mesh electrode array showing a sleep spindle.
Figure 25:
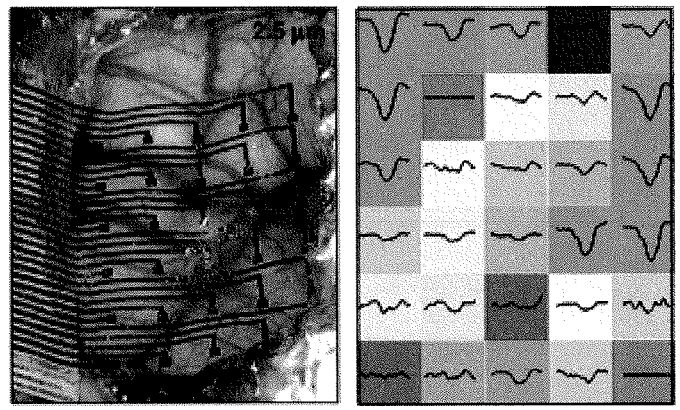
Figure 25:
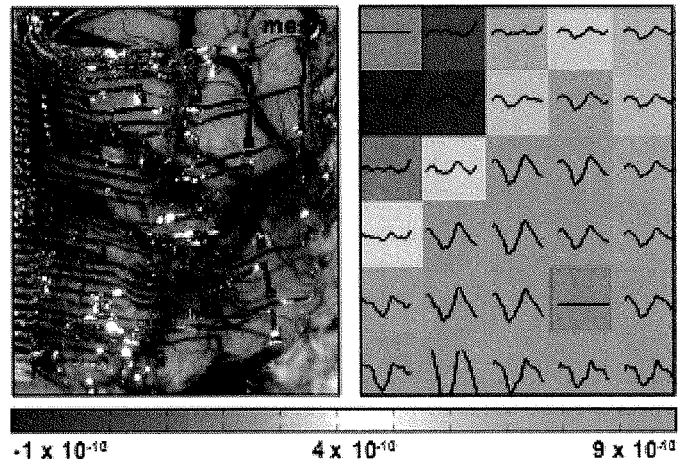
Figure 25:

Three kinds of electrode arrays were used for comparison: 76 µm and 2.5 µm thick sheets and a 2.5 µm thick mesh. The second two included dissolvable silk supports. The left images of FIGS. 25a, b and c illustrate the progressively improved conformal contact with reduced thickness (i.e. 76 µm to 2.5 µm, in FIGS. 25a and b, respectively) and with introduction of the mesh (i.e. FIG. 25c). The right frames of FIGS. 25a, b and c demonstrate the effectiveness of decreasing the electrode thickness and the mesh structure on physiological measurements of brain activity. In particular, these frames show the average evoked response measured at each electrode, each plotted in a spatial orientation that corresponds to the images in the left frames. The background color of each plot illustrates the zero-lag cross-correlation between the evoked response on that electrode and an average of all the responses from the entire array. The color bar at the bottom of FIG. 25c provides the numerical scale for all of the colors used in FIGS. 25a, b and c. This measurement serves as a quantitative metric of the electrode performance, because the uniform nature of the stimulation is expected to evoke similar responses across the entire visual cortex. In each case, 28 of the 30 electrode channels were recorded and evaluated for evoked potential response, as colored in green through red. Two channels, indicated in grey, served as local reference. The channels with high and low correlations to the average response are colored green and red, respectively. The 76 µm (FIG. 25a) electrode array exhibited the fewest channels with good response, due to poor contact at many of the electrodes. The 2.5 µm array (FIG. 25b) showed better conformal contact and correspondingly more channels with good responses. The 2.5 µm mesh electrode (FIG. 25c) showed the best performance, with nearly all channels in good contact and with highly correlated responses. FIG. 25d shows representative single channel data from one of the 2.5 µm mesh electrodes. A sleep spindle is observed with good signal amplitude and signal to noise ratio. This collective set of observations is consistent with the systematic mechanics studies described previously.

In summary, this example introduces a class of conformal electronics capable of intimate integration on the soft, curvilinear surfaces of biological tissues. The approaches rely on dissolvable, biocompatible and bioresorbable substrates, where dissolution and capillary forces drive a wrapping process in a non-invasive manner. Although purely passive electrode systems serve to demonstrate the advantages and underlying aspects of these systems, the same approaches are compatible with fully active electronics and optoelectronics. As a result, these concepts may have the potential to yield important technologies for human health, by providing capabilities that are unavailable with established classes of implantable devices.

METHODS. THICK ELECTRODE ARRAY (>25 μM) FABRICATION. Commercial Pl films (Kapton, Dupont, USA) with thicknesses of 25 and 75 μm were attached to a temporary carrier substrate consisting of a glass slide coated with PDMS. After cleaning the surfaces with acetone, isopropyl alcohol (IPA) and deionized (DI) water, electron beam evaporation formed uniform coatings of metal (Cr/Au, 50/1450 A). Photolithography and patterned etching yielded arrays of interconnect lines. Thin layers of Pl (thickness ~1.2 μm) spin cast and patterned by reactive ion etching left only the ends of the lines exposed. Additional deposition and patterning defined square metal electrode pads at these locations. Peeling away from the PDMS coated glass slide and bonding to on ACF cable, using procedures described in a separate section, completed the fabrication. FIG. 14 provides a schematic diagram and images of the process.

THIN ELECTRODE ARRAY (<10 μM) FABRICATION. The fabrication in this case used a carrier silicon wafer coated with a thin (~1.2 μm) spin cast layer of poly(methylmethacrylate) (PMMA, A2, MicroChem, USA). The device substrate consisted of a film of Pl (Sigma Aldrich, USA) spin cast onto the PMMA. Procedures similar to those described for thick devices formed the metal electrodes and Pl overcoat. After fabrication, the ultrathin devices were released by dissolving the sacrificial PMMA layer. Transfer printing with a PDMS stamp delivered the devices to dry silk film substrates, coated with ~9% silk solution as an adhesive. The final step involved bonding of an ACF cable.

MESH ELECTRODE ARRAY (<10 μM) FABRICATION. The first and last parts of the fabrication sequence were identical to the steps outlined in the previous section. The only difference was the addition of a step to remove certain regions of the polymer layers (i.e. Pl and underlying PMMA) by oxygen reactive ion etching through a mask (design in FIG. 26) to define the mesh structure. Detailed dimensions are as follows: thickness ~2.5 μm, contact electrode size 500 μm×500 μm, mesh width ~250 μm. (See more details in FIG. 19) This etching immediately followed the formation of the electrode pads.

ACF CONNECTION. The contact pads on the electrode array were first aligned with the ACF cable. Metal clips were used to apply pressure, spread evenly over the contact pad area using a piece of PDMS inserted between the ACF and the clips. Next, the clamped sample and ACF were placed in an oven preheated to ~150° C. for ~15 min. This process formed a strong mechanical bond between the electrode array and the ACF with low electrical resistance.

Figure 27:
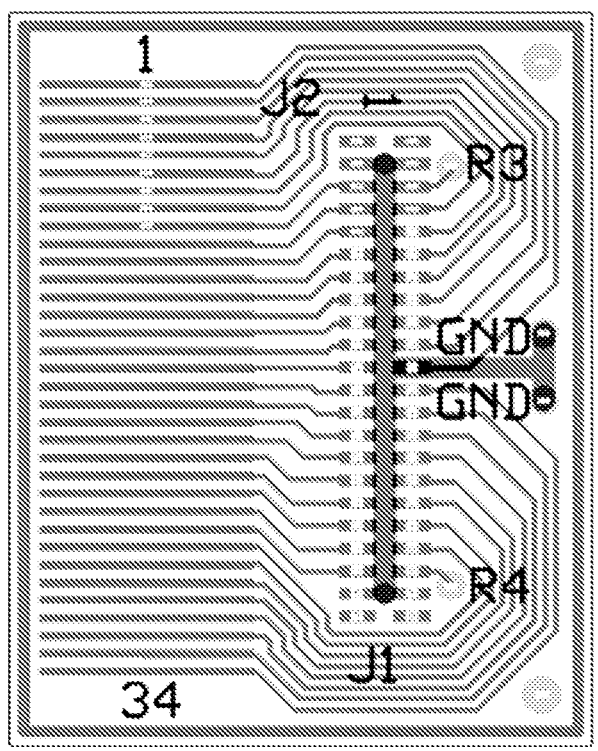
FIG. 27 shows the design of a circuit board.

ACQUISITION SYSTEM. The electrode arrays were connected to a Neuralynx DigitalLynx data acquisition system via anisotropic conductive film (ACF) and a custom electrode interface board. The board appears in FIG. 27. FIG. 15 shows the connected electrode array, ACF ribbon and circuit board.

ANIMAL EXPERIMENTS. Animal experiments were conducted according to protocol. Anesthesia was obtained by an intraperitoneal injection of thiopental (25 mg/kg). Subsequent inhalent isofluroane was administered during cannulation of a branch of the femoral vein. Following cannulation, anesthesia was maintained through thiopental infusion (8-12 mg/hr) and supplemented by intermittent thiopental boluses. The level of anesthesia was constantly monitored through the use of an EEG (presence of "sleep spindles" and slow wave oscillations), a $CO_2$ Monitor (~4%), and a blood pressure and heart rate monitor (~180-200 bpm).

SUPPLEMENTARY INFORMATION. Silk dissolution test. By altering the secondary structure of a silk film, one can program the amount of time it takes for the film to dissolve in water. In some embodiments, it is desirable for the film to dissolve within minitues, or within hours. No treatment was required to make the film dissolve in miniutes. Creating some beta sheet structure by exposing to 70% ethanol for approximately 5 seconds increased the dissolution time to approximately 1 hour. To determine a dissolution rate, 51 square inch films were made, exposed to ethanol for 5 seconds, put in a room temperature water bath and their dry weight after a certain time in the water bath was measured. See FIG. 16c.

The bending stiffness of the thin film. The cross sectional geometry of the thin film is illustrated in FIG. 26a. There are n gold bricks (size $b_m \times h_m$, Young's modulus $E_{Au}$=78 GPa and Poisson's ratio $v_{Au}$=0.44) surrounded by Pl (size b×h, Young's modulus $E_{Pl}$=2.5 GPa and Poisson's ratio $v_{Pl}$=0.34). The distance between the neutral axis and bottom of the thin film is $$y_0 = \frac{h}{2} \frac{1 + \frac{2h' + h_m}{h}\left(\frac{E_{Au}}{E_{Pl}} - 1\right)\frac{nb_m h_m}{bh}}{1 + \left(\frac{E_{Au}}{E_{Pl}} - 1\right)\frac{nb_m h_m}{bh}}, \quad (S1)$$

where h' is the distance between bottoms of gold bricks and thin film. The bending stiffness of the thin film is $$EI = E_{Pl} bh\left(\frac{1}{3}h^2 - hy_0 + y_0^2\right) + \\ (E_{Au} - E_{Pl})nb_m h_m\left[\frac{1}{3}h_m^2 + h_m(h' - y_0) + (h' - y_0)^2\right]. \quad (S2)$$

The bending stiffness of the thin film on a silk backing substrate. The cross sectional geometry of the thin film on a silk backing substrate is illustrated in FIG. 26b. The silk backing substrate has a thickness H and Young's modulus $E_{Silk}$=2.8 GPa. The distance between the neutral axis and bottom of the thin film is $$y_0 = \frac{h}{2} \frac{1 + \frac{2h' + h_m}{h}\left(\frac{E_{Au}}{E_{Pl}} - 1\right)\frac{nb_m h_m}{bh} - \frac{E_{silk} H^2}{E_{Pl} h^2}}{1 + \left(\frac{E_{Au}}{E_{Pl}} - 1\right)\frac{nb_m h_m}{bh} + \frac{E_{silk} H}{E_{Pl} h}}. \quad (S3)$$

The bending stiffness of the thin film is $$EI = E_{Pl} bh\left(\frac{1}{3}h^2 - hy_0 + y_0^2\right) + E_{silk} bH\left(\frac{1}{3}H^2 + Hy_0 + y_0^2\right) + \\ (E_{Au} - E_{Pl})nb_m h_m\left[\frac{1}{3}h_m^2 + h_m(h' - y_0) + (h' - y_0)^2\right]. \quad (S4)$$

A thin film wrapping around two overlapped cylinders. The beam theory gives the unwrapped part of thin film (above the connecting arc in the center frame of FIG. 21b) is (part of) a circle of radius r given by $$r = \frac{d}{\sin\theta} - R. \quad (S5)$$

The bending energy in the thin film is obtained as $$U_b = EI\frac{1}{r^2}r\theta + EI\frac{1}{R^2}(L - r\theta) \quad \text{(S6)}$$
$$= EI\frac{\theta\sin\theta}{d - R\sin\theta} + \frac{EI}{R^2}\left(L + R\theta - \frac{d\theta}{\sin\theta}\right).$$

The adhesion energy is $$U_b = -2\gamma b\left(L + R\theta - \frac{d\theta}{\sin\theta}\right). \quad \text{(S7)}$$

The total energy of the wrapped state is the summation of the above bending energy and adhesion energy.

$$U_2 = \frac{EI}{R}\left[\frac{R\theta\sin\theta}{d - R\sin\theta} - \left(\frac{\gamma}{\gamma_c} - 1\right)\left(\frac{L}{R} + \theta - \frac{d\theta}{R\sin\theta}\right)\right], \quad \text{(S8)}$$

where $\gamma_c$ is given in Eq. (1).

Mechanics model for mesh design. For the sheet design as shown in the left frame of FIG. 21d, the thin film is modeled as a plate. The central green part denotes the Pl plate of radius r, tension stiffness $(Eh)_{Pl} = \bar{E}_{Pl}h$ and equi-biaxial bending stiffness $(EI)_{Pl} = \bar{E}_{Pl}(1+v_{Pl})h^3/12$, where $\bar{E}_{Pl} = E_{Pl}/(1-v_{Pl}^2)$ is the plane-strain modulus of Pl. The yellow ring is the sandwiched composite of Pl and Au of width w, tension stiffness $(Eh)_{composite} = \bar{E}_{Pl}h + (\bar{E}_{Au} - \bar{E}_{Pl})h_m$ and equi-biaxial bending stiffness $$(EI)_{composite} = \bar{E}_{Pl}(1 + v_{Pl})h\left(\frac{1}{3}h^2 - hy_1 + y_1^2\right) +$$
$$[\bar{E}_{Au}(1 + v_{Au}) - \bar{E}_{Pl}(1 + v_{Pl})]\left[\frac{1}{3}h_m^2 + h_m(h' - y_1) + (h' - y_1)^2\right]h_m,$$

where $$y_1 = \frac{h}{2}\frac{1 + \frac{(2h' + h_m)h_m}{h^2}\left[\frac{\bar{E}_{Au}(1 + v_{Au})}{\bar{E}_{Pl}(1 + v_{Pl})} - 1\right]}{1 + \left[\frac{\bar{E}_{Au}(1 + v_{Au})}{\bar{E}_{Pl}(1 + v_{Pl})} - 1\right]\frac{h_m}{h}}$$

is the distance between the neutral axis and bottom of the thin film, and $\bar{E}_{Au} = E_{Au}/(1-v_{Au}^2)$ is the plane-strain modulus of Au. The total energy of the wrapped state, which is composed of the bending energy and membrane energy in the thin film and the adhesion energy between the thin film and sphere, is given analytically as $$U_{sheet} = \frac{\pi r^2}{R^2}(EI)_{Pl} + \pi(Eh)_{Pl}\int_0^r\left(1 - \frac{R}{x}\sin\frac{x}{R}\right)^2 x\,dx + \quad \text{(S9)}$$
$$\frac{2\pi rw}{R^2}(EI)_{composite} + \pi rw(Eh)_{composite}\left(1 - \frac{R}{r}\sin\frac{r}{R}\right)^2 - \pi r^2\gamma.$$

For the thin film to wrap around the sphere, $U_{sheet} \leq 0$, which gives the required minimum adhesion energy per unit area $\gamma_c^{sheet}$ in Eq. (4). The maximum circumferential membrane strain is $$\varepsilon_m^{sheet} = -\left(1 - \frac{R}{r+w}\sin\frac{r+w}{R}\right). \quad \text{(S10)}$$

The maximum interfacial normal (peeling) stress is obtained as $$\sigma_{normal}^{sheet} = \quad \text{(S11)}$$
$$\frac{\bar{E}_{Pl}(1 + v_{Pl})(h - h_m) + \bar{E}_{Au}(1 + v_{Au})h_m}{R}\left(1 - \frac{R}{r+w}\sin\frac{r+w}{R}\right).$$

For the mesh design as shown in the right frame of FIG. 21d, the total energy of the wrapped state, which is also composed of the bending energy and membrane energy in the yellow composite ring and the adhesion energy between the thin film and the sphere, is given analytically as $$U_{mesh} = \quad \text{(S12)}$$
$$\frac{2\pi rw}{R^2}(EI)_{composite} + \pi(Eh)_{composite}\frac{w^3}{12r}\left(1 - \sqrt{1 - \frac{r^2}{R^2}}\right)^2 - 2\pi rw\gamma.$$

From $U_{mesh} \leq 0$ for the thin film to wrap around the sphere, the required minimum adhesion energy per unit area $\gamma_c^{mesh}$ in Eq. (5) is obtained. The maximum circumferential membrane strain is $$\varepsilon_m^{mesh} = -\left[1 - \frac{R}{r+w}\sin\left(\frac{w}{2R} + \arcsin\frac{2r+w}{2R}\right)\right]. \quad \text{(S13)}$$

The maximum interfacial normal (peeling) stress is obtained as $$\sigma_{normal}^{sheet} = \quad \text{(S14)}$$
$$\frac{\bar{E}_{Pl}(1 + v_{Pl})(h - h_m) + \bar{E}_{Au}(1 + v_{Au})h_m}{R}\frac{w}{2r}\left(1 - \sqrt{1 - \frac{r^2}{R^2}}\right).$$

REFERENCES

Kim, S. et al. Integrated wireless neural interface based on the utah electrode array. *Biomed. Microdevices* 11, 453-466 (2009).

Ryu, S. I. & Shenoy, K. V. Human cortical prostheses: lost in translation? *Neurosurg Focus* 27, (1):E5 (2009).

Andersen, R. A., Musallam, S. & Pesaran, B. Selecting the signals for a brain-machine interface. *Current Opinion in Neurobiology* 14, 720-726 (2004).

Mehring C. at al. Inference of hand movements from local field potentials in monkey motor cortex. *Nature Neurosci.* 6, 1253-1254 (2003).

Ball, T. et al. Towards an implantable brain-machine interface based on epicortical field potentials. *Biomed. Tech.* 49, 756-759 (2004).

Wilson, J. A., Felton, E. A., Garell, P. C.: Schalk, G. & Williams, J. C. ECoG factors underlying multimodal control of a brain-computer interface. *IEEE Trans. Neural Syst. Rehabil. Eng.* 14, 246-250 (2006).

Freeman, W. J., Rogers, L. J., Holmes, M. D. & Silbergeld, D. L. Spatial spectral analysis of human electrocorticograms including the alpha and gamma bands. *J. Neurosci. Methods* 95, 111-121 (2000).

Kellis, S. S., House, P. A., Thomson, K. E., Brown, R., & Greger, B. Human neocortical electrical activity recorded on nonpenetrating microwire arrays: applicability for neuroprostheses. *Neurosurg. Focus* 27, (1):E9 (2009).

Rubehn, B., Bosman, C., Oostenveld, R., Fries, P. & Stieglitz, T. A MEMSbased flexible multichannel ECoG-electrode array. *J. Neural Eng.* 6, 036003 (2009).

Hollenberg, B. A., Richards, C. D., Richards, R., Bahr, D. F. & Rector, D. M. A MEMS fabricated flexible electrode array for recording surface field potentials. *J. Neurosci. Methods* 153, 147-153 (2006).

Lawrence, B. D., Cronin-Golomb, M., Georgakoudi, I., Kaplan, D. L. & Omenetto, F. G. Bioactive silk protein biomaterial systems for optical devices. *Biomacromolecules* 9, 1214-1220 (2008).

Omenetto, F. G. & Kaplan, D. L. A new route for silk. *Nature Photon.* 2, 641-643 (2008).

Jin, H.-J. et al. Water-stable silk films with reduced β-sheet content. *Adv. Funct. Mater.* 15, 1241-1247 (2005).

Lu, Q. et al. Water-insoluble silk films with silk i structure. *Acta Biomater*. In Press (2009).

Jiang, C. et al. Mechanical properties of robust ultrathin silk fibroin films. *Adv. Funct. Mater.* 17, 2229-2237 (2007).

Sofia, S., McCarthy, M. B., Gronowicz, G. & Kaplan, D. L. Functionalized silkbased biomaterials for bone formation. *J. Biomed. Mater. Res.* 54, 139-148 (2001).

Perry, H., Gopinath, A., Kaplan, D. L., Negro, L. D. & Omenetto, F. G. Nano- and micropatterning of optically transparent, mechanically robust, biocompatible silk fibroin films. *Adv. Mater.* 20, 3070-3072 (2008).

Murphy, A. R., John, P. S. & Kaplan, D. L. Modification of silk fibroin using diazonium coupling chemistry and the effects on hMSC proliferation and differentiation. *Biomaterials* 29, 2829-2838 (2008).

Altman, G. H. et al. Silk-based biomaterials. *Biomaterials* 24, 401-416 (2003).

Santin, M., Motta, A., Freddi, G. & Cannas, M. In vitro evaluation of the inflammatory potential of the silk fibroin. *J. Biomed. Mater. Res.* 46, 382-389 (1999).

Kim, D.-H. et al. Silicon electronics on silk as a path to bioresorbable, implantable devices. *Appl. Phys. Lett.* 95, 133701-133703 (2009).

Amsden, J. J. et al. Spectral analysis of induced color change on periodically nanopatterned silk films. *Opt. Express* 17, 21271-21279 (2009).

Parker, S. T. et al. Biocompatible silk printed optical waveguides. *Adv. Mater.* 21, 2411-2415 (2009).

Soong, H. K. & Kenyon, K. R. Adverse reactions to virgin silk sutures in cataract surgery. *Ophthalmology* 91, 479-483 (1984).

Chaudhury, M. K. & Whitesides G. M. Direct measurement of interfacial interactions between semispherical lenses and flat sheets of poly(dimethylsiloxane) and their chemical derivatives. *Langmuir* 7, 1013-1025 (1991).

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The following references relate generally to flexible and/or stretchable semiconductor materials and devices and are each hereby incorporated by reference in its entirety: U.S. patent application Ser. No. 12/778,588, filed on May 12, 2010, PCT International Application No. PCT/US05/19354, filed Jun. 2, 2005 and published under No. WO2005/122285 on Dec. 22, 2005, U.S. Provisional Patent Application No. 61/313,397, filed Mar. 12, 2010, U.S. patent application Ser. No. 11/851,182, filed Sep. 6, 2007 and published under No. 2008/0157235 on Jul. 3, 2008, and PCT International Application No. PCT/US07/77759, filed Sep. 6, 2007 and published under No. WO2008/030960 on Mar. 13, 2008.

The following references relate generally to bioresorbable substrates and methods of making bioresorbable substrates and are each hereby incorporated by reference in its entirety: PCT Patent Application PCT/US03/19968 filed Jun. 24, 2003, PCT Patent Application PCT/US04/000255 filed Jan. 7, 2004, PCT Patent Application PCT/US04/11199 filed Apr. 12, 2004, PCT Patent Application PCT/US05/20844 filed Jun. 13, 2005, and PCT Patent Application PCT/US06/029826 filed Jul. 28, 2006.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments, exemplary embodiments and optional features, modification and variation of the concepts herein disclosed can be resorted to by those skilled in the art, and that such modifications and variations are considered to be within the scope of this invention as defined by the appended claims. The specific embodiments provided herein are examples of useful embodiments of the invention and it will be apparent to one skilled in the art that the invention can be carried out using a large number of variations of the devices, device components, methods steps set forth in the present description. As will be apparent to one of skill in the art, methods and devices useful for the present methods can include a large number of optional composition and processing elements and steps.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. Nothing herein is to be construed as an admission that the invention is not entitled to antedate such disclosure by virtue of prior invention.

Whenever a range is given in the specification, for example, a range of integers, a temperature range, a time range, a composition range, or concentration range, all intermediate ranges and subranges, as well as all individual values included in the ranges given are intended to be included in the disclosure. As used herein, ranges specifically include the values provided as endpoint values of the range. As used herein, ranges specifically include all the integer values of the range. For example, a range of 1 to 100 specifically includes the end point values of 1 and 100. It will be understood that any subranges or individual values in a range or subrange that are included in the description herein can be excluded from the claims herein.

As used herein, "comprising" is synonymous and can be used interchangeably with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" can be replaced with either of the other two terms. The invention illustratively described herein suitably can be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments and optional features, modification and variation of the concepts herein disclosed can be resorted to by those skilled in the art, and that such modifications and variations are considered to be within the scope of this invention as defined by the appended claims.

We claim:

1. An implantable biomedical device for actuating a target tissue or sensing a parameter associated with the target tissue in a biological environment, said device comprising:
   a bioresorbable substrate;
   an electronic device comprising a plurality of inorganic semiconductor components supported by said bioresorbable substrate, wherein at least one of said inorganic semiconductor components has at least one physical dimension less than or equal to 100 microns; and
   a barrier layer encapsulating at least a portion of said inorganic semiconductor components,
   wherein upon contact with said biological environment said bioresorbable substrate is at least partially resorbed, thereby establishing conformal contact between said implantable biomedical device and said target tissue in said biological environment.

2. The device of claim 1 further comprising a biocompatible layer provided on said bioresorbable substrate, wherein the biocompatible layer is positioned between the electronic device and the bioresorbable substrate.

3. The device of claim 1, wherein said bioresorbable substrate is configured to be completely resorbed upon contact with said biological environment.

4. The device of claim 1, wherein said bioresorbable substrate is configured not to be completely resorbed upon contact with said biological environment.

5. The device of claim 1, wherein resorption of said bioresorbable substrate establishes physical contact or electrical contact between said electronic device and said target tissue.

6. The device of claim 1, wherein resorption of said bioresorbable substrate provides the electronic device in optical communication with said target tissue.

7. The device of claim 1, wherein said bioresorbable substrate comprises a biopolymer, a synthetic polymer, a protein, a polysaccharide, silk or any combination of these.

8. The device of claim 1, wherein said bioresorbable substrate comprises a poly(glycerol-sebacate) (PGS), polydioxanone, poly(lactic-co-glycolic acid) (PLGA), polylactic acid (PLA), collagen, chitosan, fibroin, silkworm fibroin, modified silkworm fibroin, spider silk, insect silk, recombinant silk, or any combination of these.

9. The device of claim 1, wherein said bioresorbable substrate has a thickness selected from the range of 100 nanometers to 10000 µm.

10. The device of claim 1, wherein said bioresorbable substrate has a Young's modulus selected from the range of 0.5 MPa and 10 GPa.

11. The device of claim 1, wherein said bioresorbable substrate has a net bending stiffness selected from the range of $0.1 \times 10^4$ GPa µm$^4$ and $1 \times 10^9$ GPa µm$^4$.

12. The device of claim 1, wherein the bioresorbable substrate has a degree of crystallinity selected from the range of 0 to 55%.

13. The device of claim 1, wherein said implantable biomedical device has a neutral mechanical plane and at least a portion of said plurality of inorganic semiconductor components is positioned proximate to said neutral mechanical plane.

14. The device of claim 1, wherein at least one of said inorganic semiconductor components is a flexible semiconductor structure or a stretchable semiconductor structure.

15. The device of claim 1, wherein at least one of said inorganic semiconductor components is a nanoribbon, a nanomembrane, a nanowire, a transistor channel, a diode, a p-n junction, a photodiode, a light emitting diode, a laser or a combination of these.

16. The device of claim 1, wherein at least one of said inorganic semiconductor components of the electronic device has a thickness less than or equal to 10 microns.

17. The device of claim 1, wherein at least one of said inorganic semiconductor components of the electronic device has a thickness selected from the range of 50 nanometers to 10 microns.

18. The device of claim 1, wherein at least one of said inorganic semiconductor components of the electronic device has a Young's modulus selected from the range of 0.5 MPa to 10 GPa.

19. The device of claim 1, wherein at least one of said inorganic semiconductor components of the electronic device has a net bending stiffness less than or equal to $1 \times 10^8$ GPa $\mu m^4$.

20. The device of claim 1, wherein at least one of said inorganic semiconductor components comprises a single crystal inorganic semiconductor material.

21. The device of claim 1, wherein said electronic device comprises a plurality of island and bridge structures, wherein said island structures comprise one or more of said inorganic semiconductor components of said electronic device, and wherein said bridge structures comprise one or more flexible electrical interconnects.

22. The device of claim 1, wherein said barrier layer comprises material selected from the group consisting of a polymer, an organic polymer, SU-8, an insulator, a polyimide, a dielectric, an inorganic dielectric, $Si_3N_4$, and any combination of these.

23. The device of claim 1, wherein said barrier layer has a thickness selected from the range of 1 μm to 100 μm.

24. The device of claim 1, wherein said bioresorbable substrate, said electronic device, and said barrier layer provide a net bending stiffness of the implantable biomedical device of less than $1 \times 10^9$ GPa $\mu m^4$.

25. The device of claim 1, wherein said barrier layer has a mesh structure.

26. A method for administering an implantable biomedical device, said method comprising:
providing the implantable biomedical device comprising:
a bioresorbable substrate;
an electronic device comprising a plurality of inorganic semiconductor components supported by said bioresorbable substrate, wherein at least one of said inorganic semiconductor components has at least one physical dimension less than or equal to 100 microns; and
a barrier layer encapsulating at least a portion of said inorganic semiconductor components;
contacting said implantable biomedical device with a target tissue in a biological environment; and
at least partially resorbing said bioresorbable substrate in said biological environment, thereby establishing conformal contact between said implantable biomedical device and said target tissue in said biological environment.

27. The method of claim 26, wherein the Young's modulus of said implantable biomedical device decreases by at least 50% upon resorption of the bioresorbable substrate.

28. The method of claim 26, wherein the net bending stiffness of said implantable biomedical device decreases by at least 50% upon resorption of the bioresorbable substrate.

29. The method of claim 26, wherein said biological environment is an in-vivo biological environment.

30. The method of claim 26, wherein said target tissue in said biological environment comprises heart tissue, brain tissue, muscle tissue, epithelial tissue, nerve tissue, or vascular tissue.

31. A method of actuating a target tissue or sensing a parameter associated with the target tissue in a biological environment, said method comprising:
providing an implantable biomedical device comprising:
a bioresorbable substrate;
an electronic device comprising a plurality of inorganic semiconductor components supported by said bioresorbable substrate, wherein at least one of said inorganic semiconductor components has at least one physical dimension less than or equal to 100 microns; and
a barrier layer encapsulating at least a portion of said inorganic semiconductor components;
contacting said implantable biomedical device with the target tissue in a biological environment;
at least partially resorbing said bioresorbable substrate in said biological environment, thereby establishing conformal contact between said implantable biomedical device and said target tissue in said biological environment; and
actuating the target tissue or sensing the parameter associated with the target tissue that is in conformal contact with the implantable biomedical device.

32. The method of claim 31, wherein resorption of said bioresorbable substrate establishes physical contact or electrical contact between said electronic device and said target tissue.

33. The method of claim 31, further comprising the step of sensing the parameter associated with the target tissue that is in conformal contact with the implantable biomedical device, wherein said step of sensing the parameter associated with the target tissue that is in conformal contact with the implantable biomedical device comprises measuring voltage at a surface of the target tissue, measuring electromagnetic radiation at a surface of the target tissue or measuring a current at a surface of the target tissue.

34. The method of claim 31, further comprising the step of actuating the target tissue that is in conformal contact with the implantable biomedical device, wherein said step of actuating the target tissue that is in conformal contact with the implantable biomedical device comprises generating a voltage at a surface of the target tissue, generating electromagnetic radiation at a surface of the target tissue or generating a current at a surface of the target tissue.

35. An implantable biomedical device for actuating a target tissue or sensing a parameter associated with the target tissue in a biological environment, said device comprising:
an electrode array comprising a plurality of individually addressable inorganic semiconductor components, wherein each inorganic semiconductor component has at least one physical dimension less than or equal to 100 microns;
a barrier layer having a mesh structure, wherein said barrier layer at least partially supports said electrode array; and
a bioresorbable substrate supporting said electrode array, said barrier layer or both of said electrode array and said barrier layer;
wherein upon contact with said biological environment said bioresorbable substrate is at least partially resorbed, thereby establishing conformal contact between said electrode array and said target tissue in said biological environment.

36. The device of claim 35, wherein said inorganic semiconductor components of said electrode array are physically separated from each other.

37. The device of claim 35, wherein said barrier layer is in physical contact with at least a portion of said inorganic semiconductor components of said electrode array or wherein said bioresorbable substrate is in physical contact with at least a portion of said electrode array or in physical contact with at least a portion of said barrier layer.

38. The device of claim 35, wherein each of said inorganic semiconductor components of said array is in electrical contact with at least one electronic interconnect.

39. The device of claim 35, wherein said bioresorbable substrate comprises a poly(glycerol-sebacate) (PGS), polydioxanone, poly(lactic-co-glycolic acid) (PLGA), polylactic acid (PLA), collagen, chitosan, fibroin, or any combination of these.

40. The device of claim 35, wherein said bioresorbable substrate comprises a silkworm fibroin, spider silk, insect silk, recombinant silk, or any combination of these.

41. The device of claim 35, wherein said bioresorbable substrate has a thickness selected from the range of 100 nanometers to 10000 μm.

42. The device of claim 35, wherein resorption of said bioresorbable substrate establishes physical contact or electrical contact between said electrode array and said target tissue.

43. The device of claim 35, wherein said mesh structure is a perforated mesh structure or a tentacle mesh structure.

44. The device of claim 35, wherein said electrode array comprises 10 to 1000 inorganic semiconductor components.

45. The device of claim 35, wherein each of said inorganic semiconductor components has a thickness selected over the range of 100 nanometers to 10 microns.

46. The device of claim 35, wherein said inorganic semiconductor components further comprise a bioinert metal or a biocompatible metal.

47. The device of claim 35, wherein said barrier layer has a thickness selected from the range of 1 μm to 100 μm.

48. A method for actuating a target tissue or sensing a parameter associated with the target tissue in a biological environment, the method comprising:

providing an implantable biomedical device comprising:
an electrode array comprising a plurality of individually addressable inorganic semiconductor components, wherein each inorganic semiconductor component has at least one physical dimension less than or equal to 100 microns;
a barrier layer having a mesh structure, wherein said barrier layer at least partially supports said electrode array; and
a bioresorbable substrate supporting said electrode array, said barrier layer or both of said electrode array and said barrier layer;
contacting said implantable biomedical device with the target tissue in a biological environment; wherein upon contact with said biological environment said bioresorbable substrate is at least partially resorbed, thereby establishing conformal contact between said electrode array and said target tissue in said biological environment; and
actuating the target tissue or sensing the parameter associated with the target tissue that is in conformal contact with the implantable biomedical device.

49. The method of claim 48, wherein said biological environment is an in-vivo biological environment.

50. The method of claim 48, wherein resorption of said bioresorbable substrate establishes physical contact or electrical contact between said implantable biomedical device and said target tissue.

51. The method of claim 48, further comprising the step of sensing the parameter associated with the target tissue that is in conformal contact with the implantable biomedical device, wherein said step of sensing the parameter associated with the target tissue that is in conformal contact with the implantable biomedical device comprises measuring voltage at a surface of the target tissue, measuring electromagnetic radiation at a surface of the target tissue or measuring a current at a surface of the target tissue.

52. The method of claim 48, further comprising the step of actuating the target tissue that is in conformal contact with the implantable biomedical device, wherein said step of actuating the target tissue that is in conformal contact with the implantable biomedical device comprises generating a voltage at a surface of the target tissue, generating electromagnetic radiation at a surface of the target tissue or generating a current at a surface of the target tissue.

* * * * *